US010092352B2

(12) United States Patent
Rudie

(10) Patent No.: US 10,092,352 B2
(45) Date of Patent: *Oct. 9, 2018

(54) COOLED MICROWAVE DENERVATION

(71) Applicant: Denervx LLC, Maple Grove, MN (US)

(72) Inventor: Eric N. Rudie, Maple Grove, MN (US)

(73) Assignee: Denervx LLC, Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/068,252

(22) Filed: Mar. 11, 2016

(65) Prior Publication Data

US 2016/0262833 A1    Sep. 15, 2016

Related U.S. Application Data

(62) Division of application No. 14/032,013, filed on Sep. 19, 2013, now Pat. No. 9,333,035.

(Continued)

(51) Int. Cl.
*A61B 18/18* (2006.01)
*A61B 18/00* (2006.01)

(52) U.S. Cl.
CPC .. *A61B 18/1815* (2013.01); *A61B 2018/0022* (2013.01); *A61B 2018/00023* (2013.01);
(Continued)

(58) Field of Classification Search
CPC ........ A61B 18/1815; A61B 2018/0022; A61B 2018/00285; A61B 2018/00511;
(Continued)

(56) References Cited

U.S. PATENT DOCUMENTS 4,583,556 A * 4/1986 Hines ................. A61B 18/1815
607/116
5,304,214 A    4/1994 DeFord et al.
(Continued)

OTHER PUBLICATIONS

Sievert H., et al., CardioVascular Center Frankfurt, Frankfurt Germany. Innovations in Cardiovascular Interventions ICI 2009, Tel Aviv, Israel, Dec. 6-8, 2009, Radiofrequency Ablation of the Renal Arteries for Treatment of Severe Hypertension: A New treatment Concept.

(Continued)

*Primary Examiner* — Thomas Giuliani
(74) *Attorney, Agent, or Firm* — Kinney & Lange, P.A.

(57) ABSTRACT

A device and method is disclosed for creating a lesion in adventitia tissue of a renal artery and/or a region of tissue surrounding the adventitia tissue while protecting intima and media tissue of the renal artery from injury. A catheter carrying a microwave antenna is positioned within the renal artery. Cooling fluid is circulated around the microwave antenna in thermal contact with the intima of the renal artery. Power is supplied to the microwave antenna to cause microwave energy to be emitted omnidirectionally from the microwave antenna. The power supplied to the microwave antenna and the cooling fluid circulated around the microwave antenna are controlled to cause the adventitia tissue and/or the region of tissue surrounding the adventitia tissue to be heated to a temperature sufficient to cause thermal damage while the intima and media tissue are maintained at a temperature where thermal damage does not occur.

12 Claims, 95 Drawing Sheets

Related U.S. Application Data

(60) Provisional application No. 61/703,101, filed on Sep. 19, 2012, provisional application No. 61/734,419, filed on Dec. 7, 2012.

(52) U.S. Cl.
CPC ............... *A61B 2018/00166* (2013.01); *A61B 2018/00285* (2013.01); *A61B 2018/00434* (2013.01); *A61B 2018/00511* (2013.01); *A61B 2018/00517* (2013.01); *A61B 2018/00529* (2013.01); *A61B 2018/00541* (2013.01); *A61B 2018/00547* (2013.01); *A61B 2018/00577* (2013.01); *A61B 2018/00642* (2013.01); *A61B 2018/00702* (2013.01); *A61B 2018/00744* (2013.01); *A61B 2018/00785* (2013.01); *A61B 2018/00791* (2013.01); *A61B 2018/1846* (2013.01); *A61B 2018/1861* (2013.01)

(58) Field of Classification Search
CPC ........... A61B 2018/00023; A61B 2018/00434; A61B 2018/00642; A61B 2018/00791; A61B 2018/1846; A61B 2018/1861
USPC .................................................... 606/33, 41
See application file for complete search history.

(56) References Cited

U.S. PATENT DOCUMENTS

| | | |
|---|---|---|
| 5,348,554 A | 9/1994 | Imran et al. |
| 5,620,480 A | 4/1997 | Rudie |
| 5,649,973 A | 7/1997 | Tierney et al. |
| 5,979,454 A | 11/1999 | Anvari et al. |
| 5,987,360 A | 11/1999 | McGrath et al. |
| 6,047,216 A | 4/2000 | Carl et al. |
| 6,056,745 A | 5/2000 | Panescu et al. |
| 6,106,518 A | 8/2000 | Wittenberger et al. |
| 6,122,551 A | 9/2000 | Rudie et al. |
| 6,223,085 B1* | 4/2001 | Dann ................ A61B 18/1492 606/29 |
| 6,272,384 B1 | 8/2001 | Simon et al. |
| 6,283,959 B1 | 9/2001 | Lalonde et al. |
| 6,283,988 B1 | 9/2001 | Laufer et al. |
| 6,289,249 B1 | 9/2001 | Arndt et al. |
| 6,427,089 B1* | 7/2002 | Knowlton ............ A61B 18/18 607/101 |
| 6,490,488 B1 | 12/2002 | Rudie et al. |
| 6,512,956 B2 | 1/2003 | Arndt et al. |
| 6,514,249 B1 | 2/2003 | Maguire et al. |
| 6,592,579 B2 | 7/2003 | Arndt et al. |
| 6,740,108 B1 | 5/2004 | Just et al. |
| 6,807,446 B2* | 10/2004 | Fenn ................ A61N 1/403 606/33 |
| 6,918,869 B2 | 7/2005 | Shaw et al. |
| 7,052,508 B2 | 5/2006 | Werneth |
| 7,081,112 B2 | 7/2006 | Joye et al. |
| 7,097,641 B1 | 8/2006 | Arless et al. |
| 7,132,439 B2 | 11/2006 | Wang et al. |
| 7,162,303 B2 | 1/2007 | Levin et al. |
| 7,311,703 B2 | 12/2007 | Turovskiy et al. |
| 7,465,300 B2 | 12/2008 | Arless et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,717,948 B2 | 5/2010 | Demarais et al. |
| 7,756,583 B2 | 7/2010 | Demarais et al. |
| 7,840,271 B2 | 11/2010 | Kieval et al. |
| 7,853,333 B2 | 12/2010 | Demarais |
| 7,875,024 B2 | 1/2011 | Turovskiy et al. |
| 7,925,352 B2 | 4/2011 | Stack et al. |
| 7,937,143 B2 | 5/2011 | Demarais et al. |
| 7,951,140 B2 | 5/2011 | Arless et al. |
| 8,140,170 B2 | 3/2012 | Rezai et al. |
| 8,287,526 B2 | 10/2012 | Arless et al. |
| 8,473,067 B2 | 6/2013 | Hastings et al. |
| 8,548,600 B2 | 10/2013 | Deem et al. |
| 8,620,423 B2 | 12/2013 | Demarais et al. |
| 8,626,300 B2 | 1/2014 | Demarais et al. |
| 8,641,709 B2 | 2/2014 | Sauvageau et al. |
| 8,652,129 B2 | 2/2014 | Wu et al. |
| 8,676,309 B2 | 3/2014 | Deem et al. |
| 8,740,895 B2 | 6/2014 | Mayse et al. |
| 8,777,943 B2 | 7/2014 | Mayse et al. |
| 8,808,280 B2 | 8/2014 | Mayse et al. |
| 8,821,489 B2 | 9/2014 | Mayse et al. |
| 9,333,035 B2 | 5/2016 | Rudie |
| 2002/0087208 A1 | 7/2002 | Koblish et al. |
| 2003/0055471 A1* | 3/2003 | Fenn ................ A61N 5/02 607/101 |
| 2004/0133254 A1* | 7/2004 | Sterzer ................ A61B 18/18 607/101 |
| 2005/0249667 A1 | 11/2005 | Tuszynski et al. |
| 2005/0288730 A1 | 12/2005 | Deem et al. |
| 2006/0041277 A1 | 2/2006 | Deem et al. |
| 2006/0111704 A1 | 5/2006 | Brenneman et al. |
| 2006/0265015 A1 | 11/2006 | Demarais et al. |
| 2007/0129720 A1 | 6/2007 | Demarais et al. |
| 2007/0142879 A1 | 6/2007 | Greenberg et al. |
| 2007/0173899 A1 | 7/2007 | Levin et al. |
| 2007/0203551 A1 | 8/2007 | Cronin et al. |
| 2008/0255642 A1 | 10/2008 | Zarins et al. |
| 2008/0294155 A1 | 11/2008 | Cronin |
| 2009/0024195 A1 | 1/2009 | Rezai et al. |
| 2009/0062873 A1 | 3/2009 | Wu et al. |
| 2009/0076409 A1 | 3/2009 | Wu et al. |
| 2010/0004650 A1* | 1/2010 | Ormsby ............ A61B 18/1492 606/41 |
| 2010/0137857 A1* | 6/2010 | Shroff ................ A61B 18/18 606/33 |
| 2010/0137860 A1 | 6/2010 | Demarais et al. |
| 2010/0168731 A1 | 7/2010 | Wu et al. |
| 2010/0174282 A1 | 7/2010 | Demarais et al. |
| 2010/0222851 A1 | 9/2010 | Deem et al. |
| 2010/0262137 A1 | 10/2010 | Nye et al. |
| 2011/0060324 A1 | 3/2011 | Wu et al. |
| 2011/0092781 A1 | 4/2011 | Gertner |
| 2011/0184337 A1 | 7/2011 | Evans et al. |
| 2011/0196359 A1 | 8/2011 | Arless et al. |
| 2011/0200171 A1 | 8/2011 | Beetel et al. |
| 2011/0257523 A1 | 10/2011 | Hastings et al. |
| 2011/0257562 A1 | 10/2011 | Schaer |
| 2011/0257564 A1 | 10/2011 | Demarais et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0301587 A1 | 12/2011 | Deem et al. |
| 2011/0306904 A1 | 12/2011 | Jacobson et al. |
| 2011/0307034 A1 | 12/2011 | Hastings et al. |
| 2012/0019079 A1 | 1/2012 | Ziegler et al. |
| 2012/0029495 A1 | 2/2012 | Wittenberger |
| 2012/0029496 A1 | 2/2012 | Smith |
| 2012/0029510 A1 | 2/2012 | Haverkost |
| 2012/0029512 A1 | 2/2012 | Willard et al. |
| 2012/0029513 A1 | 2/2012 | Smith et al. |
| 2012/0059286 A1 | 3/2012 | Hastings et al. |
| 2012/0065506 A1 | 3/2012 | Smith |
| 2012/0089047 A1 | 4/2012 | Ryba et al. |
| 2012/0101413 A1 | 4/2012 | Beetel et al. |
| 2012/0116383 A1 | 5/2012 | Mauch et al. |
| 2012/0116486 A1* | 5/2012 | Naga ................ A61B 18/1815 607/102 |
| 2012/0123243 A1 | 5/2012 | Hastings |
| 2012/0130359 A1 | 5/2012 | Turovskiy |
| 2012/0130458 A1 | 5/2012 | Ryba et al. |
| 2012/0136350 A1 | 5/2012 | Goshgarian et al. |
| 2012/0143097 A1 | 6/2012 | Pike, Jr. |
| 2012/0172863 A1 | 7/2012 | Brannan |
| 2012/0191079 A1 | 7/2012 | Moll et al. |
| 2012/0191083 A1 | 7/2012 | Moll et al. |
| 2012/0232436 A1 | 9/2012 | Warnking |
| 2012/0259269 A1 | 10/2012 | Meyer |
| 2012/0259326 A1 | 10/2012 | Brannan et al. |
| 2012/0265198 A1 | 10/2012 | Crow et al. |

(56) References Cited

U.S. PATENT DOCUMENTS

| | | |
|---|---|---|
| 2012/0296329 A1 | 11/2012 | Ng |
| 2012/0330306 A1 | 12/2012 | Long et al. |
| 2013/0053732 A1 | 2/2013 | Heuser |
| 2013/0079835 A1 | 3/2013 | Sluijter et al. |
| 2013/0085493 A1 | 4/2013 | Bloom et al. |
| 2013/0090647 A1 | 4/2013 | Smith |
| 2013/0090650 A1 | 4/2013 | Jenson et al. |
| 2013/0090652 A1 | 4/2013 | Jenson |
| 2013/0116683 A1 | 5/2013 | Shadduck et al. |
| 2013/0116687 A1 | 5/2013 | Willard |
| 2013/0131668 A1 | 5/2013 | Schaer |
| 2013/0144251 A1 | 6/2013 | Sobotka |
| 2013/0144283 A1 | 6/2013 | Barman |
| 2013/0158441 A1 | 6/2013 | Demarais et al. |
| 2013/0158442 A1 | 6/2013 | Demarais et al. |
| 2013/0165822 A1 | 6/2013 | Demarais et al. |
| 2013/0165917 A1 | 6/2013 | Mathur et al. |
| 2013/0165923 A1 | 6/2013 | Mathur et al. |
| 2013/0165925 A1 | 6/2013 | Mathur et al. |
| 2013/0165926 A1 | 6/2013 | Mathur et al. |
| 2013/0172877 A1 | 7/2013 | Subramaniam et al. |
| 2013/0172881 A1 | 7/2013 | Hill et al. |
| 2013/0178824 A1 | 7/2013 | Buelna |
| 2013/0197555 A1 | 8/2013 | Schaer |
| 2013/0204241 A1 | 8/2013 | Baust |
| 2013/0274658 A1 | 10/2013 | Steinke et al. |
| 2013/0274731 A1 | 10/2013 | Anderson et al. |
| 2013/0274735 A1 | 10/2013 | Hastings et al. |
| 2013/0289369 A1 | 10/2013 | Margolis |
| 2013/0289678 A1 | 10/2013 | Clark et al. |
| 2013/0296767 A1 | 11/2013 | Zarins et al. |
| 2013/0296853 A1 | 11/2013 | Sugimoto et al. |
| 2013/0304047 A1 | 11/2013 | Grunewald et al. |
| 2013/0304052 A1 | 11/2013 | Rizq et al. |
| 2014/0012251 A1 | 1/2014 | Himmelstein et al. |
| 2014/0018605 A1 | 1/2014 | Soltesz et al. |
| 2014/0018789 A1 | 1/2014 | Kaplan et al. |
| 2014/0018794 A1 | 1/2014 | Anderson et al. |
| 2014/0025069 A1 | 1/2014 | Willard et al. |
| 2014/0031811 A1 | 1/2014 | Brannan |
| 2014/0039487 A1 | 2/2014 | Brannan et al. |
| 2014/0042154 A1 | 2/2014 | Cronin |
| 2014/0046174 A1 | 2/2014 | Ladtkow et al. |
| 2014/0046175 A1 | 2/2014 | Ladtkow et al. |
| 2014/0046313 A1 | 2/2014 | Pederson et al. |
| 2014/0046316 A1 | 2/2014 | Ladtkow et al. |
| 2014/0066915 A1 | 3/2014 | Zhou et al. |
| 2014/0066916 A1 | 3/2014 | Coe et al. |
| 2014/0066920 A1 | 3/2014 | Azamian et al. |
| 2014/0066921 A1 | 3/2014 | Coe et al. |
| 2014/0066922 A1 | 3/2014 | Coe et al. |
| 2014/0081259 A1 | 3/2014 | Deem et al. |
| 2014/0107639 A1 | 4/2014 | Zhang et al. |
| 2014/0114215 A1 | 4/2014 | Melder et al. |
| 2014/0114305 A1 | 4/2014 | Zarins et al. |
| 2014/0257271 A1 | 9/2014 | Mayse et al. |
| 2015/0119870 A1* | 4/2015 | Rudie ............ A61B 18/1815 606/33 |

OTHER PUBLICATIONS

International Search Report for PCT/US2013/060722, dated Dec. 16, 2013.

Wendy Dougherty and Jeff Warren, "Medtronic Releases Results of SYMPLICITY HTN-3 Medtronic Commits to Further Clinical Investigation and Determining Path Forward for Next U.S. IDE with FDA", Mar. 29, 2014.

International Preliminary Report on Patentability dated Mar. 24, 2015, for PCT/US2013/060722.

JB Bederson et al., "Evaluation of 2, 3, 5-triphenyltetrazolium chloride as a stain for detection and quantification of experimental cerebral infarction in rats", Stroke. 1986;17:1304-1308.

http://www.engineeringtoolbox.com/liquid-dielectric-constants-d_1263.htm, Jun. 14, 2012.

Kira Jokela, "Evaluation of compliance with SAR limits on the basis of external RFEM-field and induced current measurements", Current trends in health and safety risk assessment of work-related exposure to EMFs, Milan, Feb. 14-16, 2007, Non-Ionizing Radiation Laboratory STUK, Radiation and Nuclear Safety Authority (Finland).

http://www.rfcafe.com/references/electrical/dialectric-constants-strengths.htm, Jun. 14, 2012.

Bill Riddle et al., "Complex Permittivity Measurements of Common Plastics Over Variable Temperatures",Senior Member IEEE, IEEE Transactions on Microwave Theory and Techniques, vol. 51, No. 3, pp. 727-733, Mar. 2003.

Oliver Merckel and Jean-Charles Bolomey, "E-Field Distribution modeling in Homogeneous Phantom for a rapid SAR measurement", Oct. 8, 2013.

Joseph C. Cerny, MD and Daniel Karsch, MD, "Aberrant Renal Arteries", UROLOGY, Dec. 1973, vol. II, No. 6, pp. 623-626.

R.A. Omary et al.,"Magnetic Resonance-Guided Angioplasty of Renal Artery Stenosis in a Pig Model: A Feasibility Study", Departments of Radiology and Medical Physics, University of Wisconsin, Madison, Madison, Wisconsin USA 53792-3252, Oct. 8, 2013.

Ronald A. Bergman, Ph.D., et al., "Illustrated Encyclopedia of Human Anatomic Variation: Opus II: Cardiovascular System: Arteries: Abdomen" Renal Arteries, Anatomy Atlases, www.anatomyatlases.org, A digital library of anatomy information, Curated by Ronald A. Bergman, Ph.D, Mar. 26, 2012.

White C J, Circ Cardiovasc Interv 2010;3:184-192, Figure 7 and presentation notes, American Heart Association.

Yamamoto T et al. Arterioscler Thromb Vasc Biol, 1996;16:172-177, American Heart Association.

Daniel S. Atherton et al."Micro-anatomy of the renal sympathetic nervous system: A human postmortem histologic study", http://onlinelibrary.wiley.com/doi/10.1002/ca.21280/full, Apr. 21, 2012.

Top 10 Innovations for 2012, Oct. 8, 2013.

Lilach O. Lerman et al."Noninvasive Evaluation of a Novel Swine Model of Renal Artery Stenosis" Journal of the American Society of Nephruology 10: 1445-1465, 1999.

Paul A. Sobotka, MC, FACC, FACP, "Sympatho-Renal Axis and Sympathetic Hyperactivity", The Ohio State University, Oct. 8, 2013.

Xu D, Pollock M., "Experimental nerve thermal injury.", http://www.ncbi.nlm.nih.gov/pubmed/818/6963, Apr. 1994.

Bakris GL et al., "Baroreflex Activation Therapy provides durable benefit in patiens with resistant hypertension: results of long-term follow-up in the Rheos Pivotal Trial", http://mcbi.nlm.nih.gov/pubmed/22342299, Mar. 2012.

Susan Jeffrey, "Catheter-based renal denervation reduces resistant hypertension", Mar. 30, 2009, http://www.theheart.org/article/953771.co.

Bisognano JD et al., "Baroreflex activation therapy lowers blood pressure in patients with resistant hypertension: results from the double-blind, randomized, placebo-controlled rheos pivotal trial.", http://www.ncbi.nlm.nih.gov/bupmed/21816315, Aug. 2011.

Markus P. Schlaich et al., "Renal Denervation and Hypertension", http://www.nature.com/ajh/journal/v24/n6/full/ajh201135a.html, Jun. 2011.

Vasilios Papademetriou et al., "Renal Sympathetic Denervation for the Treatment of Difficult-to-Control or Resistant Hypertension",International Journal of Hypertension, vol. 2011, Article ID 196518, 8 pages, Jan. 19, 2011.

Subhash Banerjee MD, "Transcatheter Renal Denervation", http://www.invasivecardiology.com/print/3211, Mar. 5, 2012.

Keith A. Thompson et al., "Drug-resistant Hypertension: Is Renal Sympathetic Denervation the Answer?", Curr Cardiol Rep (2011) 13:93-95.

Waleska C. Dornas and Marcelo E. Silva, "Animal models for study of arterial hypertension", J. Biosci. 36 731-737, Sep. 2011.

Christopher J. White,"Optimizing Outcomes for Renal Artery Intervention", Circ Cardiovasc Interv 2010;3;184-192, http://circinterventions.ahajournals.org/content/3/2/184.full.

David C. Levin et al., "New Curved Catheter for Renal Angioplasty", AJR 138:359-360, Feb. 1982.

(56) References Cited

OTHER PUBLICATIONS

W. Sripairojthikoon et al., "Renal nerve contribution to NaCl-exacerbated hypertension in spontaneously hypertensive rats", http://hyper.ahajournals.org, 1989.
Boshen Liu et al., "Systemic and Renal-Specific Sympathoinhibition in Obesity Hypertension", The FASEB Journal. 2011;25:1078.2.
Thomas E. Lohmeier et al. "Disparate Effects of Systemic and Renal-Specific Sympathoinhibition in Obesity Hypertension", 2011.
Dr. Camiela Gabriel, Report Documentation Page, "Compilation of the Dielectric Properties of Body Tissues at RF and Microwave Frequencies", Sep. 15, 1993 to Dec. 14, 1995.
Sievert H., et al., CardioVascular Center Frankfurt, Frankfurt Germany. Innovations in Cardiovasculat Interventions ICI 2009, Tel Aviv, Israel, Dec. 6-8, 2009, Radiofrequency Ablation of the Renal Arteries for Treatment of Severe Hypertension: A New treatment Concept.
Michael R. Jaff, DO, Renal Artery Stenting is Still Alive and Well, ICI Tel Aviv, Israel, Dec. 5, 2011.
Andrej Schmidt, MD and Dierk Scheinert, MD, Endovascular Renal Artery Denervation for Treatment of Therapy-Refractory Hypertension, Center for Vascular Medicine, Aniology and Vascular Surgery Park Hospital and Heartcenter Leipzig, Germany, 2010.
Prof. Dierk Scheinert, Renal Sympathetic Nerve Ablation for Resistant Hypertension, Center for Vascular Medicine, Angiology and Vascular Surgery, Park Hospital Leipzig, Germany, Oct. 8, 2013.
Dierk Scheinert, MD, Renal Denervation by RF-Ablation in Patients with Refractory Hypertension, Departments of Angiology Park Hospital Leipzig, Germany & University of Leipzig—Heart Center, Germany, Oct. 8, 2013.
Maya Medical, Single-Step Renal Denervation with the OneShot(tm) Ablation System, Oct. 8, 2013.
Prof. DR. T. Zeller MD, Renal Denervation Therapy: Tips and Tricks, Herz-Zentrum Bad Krozingen, Germany, Oct. 8, 2013.
Henry Krum et al., "Catheter-Based Renal Sympathetic Denervation in the Management of Resistant Hypertension", Centre of Cardiovascular Research & Education in Therapeutics, Monash Univeristy/Alfred Hospital, Melbourne, Australia, 2009.
Docteru Guillaume Bobrie, Device-Based Antihypertensive Therapy, Therapeutic Modulation of the Autonomic Nervous System, Service d'HTA—HEGP—Paris, Oct. 8, 2013.
Eugene Braunwald, M.D., Introduction to Symposium, Aug. 30, 2011.
Gerd Hasenfuss, New Generation Barostim neo(tm) System Preliminary Results and Discussion, Heart Center and Heart Research Center University of Geottingen Germany, Oct. 8, 2013.
Dierk Scheinert, MD, Renal Denervation by RF Ablation in Patients with Refractory Hypertension, Departments of Angiology Park Hospital Leipzig, Germany & University of Leipzig—Heart Center, Germany, Jan. 28, 2010.
Alberto Zanchetti, Carotid Baroreflex Physiology and Baroreflex Activation Therapy Mechanism of Action, Paris—ESC Aug. 30, 2012, Universita di Milano, Instituto Auxologico Italiano, Milano, Italy.
"Catheter-based renal sympathetic denervation for the treatment of resistant arterial hypertension in Poland—experts consensus statement", www.kardiologiapolska.pl, 2011.
Felix Mahfoud et al., Editorial Future Cardiology, "Is there a role for renal sympathetic denervation in the future treatment of resistant hypertension?", 10.22/FCA.11.49 2011 Future Medicine Ltd., pp. 591-594.
Paul A. Sobotka et al. "Sympatho-renal axis in chronic disease", Clin Res Cardiol (2011) 100:1049-1057.
http://ducknetweb.blogspot.com/2010/11/medtronic-acquires-hypertensio . . . , Nov. 24, 2010.
Jake Hartman, "Renal Denervation: The Next Big Thing in Treating Hypertension?", Oct. 11, 2011, http://www.advisory.com/Research/Cardiovascular-Roundtable/Cardiov . . . .
http://clinicaltrials.gov/ct2/results:term=renal+denervation, Mar. 20, 2012.
Renal sympathetic denervation in patiens with treatment-resistant hypertension (The Symplicity HTN-2 Trial): a randomised controlled trial, http://www.thelancet.com/journals/lancet/article/PIIS0140-6736(10)6203 . . . , Nov. 17, 2010.
A. Peyman et al., "Dielectric Properties of Tissues at Microwave Frequencies", Dec. 22, 2009.
Vibhuti N. Singh, MD, "Renal artery Angioplasty", http://emedicine.medscape.com/article/1817671-overview, May 14, 2012.
"Hypertension and the Symplicity Renal Denerviation System", 2011.
Mary Stuart, "Renal Denervaion: Device Market's Gold Rush", http://www.elsevierbi.com/publications/start-up/17/4/renal-denervation-device-markets-gold-rush?p=1, May 10, 2012.
"Renal Sympathetic-Nerve Ablation for Uncontrolled Hypertension", The New England Journal of Medicine, Aug. 27, 2009.
Martin H. Kurzidim et al., "Studies on the vasa vasorum of the human renal artery", Ann Anat (1999) 181: 223-227, http://www.urbanfischer.de/journals/annanat.
Henry Krum et al., "Catherter-based renal sympathetic denervation for resistant hypertension:a multicentre safety and proof-of-principle cohort study", www.thelancet.com vol. 373, Apr. 11, 2009.
Krishna J. Rocha-Singh, MD,FACC, FAHA, FSCAI, FSVM, "Renal Artery Denervation: A Brave New Frontier, Emerging therapies for treating patients with severe, treatment-resistant hypertension", Endovascular Today, Feb. 2012.
Jacek Kadziela, MD, PhD et al., "Evaluating Renal Denervation, A summary of ongoing and planned studies, as well as potential collateral benefits.", Endovasular Today, pp. 40-44, Feb. 2012.
Krishna J. Rocha-Singh, MD, "The Renal Renaissance", Endovascular Today, p. 4, Feb. 2012.

\* cited by examiner

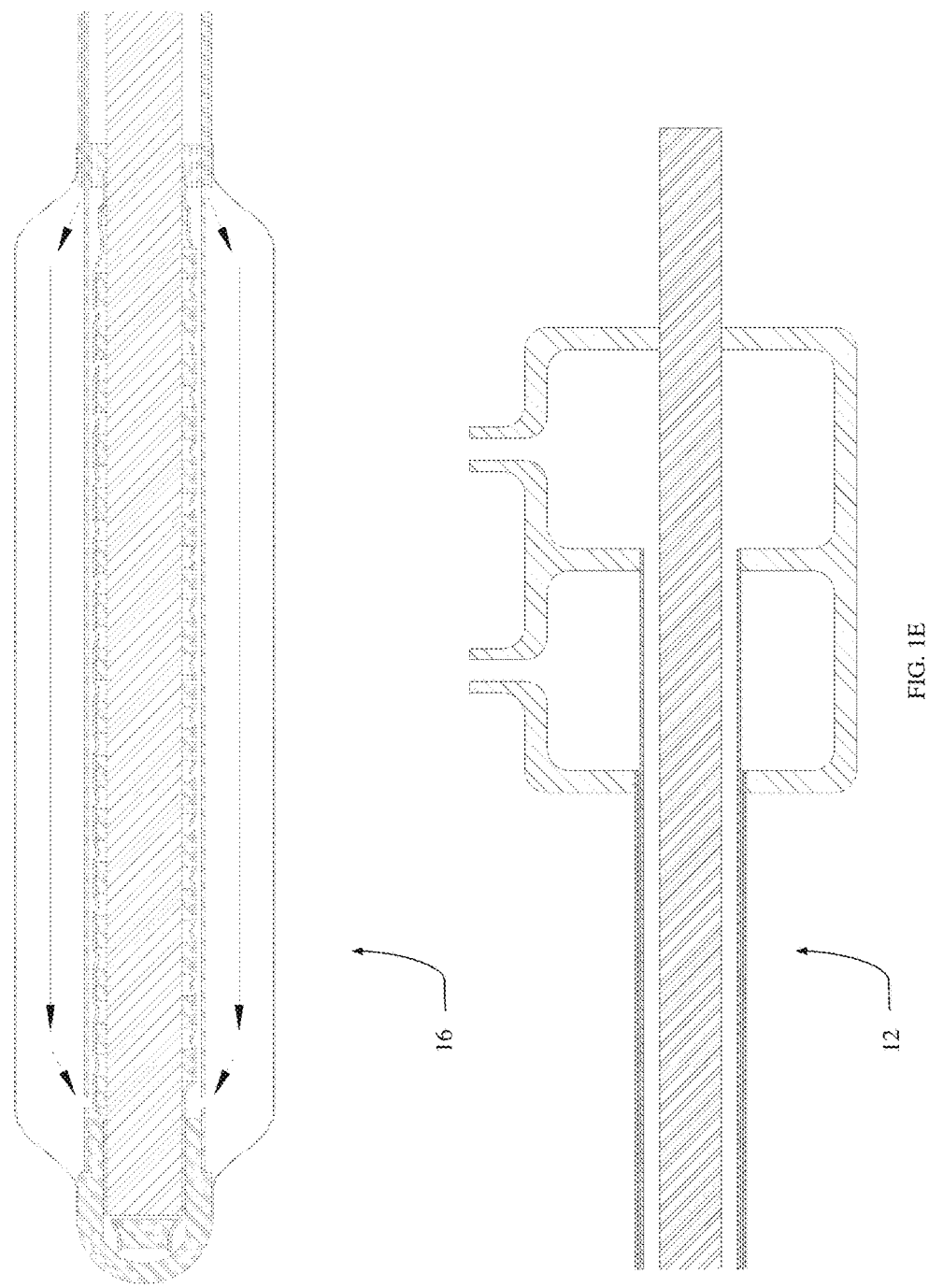

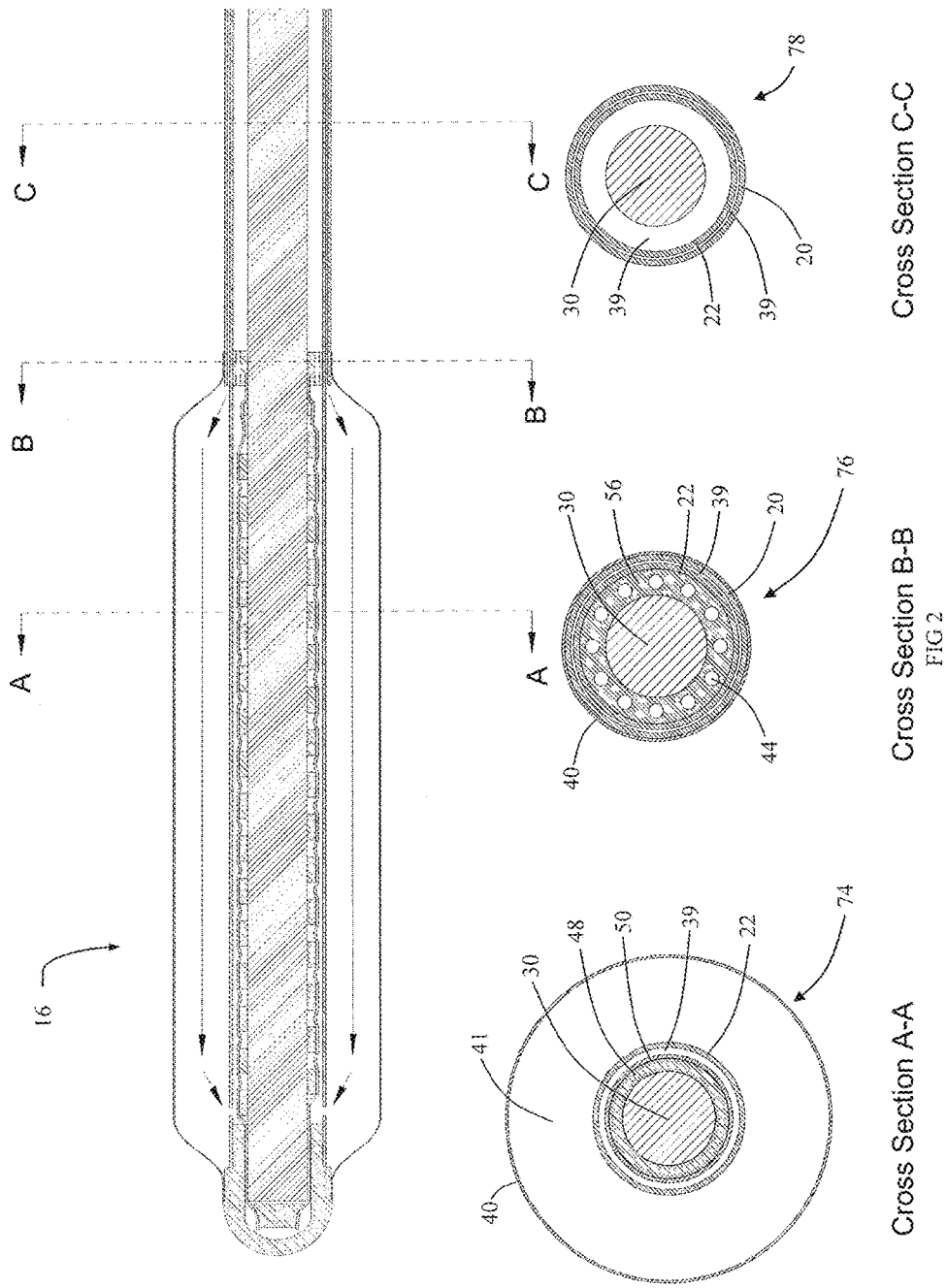

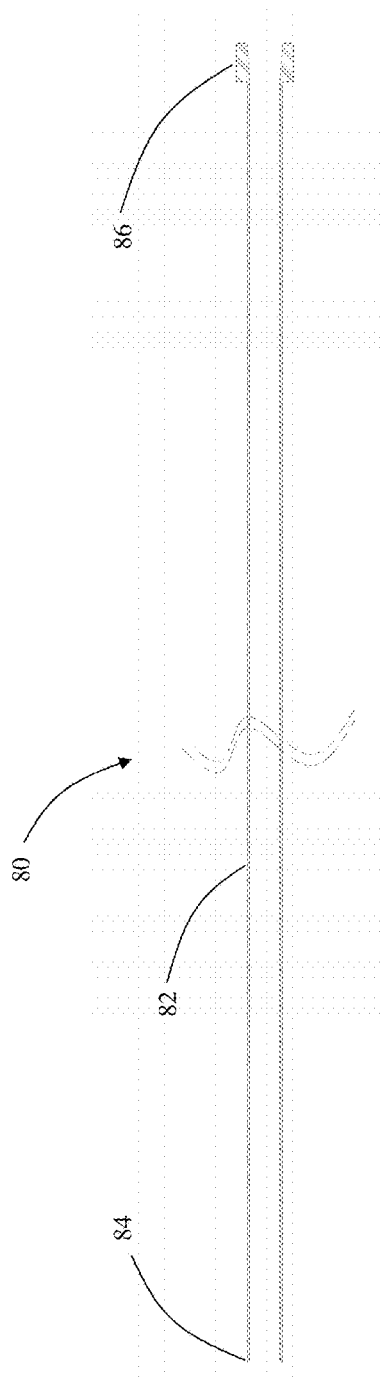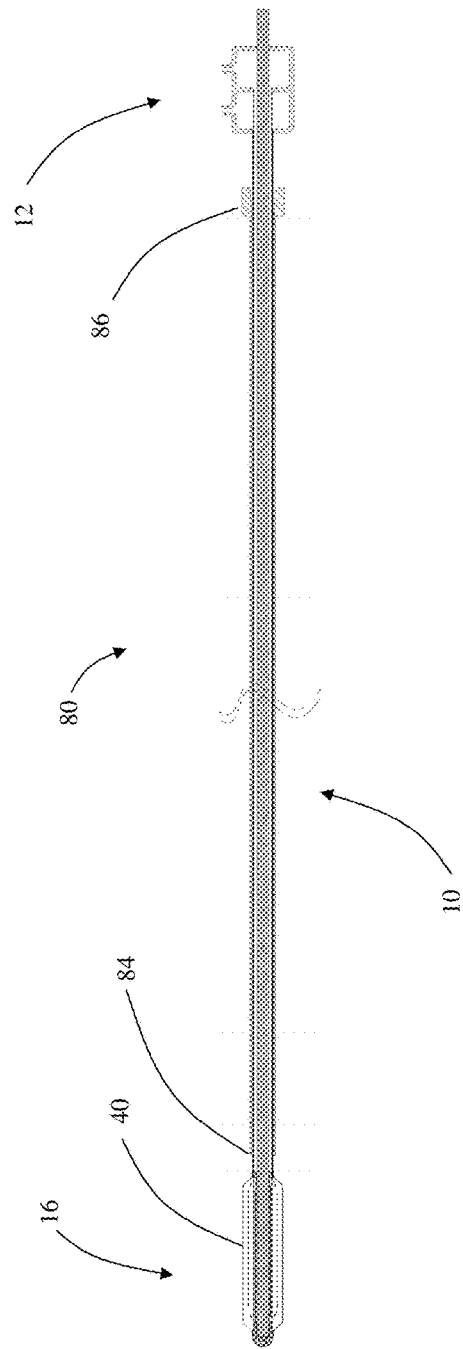
FIG 4A
FIG 4B

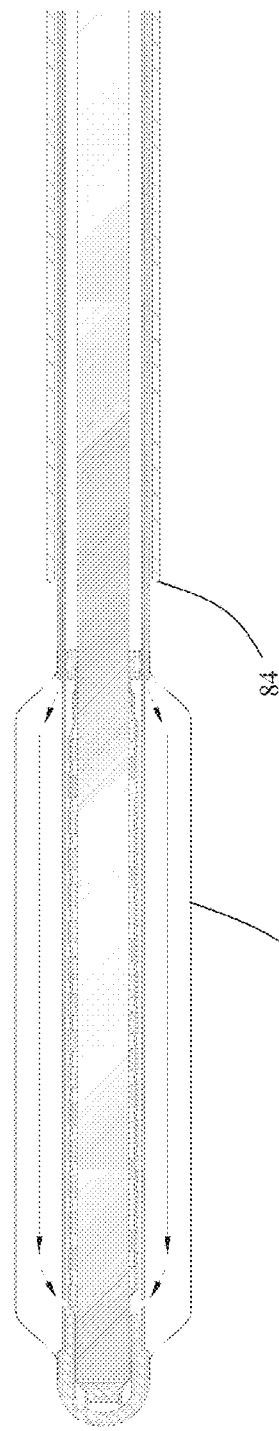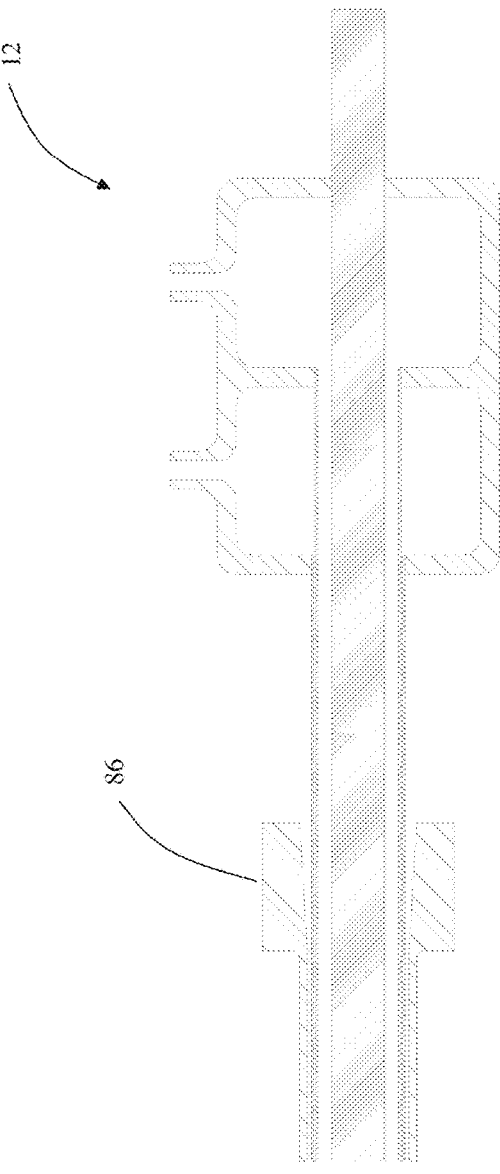

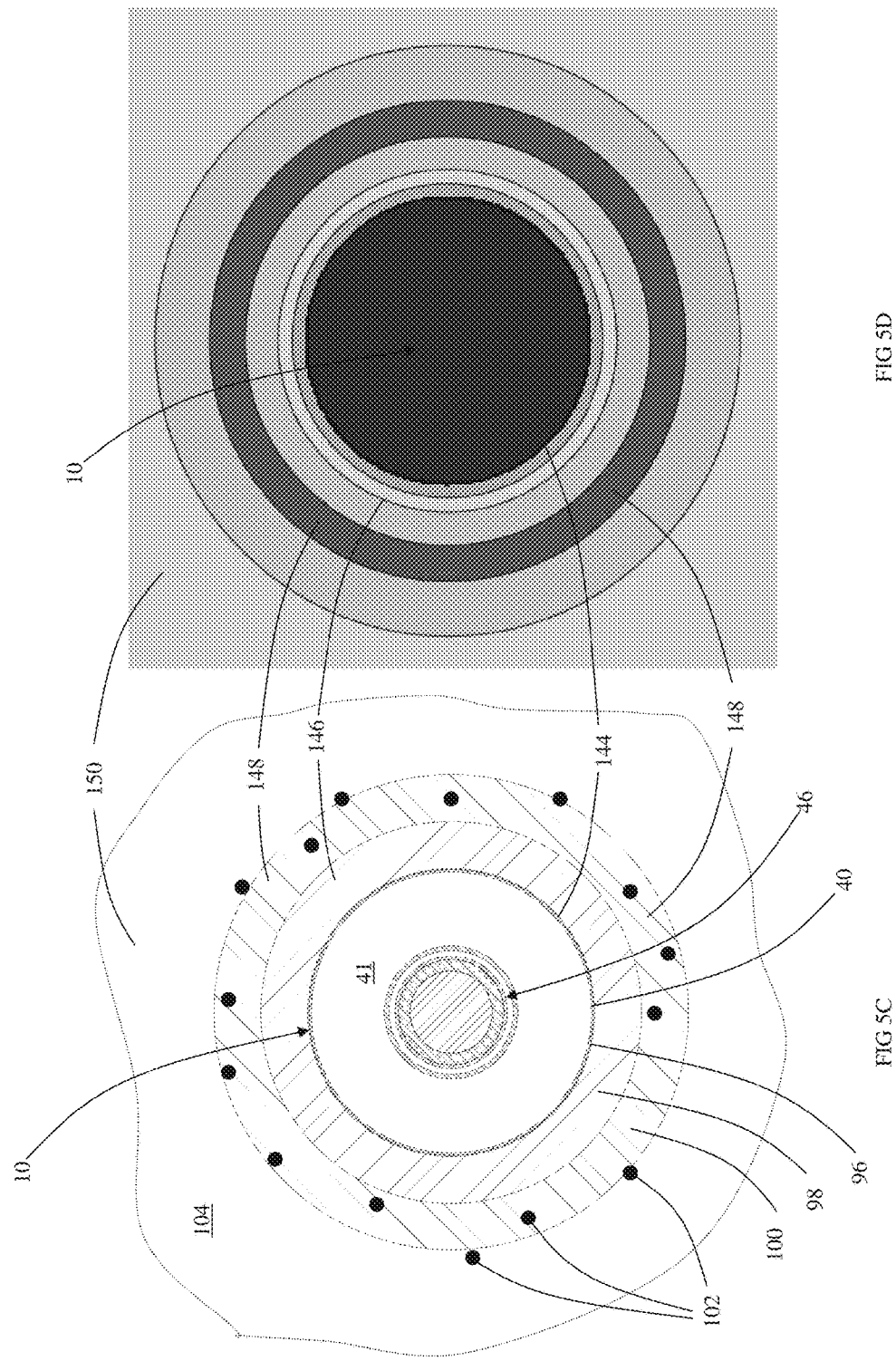

| Device O.D. | | Outer Tubing | | | Antenna Tubing | | | Spoke tubing | | | Configuration |
|---|---|---|---|---|---|---|---|---|---|---|---|
| mm | F | OD | ID | Wall | OD | ID | Wall | OD | ID | Wall | |
| 4.24 | 12.73 | 0.167 | 0.162 | 0.0025 | 0.102 | 0.098 | 0.002 | 0.029 | 0.025 | 0.002 | (1) x .102 + (14) x .029 |
| 5.36 | 16.08 | 0.211 | 0.204 | 0.0035 | 0.102 | 0.098 | 0.002 | 0.043 | 0.04 | 0.0015 | (1) x .102 + (10) x .043 |
| 6.76 | 20.27 | 0.266 | 0.258 | 0.004 | 0.102 | 0.098 | 0.002 | 0.076 | 0.073 | 0.0015 | (1) x .102 + (7) x .076 |
| 8.51 | 25.53 | 0.335 | 0.325 | 0.005 | 0.102 | 0.098 | 0.002 | 0.102 | 0.098 | 0.002 | (1) x .102 + (6) x .102 |

FIG. 7B

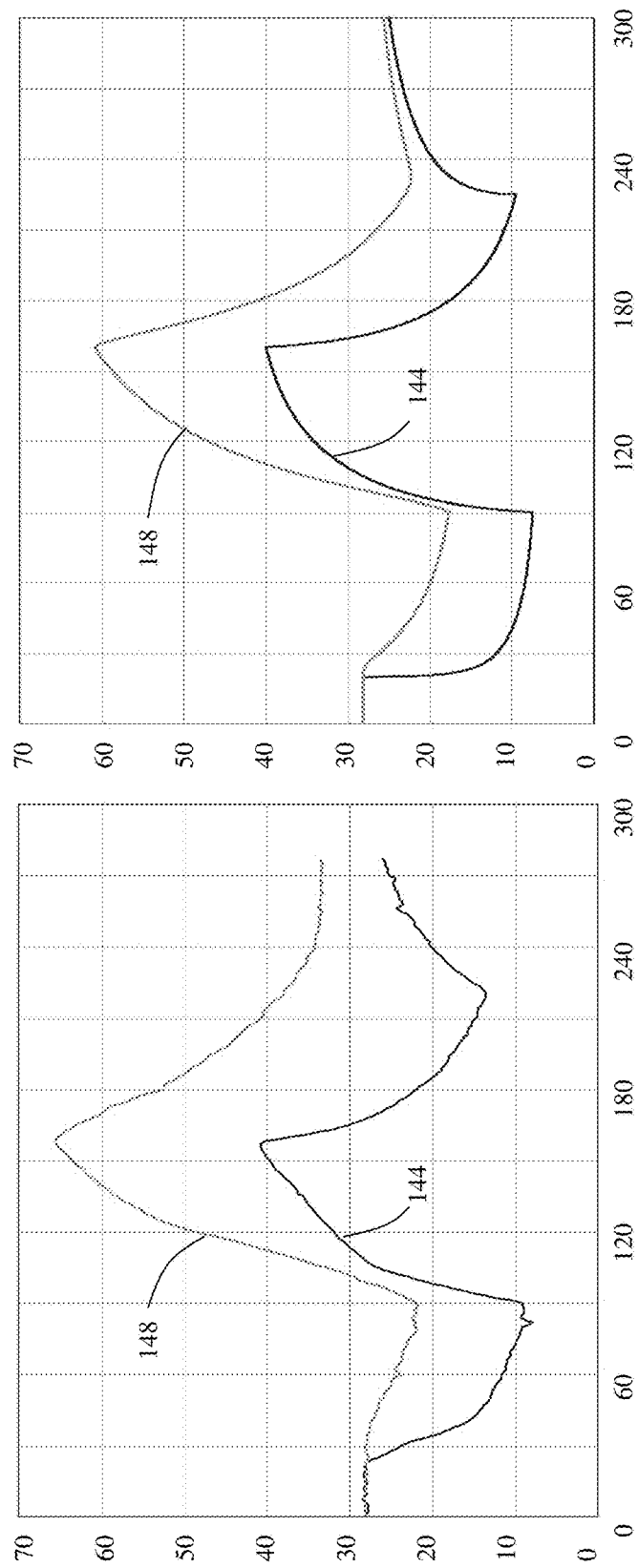

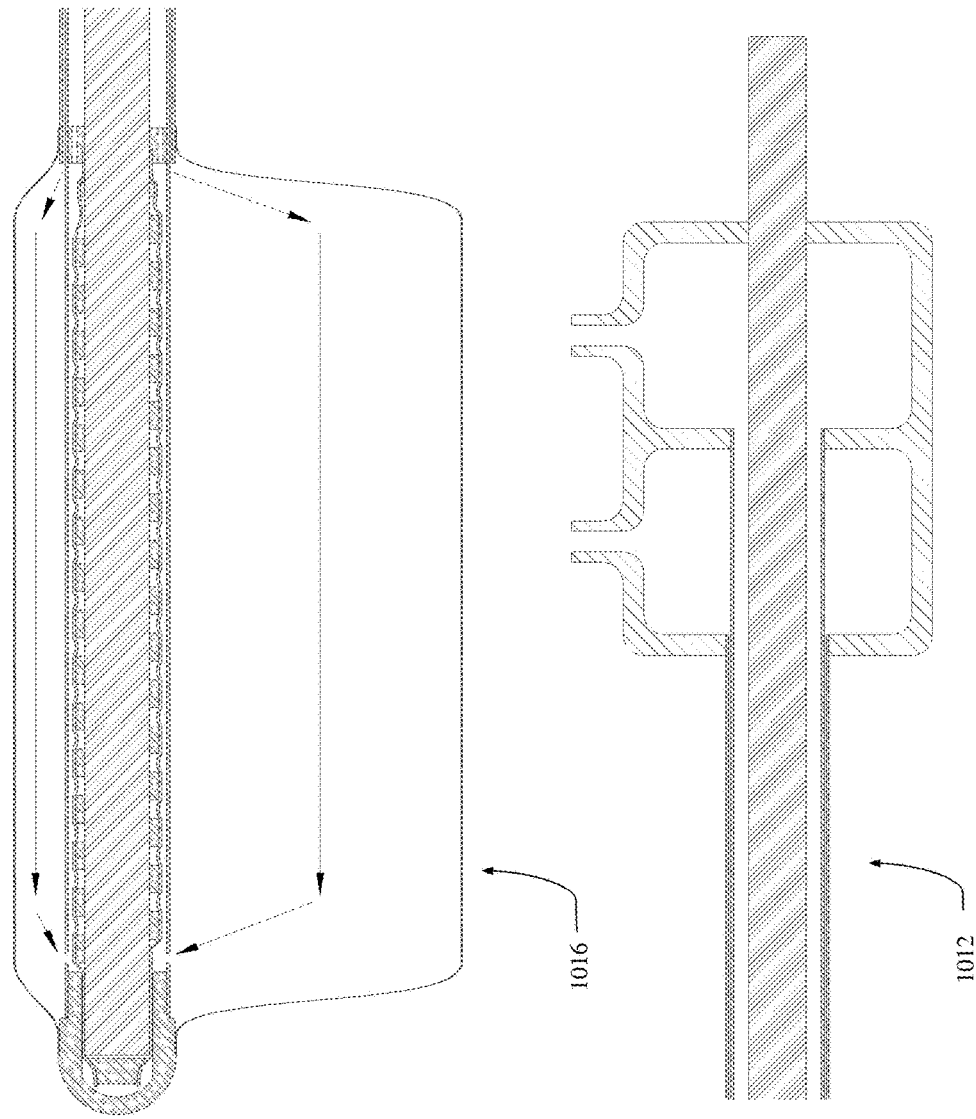

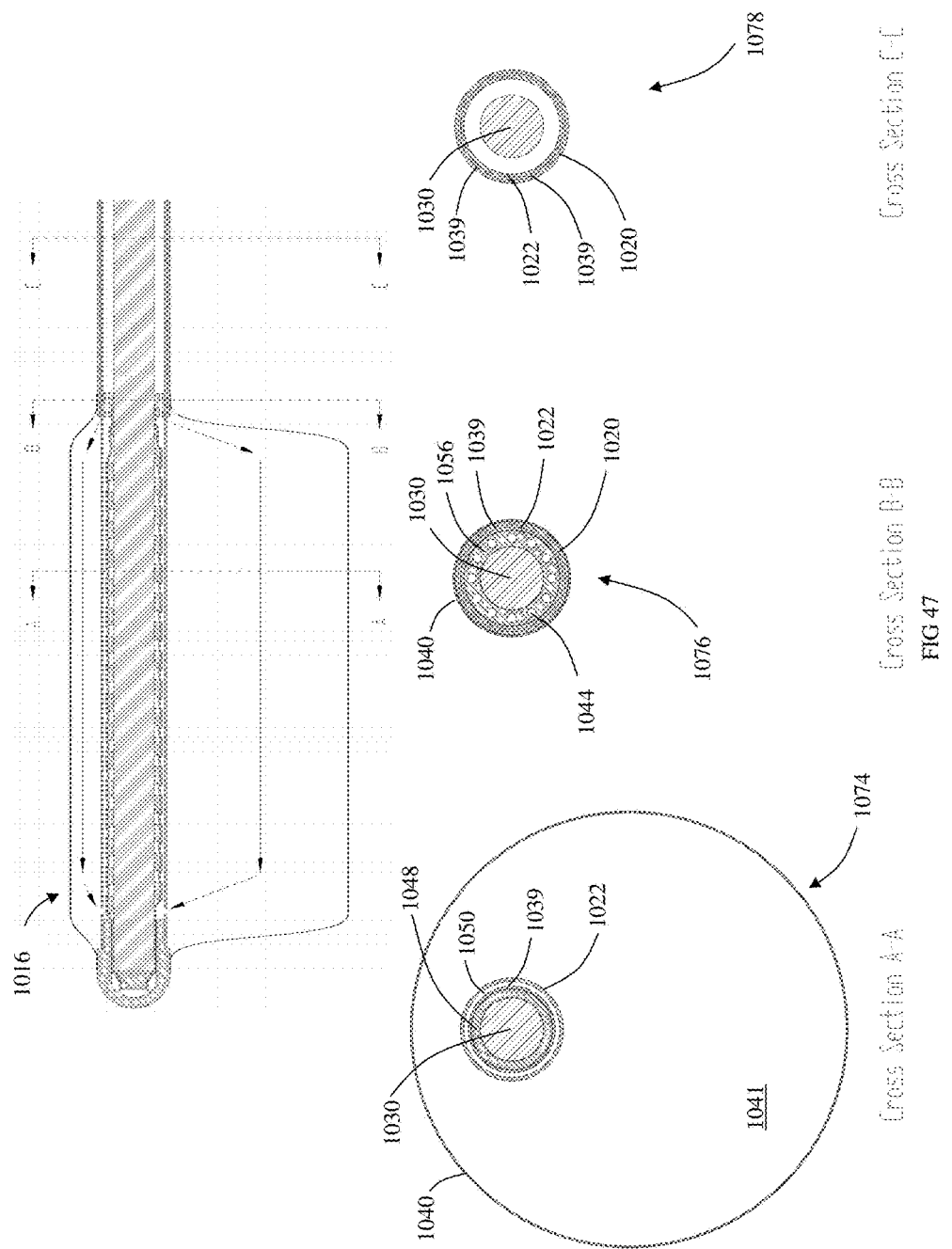

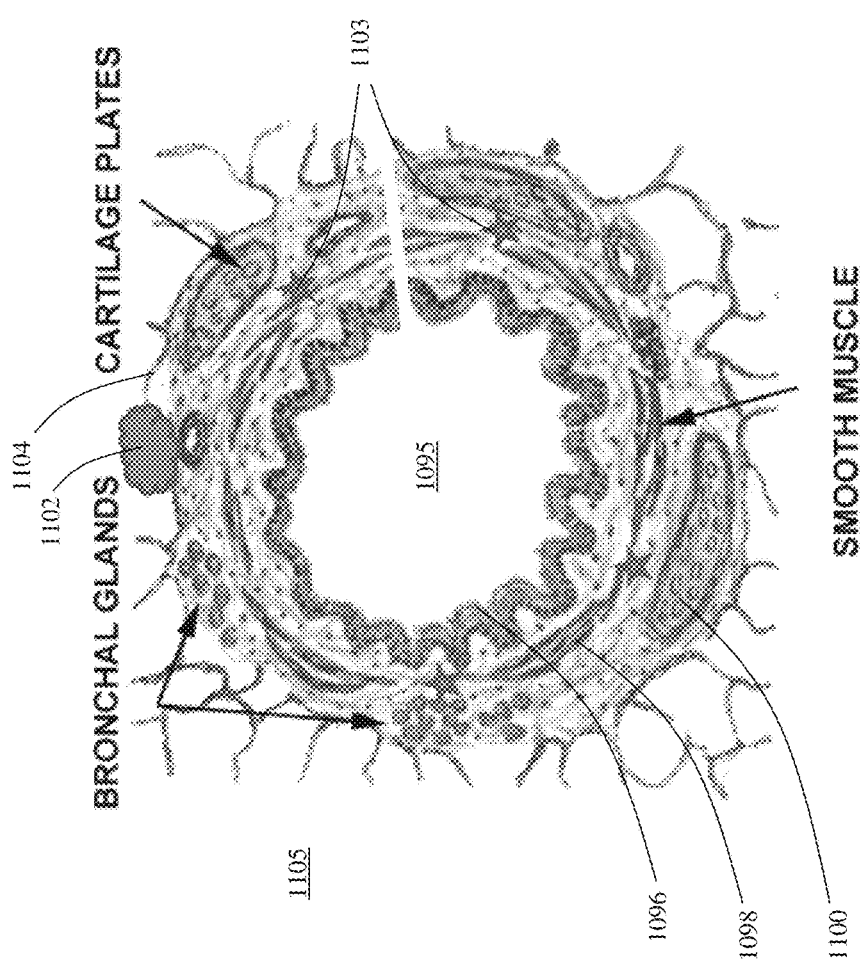

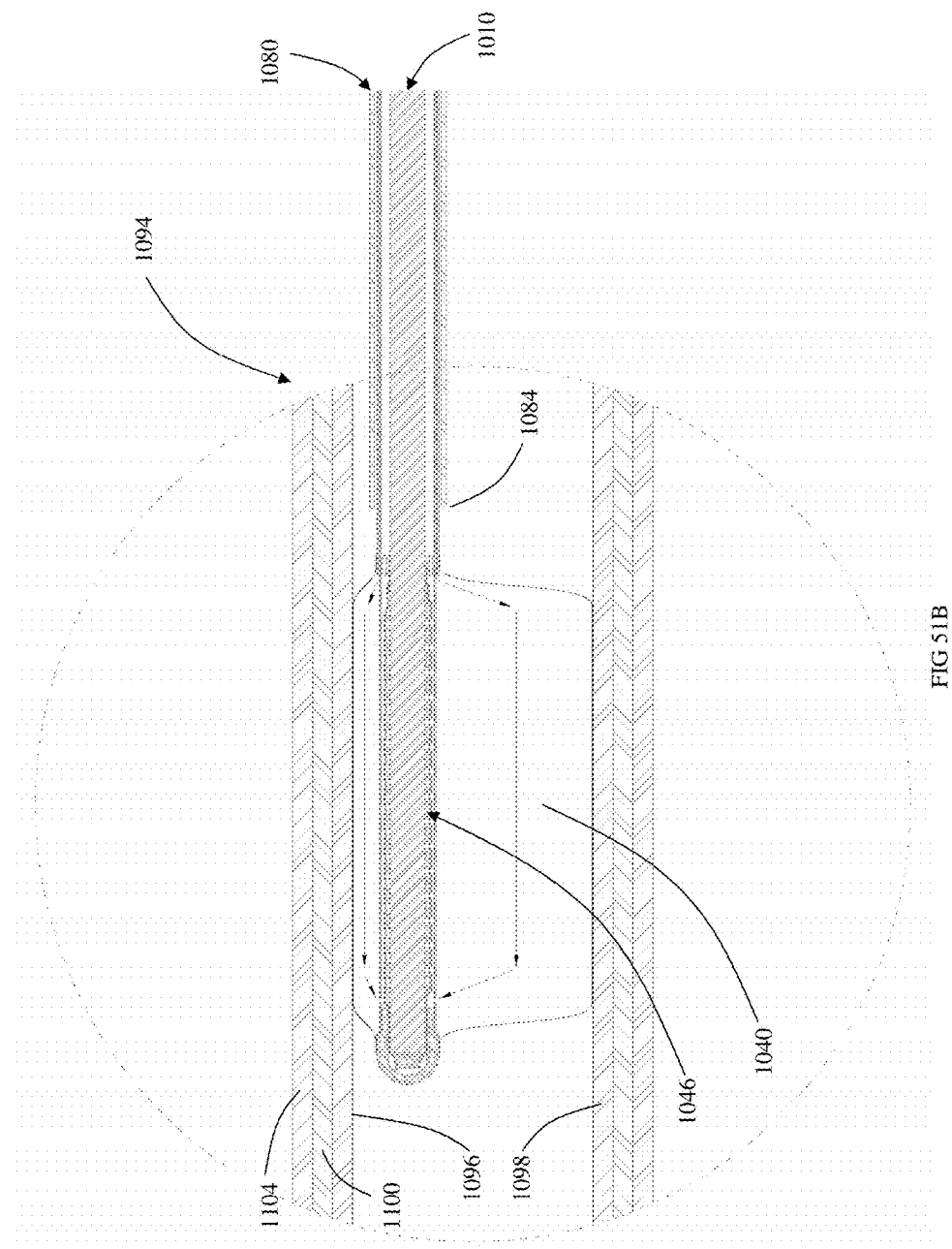

COOLED MICROWAVE DENERVATION

CROSS-REFERENCE TO RELATED APPLICATION(S)

This application is a division of U.S. application Ser. No. 14/032,013 entitled COOLED MICROWAVE DENERVATION filed Sep. 19, 2013 by E. Rudie (now U.S. Pat. No. 9,333,035), which in turn claims the benefit of U.S. Provisional Application No. 61/703,101 entitled COOLED MICROWAVE RENAL DENERVATION filed Sep. 19, 2012 by E. Rudie, and also claims the benefit of U.S. Provisional Application No. 61/734,419 entitled COOLED MICROWAVE PULMONARY DENERVATION filed Dec. 7, 2012 by E. Rudie.

INCORPORATION BY REFERENCE

The aforementioned U.S. application Ser. No. 14/032,013 and U.S. Provisional Application Nos. 61/703,101 and 61/734,419 are hereby incorporated by reference in their entirety.

BACKGROUND

The present invention relates to denervation, and more particularly to a system and method for performing denervation using a cooled microwave catheter introduced into a neighboring body lumen such as an artery.

Medical research has revealed that a number of problematic human conditions can be treated by damaging certain nerves or groups of nerves, which is generally referred to as denervation. One example of a denervation procedure that has been found to produce beneficial effects is renal denervation. It has been demonstrated in many subjects that surgical renal denervation by renal artery transection and re-anastomosis is effective in reducing noradrenaline content in the kidney and favorably impacts blood pressure in resistant hypertension patients. This has led to less invasive, percutaneous approaches that use RF energy to create focal ablation lesions in each renal artery. These approaches have been demonstrated clinically to be an improvement over surgical renal denervation but they still have several drawbacks. Existing RF based approaches will damage the intima and media of the artery. In some approaches, several lesions must be created in each renal artery, such as up to six lesions in each renal artery for a total of twelve lesions per patient, and due to the intimal and medial damage, must be created with some longitudinal separation to avoid damage to the artery that could lead to aneurism or possible rupture. If created individually, each lesion takes about two minutes to create and is performed under fluoroscopic guidance. It is relatively easy to identify where the ablation device is positioned along the length of the artery, but it is significantly more difficult to know where the ablation device is positioned within the circumference of the artery. Accordingly, considerable variability is expected in the extent of the circumference for which the nerves have been ablated. Additionally, there is an opportunity to shorten procedure time. Devices are now emerging that create multiple ablations simultaneously but they still damage the intima and media.

Renal nerves do not merely travel parallel to the renal artery but, rather, twist around it. The discrete lesions must not be created at the same location along the length of the artery to completely block the renal nerve activity as that would result in unacceptable weakening of the artery and likely aneurism and possible rupture. It is therefore impossible to eliminate all nerve pathways by the discrete lesions.

Lesions created by an RF device damage the entire thickness of the artery, including the intima, media, and adventitia. Even with the translation described above, angiographic images of the renal artery following an RF ablation procedure demonstrate a lumpy appearance that is indicative of undesirable cellular and mechanical changes in the wall of the artery. Although this lumpy appearance has been reported to resolve, there have been anecdotal reports of aneurism. The present devices do not protect the media of the artery except possibly by passive cooling due to arterial blood flow.

Further, and of greater concern is that the damage to the artery intima creates a site for atherosclerosis to form over time and it is anticipated that significant sequelae or late effects will manifest 5 or more years from the date of treatment. There is no long term data on any of the percutaneous approaches so this limitation is not generally apparent today.

Another limitation of existing RF based devices that damage the media is that patients who may fail treatment are not candidates for retreatment. This is because there is unacceptable risk to creating an overlapping thermal injury to the media a second time.

Accordingly, there is a need for a percutaneous, transluminal device that addresses these limitations and can provide a complete circumferential thermal injury to consistently and completely destroy the problematic renal nerves without damaging the intima or media of the artery.

It has also been demonstrated that denervation of the nerve trunks running along the outside of the bronchus will "disconnect" airway smooth muscle and mucus producing glands from the central nervous system, resulting in relaxation of the airway smooth muscle and a reduction in mucus production. Accordingly, airway obstruction due to disease such as COPD and asthma is reduced. The present invention has the advantage of protecting the intervening bronchial tissue and not requiring the energy emitter to be electrically in contact with the tissue. An additional advantage is the potential for a shortened procedure time and easier procedure.

Cooled RF devices have been disclosed (US2012/0016363A1) that also seek to accomplish this. However, the RF electrode must be in electrical contact with tissue for this approach to work. This requires a more complex device to accomplish the necessary cooling and heating is dependent upon tissue impedance which varies dramatically between smooth muscle, cartilage and fat. In contrast, microwave heating is accomplished by a travelling electromagnetic field so that the antenna need not be in contact with tissue. A more simple balloon structure is appropriate and the field will travel through tissue of differing dielectric constants and effectively heat the target nerve bundle. In concert with cooling accomplished with good heat transfer from a simple thin walled balloon, the result is a temperature field that protects the mucosa, smooth muscle, glandular tissue and cartilage of the bronchus but controllably thermally ablates the targeted nerve bundle.

Accordingly, there is a need for a simple percutaneous, transluminal device that addresses these limitations and can provide a controlled thermal injury to consistently and completely destroy the problematic pulmonary nerves without damaging the mucosa, muscle or cartilage of the bronchus.

Microwave Technology

Catheters have been developed that combine microwave energy with a frequency of 915 MHz, 1296 MHz, 2450 MHz or another appropriate frequency with cooling for a variety of applications. In the medical context, microwave energy refers generally to frequencies of energy that cause heating of tissue via dielectric absorption. U.S. Pat. No. 5,300,099 (Rudie.) discloses a device to treat BPH in the prostate transuretherally without destroying the urethra. The clinical objective of this technology is to mimic the surgical resection (TURP) and thermally destroy as large a volume of prostate tissue as possible adjacent to a length of the urethra in a minimally invasive, office based procedure. This technology has been developed, FDA approved, and is available today.

Other examples of cooled microwave devices include U.S. Publication No. 2003/0065317 (Rudie et al.) intended to provide a lesion as large as possible for treating soft tissue like renal cell carcinoma or liver tumors. In this case, it is not necessary to protect the tissue adjacent the device. Instead, cooling is used to enable a significantly larger thermal injury than an uncooled device by preserving the dielectric constant of the tissue adjacent the device and preventing undesirable cavitation that would occur with a non-cooled device.

A cooled microwave device has not been disclosed that optimizes the geometry, three dimensional SAR distribution, excitation frequency, heat transfer coefficient, necessary safety mitigations, and therapy control algorithm for targeting of nerves without damage to the mechanically important tissue forming or adjacent to the wall of the body lumen in which the device is inserted, such as media and intima tissue of an artery in some examples.

An antenna of the type disclosed in U.S. Pat. No. 5,300, 099 is particularly advantageous as it does not result in transmission line radiation. The antenna described in U.S. Pat. No. 5,300,099 is optimized for creating a large volume of thermal injury suitable for treating a prostate or cancerous tumor in kidney or liver, for example. However, this antenna may be further adapted to be ideal for treating nerves by adaptations such as modification of antenna tuning/pitch to create a single smaller zone of SAR, adjusting the antenna pitch to create two small and separate zones of high SAR or separating the antenna coil from the coaxial cable to allow coolant flow to return within the antenna. In the case of the former, it is possible to adjust the antenna's coil pitch/tuning/catheter loading such that essentially all the significant specific absorption rate (SAR) field comes from one of the elements, thereby shortening the treatment length to make the 3D SAR more optimal for performing denervation. In addition to shortening the length of thermal injury along the body lumen (such as an artery), the radiation pattern will more closely resemble a point source, and causes the field to drop off more rapidly than would otherwise occur, allowing targeting of tissue closer to the device. In the case of the middle, the antenna may also be optimized by non-uniform coil pitch to produce two narrow SAR peaks that can create two separate circumferential zones of thermal injury and considerably lessen the likelihood that injured nerves might regenerate and result in loss of efficacy longer term. The adaptation described in the latter may be applied to either former or middle adaptations.

Other alternate antenna embodiments are possible to produce, for example, a single narrow SAR field. These embodiments would not be optimal for creating a large zone of necrosis for treating a length of tissue, such as a prostate. An antenna that produces a single relatively narrow SAR in the center of the antenna may be particularly suitable for denervation, such as renal or bronchial denervation for example. Such an antenna is not as suitable for treating a length of tissue, such as desired in the prostate, but can produce a radiation pattern that is suitably shortened or similar to a point source.

The length of cooling protection in a microwave antenna-carrying catheter can be shortened as desired to reduce the depth of cooling protection due to fringing field effects. Alternately, the length of cooling protection may be longer than the radiation length from the microwave antenna as it is in the embodiments described below. Antenna length can also be shortened to reduce penetration, also due to fringing effects. As mentioned previously, the dipole may be made asymmetric such that only one element contributes meaningful SAR (likely the non-driven side). Alternate antenna embodiments are disclosed in more detail below.

BRIEF DESCRIPTION OF THE DRAWINGS

FIGS. 1A-1F are diagrams illustrating a microwave antenna-carrying catheter according to an embodiment of the present invention.

FIG. 2 is a detailed view of a microwave antenna-carrying catheter that includes cross sectional details.

FIGS. 4A and 4B depicts a renal artery guide catheter with and without the microwave carrying catheter placed within it.

FIGS. 4C and 4D are more detailed diagrams of the distal and proximal regions of the guide catheter with microwave antenna carrying catheter placed within it.

FIG. 5C is a detailed cross sectional view of the microwave antenna carrying catheter placed within the renal artery.

FIG. 5D is a cross sectional contour plot of the temperature field produced by microwave carrying catheter placed within the renal artery as in FIG. 5C.

FIG. 7B is a table of tubing sizes used in the device of FIG. 7A.

FIG. 14B is a graph illustrating specific temperature data obtained in a region of the right renal artery during the porcine study shown in FIGS. 12 and 13.

FIG. 14C is a graph illustrating a computer simulation of the specific temperature data plotted in FIG. 14B.

FIGS. 46A-46F are diagrams illustrating a microwave antenna-carrying catheter according to another embodiment of the present invention.

FIG. 47 is a detailed view of the microwave antenna-carrying catheter of FIGS. 46A-46F that includes cross sectional details.

FIG. 50 is a cross section of a primary bronchus just beyond the carina of the trachea.

FIG. 51B is a detailed cross sectional view of the microwave antenna carrying catheter placed within a bronchus.

DETAILED DESCRIPTION

The concepts and principles of the present disclosure provide devices and methods for inserting a catheter in a body lumen to create a lesion in tissue where targeted nerves are located, while preserving tissue adjacent to and forming the wall of the body lumen. In some embodiments, the lesion that is created may be circumferential in shape, meaning that the lesion is generally (although typically not precisely) donut-shaped surrounding the renal artery (or other body lumen in which the catheter is inserted). According to one example of such a concept associated with the present invention, a device and method are provided to create a lesion in the adventitia and/or immediate adjacent surrounding tissue of a renal artery, so that the renal nerves located in the adventitia and/or immediate adjacent surrounding tissue are thermally damaged, while protecting the intima and media of the renal artery from injury. This approach is designed to more completely transect the renal nerves and achieve therapeutic effects with similar or greater efficacy to those that have been seen and reported by systems utilizing RF ablation to damage the renal nerves, without the damage to the renal artery and the inconvenience of manual manipulation of the RF ablation device. This is a significant advantage as it prevents the potential for atherosclerosis formation, allows retreatment of the artery if needed, and does not impact the mechanical integrity of the artery or its elasticity. An additional advantage is a shortened procedure time and easier procedure without the need for multiple burns and manipulations.

Much of the following disclosure is directed to an embodiment for performing renal denervation. It should be understood that many of the concepts and principles described with respect to a renal denervation embodiment are applicable to denervation procedures for other parts and locations of the human body.

Figure 1A:
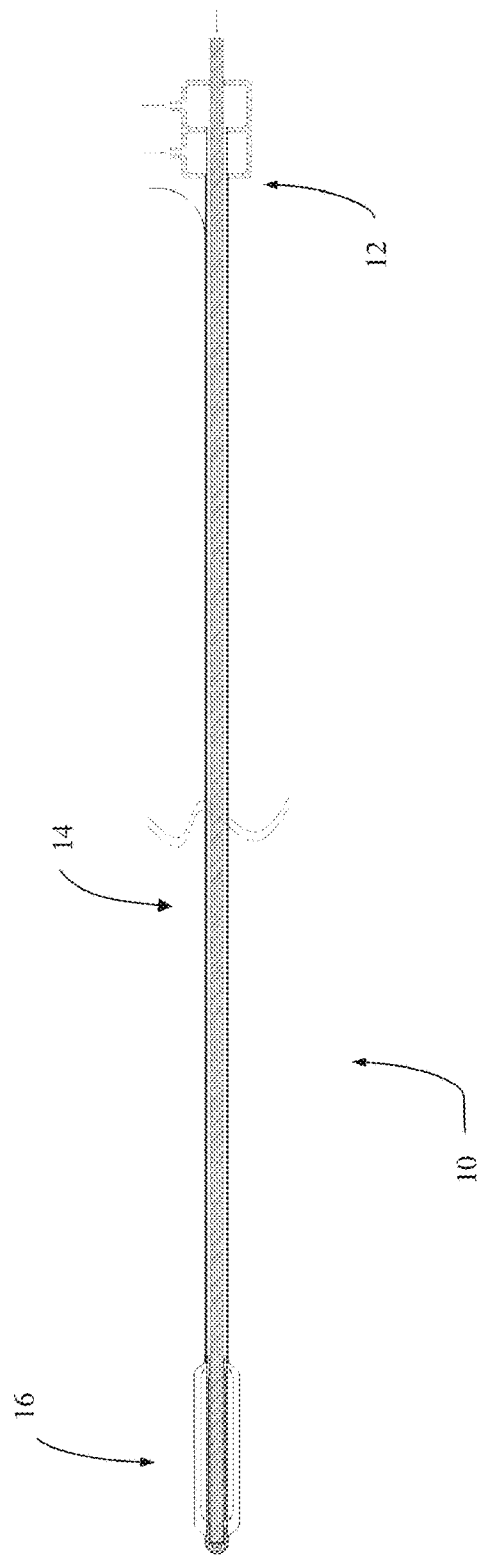
Figure 1B:
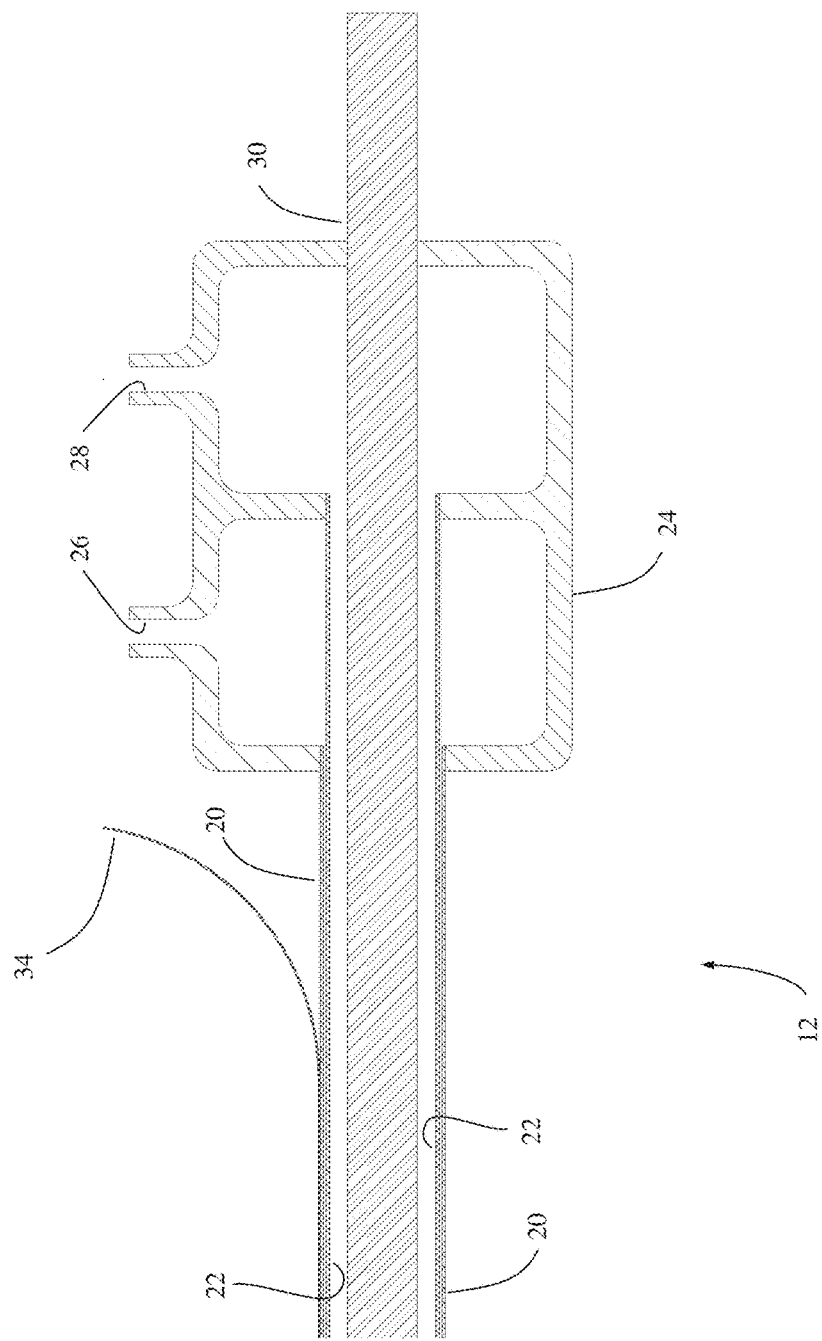

FIGS. 1A-1E are diagrams illustrating microwave antenna-carrying catheter 10 according to an embodiment of the present invention. As shown in FIG. 1A, catheter 10 includes proximal portion 12, middle portion 14, and distal portion 16. FIG. 1B is an enlarged view of proximal portion 12 of catheter 10. Catheter 10 includes outer body wall 20 and inner body wall 22, between which a space is defined for the flow of coolant. At proximal portion 12 of catheter 10, coolant intake/exhaust structure 24 is provided, with walls configured to provide a coolant input port 26 that communicates with the space between outer body wall 20 and inner body wall 22 of catheter 10, and also to provide a coolant output port 28 that communicates with an interior of catheter 10 formed by coaxial cable 30 and the inside inner body wall 22. Coaxial cable 30 is provided to the interior of catheter 10 inside inner body wall 22, is coupled to a microwave antenna 46 (FIG. 1D) at distal portion 16 (FIG. 1A) of catheter 10, and is coupled to a microwave generator (not shown) to supply power to the microwave antenna via coaxial cable 30.

Figure 1C:
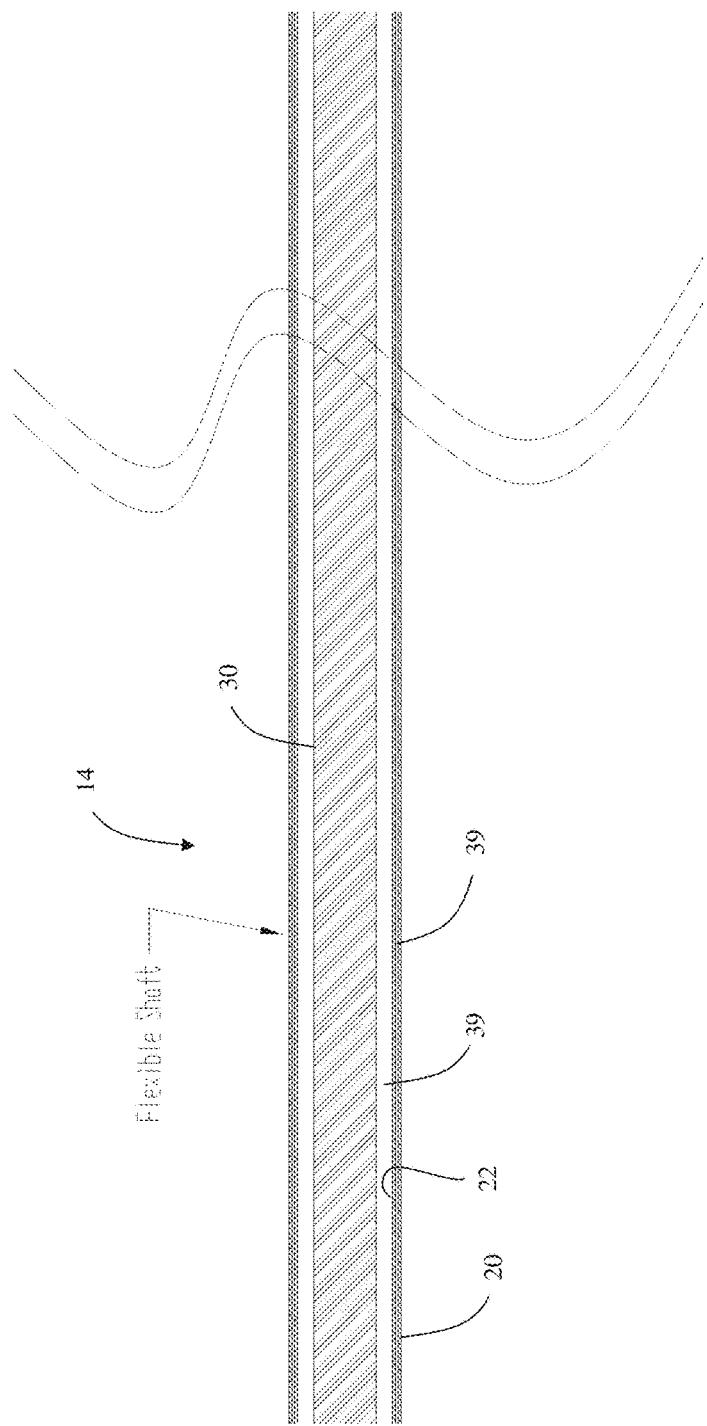

FIG. 1C is an enlarged view of middle portion 14 of catheter 10, showing outer body wall 20, inner body wall 22, coaxial cable 30, and interior region for coolant to flow within catheter body walls 39. These components make up the flexible shaft of catheter 10 that is able to be guided into the renal artery of a patient via a femoral artery, for example. The length is suitable to conveniently be inserted into the femoral artery and reach the renal artery or may be adjusted to accommodate other insertion locations such as the subclavian or common carotid arteries.

Figure 1D:
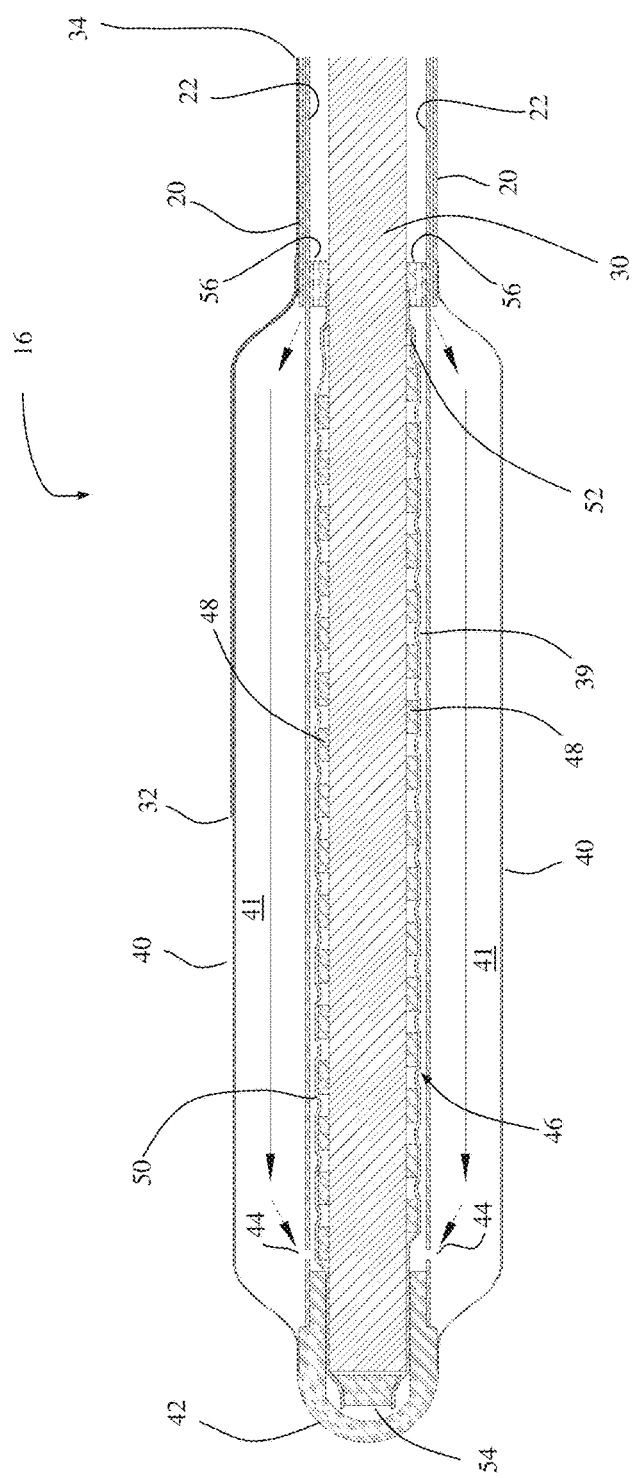

FIG. 1D is an enlarged view of distal portion 16 of catheter 10. As shown in FIG. 1D, balloon 40 is attached to outer body wall 20 of catheter 10 to form interior region 41 for cooling fluid to inflate balloon 40. Cooling fluid pressure is responsible for inflation of the balloon and may be controlled by an external pressure regulator (not shown) incorporated into the tubing or control console connected to catheter 10. Balloon 40 is attached to tip 42 at a distal end of distal portion 16 of catheter 10. Balloon 40 may be fabricated of compliant material, non-compliant material, or material that blends these characteristics. Return ports 44 are provided in inner body wall 22 of catheter 10 to allow cooling fluid to exit balloon 40 and flow in a return path toward proximal portion 12 (FIG. 1B) of catheter 10, in the space between inner body wall 22 and microwave antenna 46. Additional ports are provided in coaxial cable spacer 56 so that coolant may continue to flow in a return path toward the proximal portion 12 (FIG. 1B) of catheter 10 in the space formed between the inner body wall 22 and coaxial cable 30. Microwave antenna 46 is coupled to coaxial cable 30 at distal portion 16 of catheter 10, with windings 48 configured to form a microwave radiator. Thin wall shrink tubing 50 is placed around antenna 46 to isolate it from coolant flowing within space 39. Additional details of various antenna embodiments are depicted in FIGS. 28, 29, 32, 34 and 36. A temperature sensor 32 is positioned on the surface of balloon 40 to monitor the temperature of the intima 96 during the treatment. The temperature reading may be used to control treatment parameters and/or to ensure safety.

FIG. 1E depicts an embodiment of catheter 10 without a temperature sensor 32. For some treatment algorithms this sensor is not necessary and it simplifies catheter 10 and also eliminates the possibility of non-uniform heat transfer between intima 96 of renal artery 94 and coolant within balloon 41.

Figure 1F:
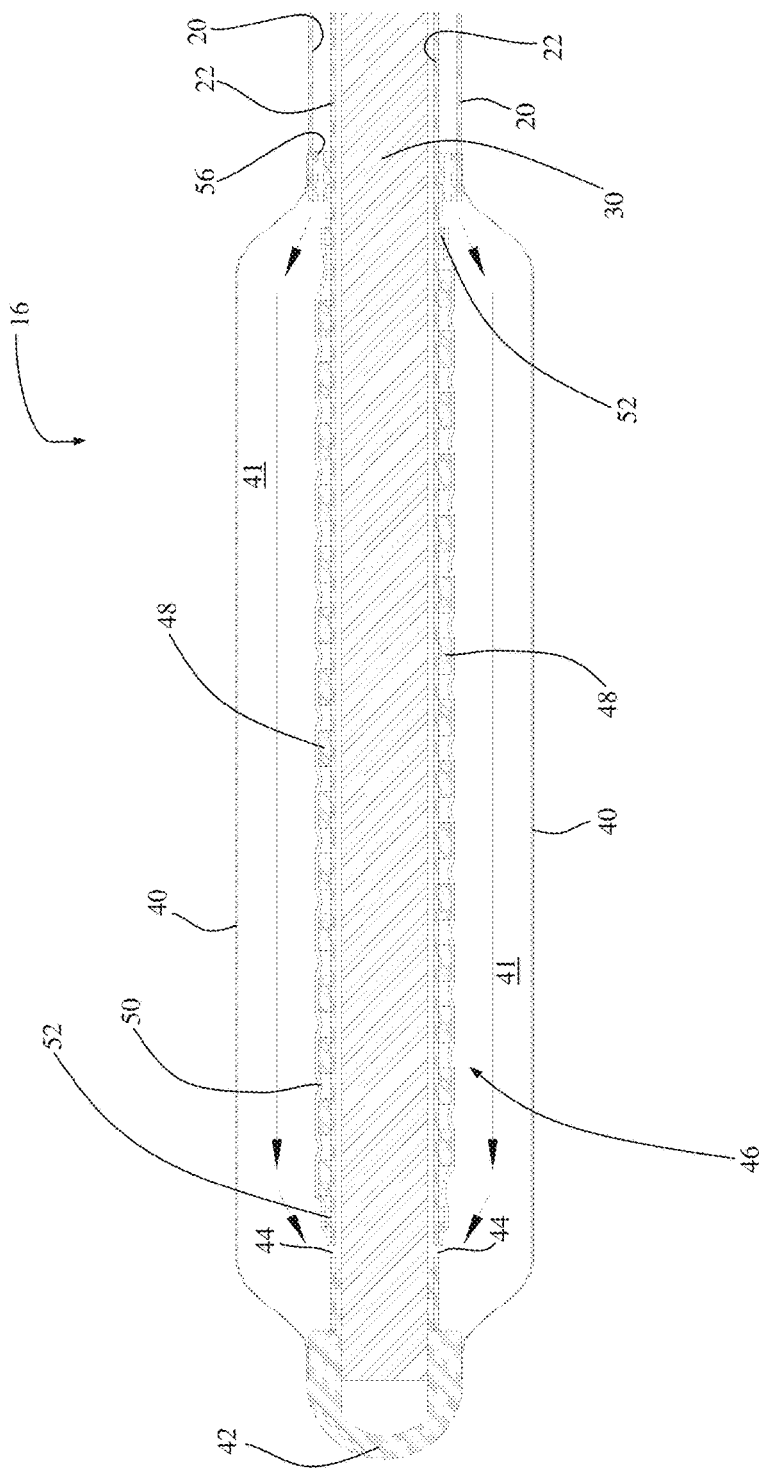
Figure 36:
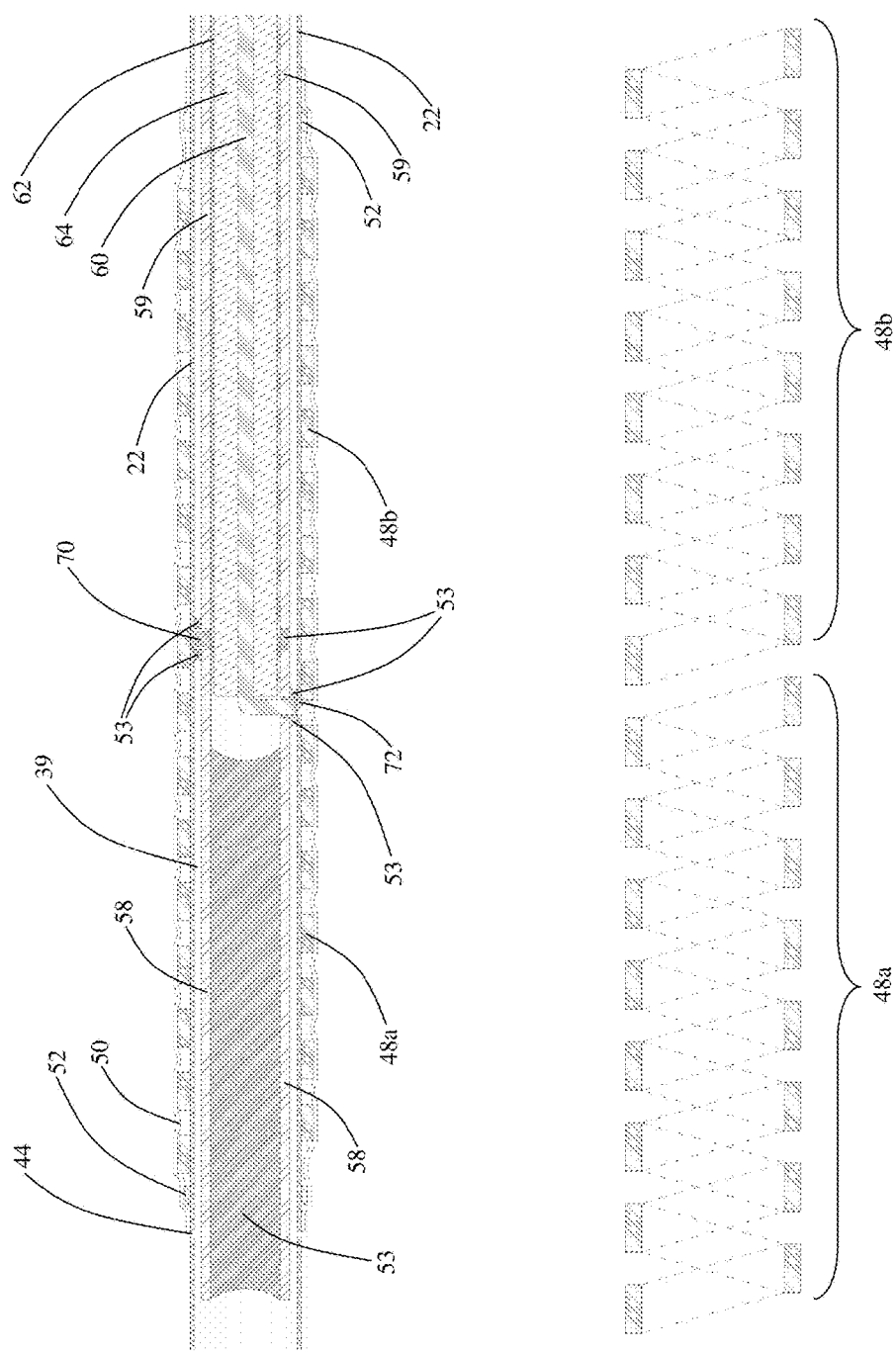
FIG. 36 is a diagram of another antenna embodiment wherein the antenna coil is configured to be placed within the cooling balloon rather than within the catheter body wall.

FIG. 1F depicts an embodiment of catheter 10 that locates antenna coil 48 within balloon 40 rather than within the catheter body wall. Coolant flows between inner body wall 22 and outer body wall 20, through spacer 56, and into interior region 41 formed by balloon 40 as before. However, antenna coil 48 is placed within this region as well, separated only by shrink tubing 50 from coolant within 41. Coolant then flows through ports 44 as before but in this embodiment coolant will flow between coaxial cable jacket 30 and inner body wall 22 within the antenna. Specific antenna adaptations to permit this flow of coolant and seal coolant from interior regions of coaxial cable 30 are depicted in FIG. 36 and described below.

FIG. 2 is a diagram of more details of distal portion 16 of catheter 10 including cross sectional views of the balloon 40, of the coaxial cable spacer 56, and of the shaft of catheter 10. Cross section 74 corresponds to section A-A and includes balloon 40, region 41 for coolant to flow inside balloon 40, coaxial cable 30, antenna coil 48, antenna shrink tubing 50, and a region 39 within which coolant flows between the antenna and inner body wall 22. The outer body wall 20 does not extend into balloon 40 beyond spacer 56. Cross section 76 corresponds to section B-B and includes coaxial cable spacer 56 containing ports 44 for coolant to flow in the return path, inner body wall 22, outer body wall 20, an inner region 39 for coolant to flow, and balloon 40 bonded to outer body wall 20. Cross section 78 corresponds to section C-C and includes coaxial cable 30, inner body wall 22, outer body wall 20, and regions 39 for coolant to flow within the catheter body walls 20 and 22.

Computer Simulation of Operation of Microwave Catheter for Renal Denervation

A computer simulation of operation of a microwave catheter for renal denervation was performed to illustrate the temperature profile that could be expected to be achieved. The simulation was configured with the following parameters and assumptions:

Published thermal physical properties were used for artery, fat, blood and nerves Published complex dielectric properties (conductivity, permittivity) were used for artery and fat Published data was used for anatomical structure (7 mm diameter renal artery) and nerve location Microwave emitter geometry, specific absorption rate (SAR) field and heat transfer coefficient were modeled The simulation space begins at the catheter/renal artery wall interface, and is modeled as a 1-dimensional model and can be extended to 2 dimensions because of symmetry.

The thermal simulation was performed based upon the Penne's Bioheat equation first published in 1948.

$$\rho_t c_t \frac{\partial T}{\partial t} = div(k\ gradT) - \omega \rho_b c_b (T - T_a) + Q + Q_m$$

This equation is an energy balance that simply states the sum of conductive heat flow minus convective heat due to blood flow plus heat generation from an external source (microwave) plus metabolic heating gives rise to temperature elevation. In practice, the metabolic component $Q_m \ll Q$ and can be neglected.

Figure 3A:
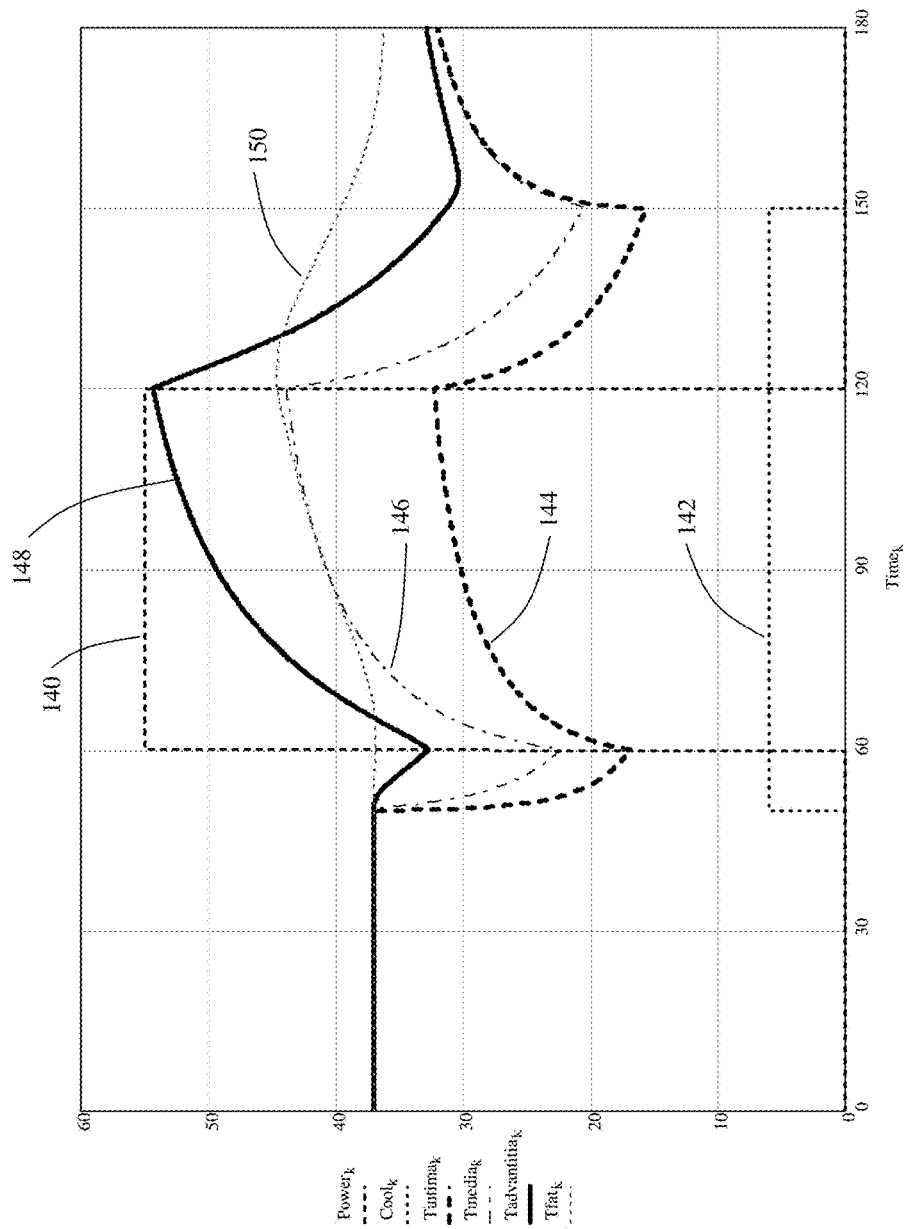
FIGS. 3A-3C are graphs that illustrate a temperature profile achieved by a computer simulation of the operation of a microwave catheter for renal denervation as a function of time (3A) and position (3B and 3C).

An iterative solution to this equation was implemented and run in the computer simulation. The computational space is assumed to be a 7 mm diameter (3.5 mm radius) artery, 2 mm thick surrounded by fat. A microwave term was incorporated based upon measured SAR data for the antenna described in U.S. Pat. No. 5,300,099 but modified to account for the different dielectric constants of artery and fat. Published values used for dielectric constants of artery and far are:

Published thermophysical properties for artery, fat, and blood were used and are given as:
tk1=0.476 for artery
tk3=0.209 for fat; Holmes et. al. (tissue radius>OD artery)
rocartery=3.9e+6 for artery
rocb1=3.9e+6 for blood
rocfat=3.2e+6 for fat
perf1=0.003 for in-vivo simulations, 0.0 for phantom The dielectric constant of porcine artery and surrounding fat was measured using an HP 85070 probe, HP 8753D network analyzer and associated dielectric probe software. The measured values were used to compute the wave equation and resulting form of the SAR term. The measured dielectric values at the operating frequency of 915 MHz are:
i. e'=51.7 for artery
ii. e"=18.0 for artery
iii. e'=12.9 for fat
iv. e"=4.13 for fat FIG. 3A is a graph of a representative simulation as described above as a function of time. In this simulation, coolant flow at a temperature of 6° C. (142) is initiated 10 seconds prior to initiating microwave power (140) at a constant 55 Watts for 60 seconds. Following the discontinuation of microwave power (140), coolant flow 142 is maintained at 6° C. for 30 seconds. Simulated temperatures corresponding to intima (144), media (146), adventitia (148) and surrounding fat (150) are plotted. Thermal injury depends on the entire thermal history (time & temperature) and depends upon the specific tissue. However, it can be appreciated that this simulation depicts a greater than 20° C. temperature difference between the target tissue 148 (nerves within the adventitia and immediate surrounding tissue) and the intima 144.

Figure 3B:
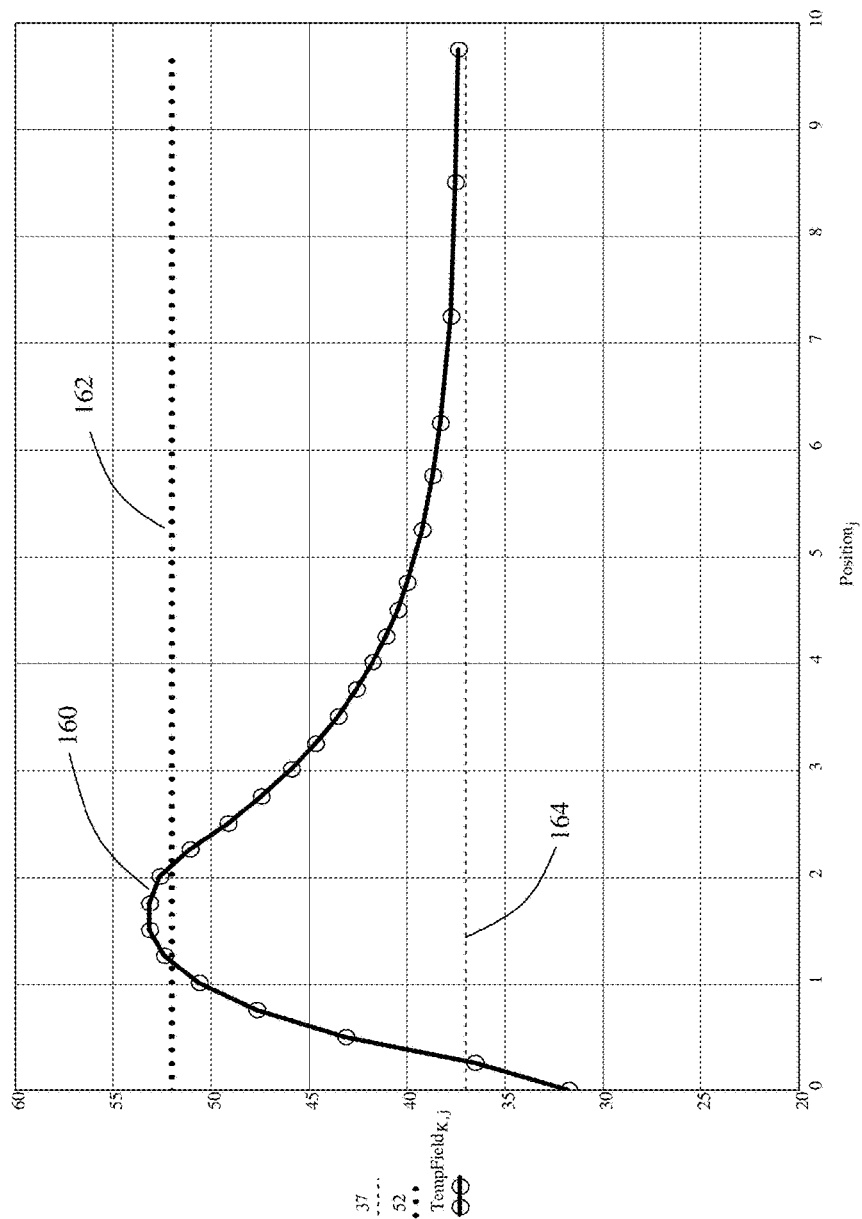

FIG. 3B is a graph illustrating the temperature profile achieved by the computer simulation described above and plotted as a function of time in FIG. 3A at a specific time so that the temperature distribution as a function of distance from the intima may be visualized. Tissue temperature 160 is plotted against position in units of mm so that it can be clearly seen that the maximum temperature (of about 53° C.) occurs at a distance of about 1.5 mm-2.0 mm (e.g., 1.6 mm) from the intima, which is the location of the target nerves for renal denervation, while the temperature within 0.5 mm of the intima is held below about 40° C. and temperature of the intima is held between about 30° C. and 35° C. A representative thermal injury threshold for a sample treatment duration is depicted by line 162 and basal body temperature is indicated by line 164. For this simplified example, tissue located between about 1.2 mm and about 2.1 mm will be irreversibly thermally injured.

In some examples, the majority of renal nerves may be located in this 1.2-2.1 mm window where highest temperatures are achieved (in other examples, the renal nerves may be located further from the intima, such as up to 4.0 mm or further in some examples, so that a deeper extending window would be used). The very steep temperature gradient between the intima and the maximum temperature region allows renal nerves to be damaged sufficiently to effectively achieve renal denervation therapy, while protecting the intima and media of the renal artery wall from damage. Further, the decay in temperature beyond 2.1 mm is sufficient to ensure no damage to adjacent structures such as the renal vein or the vasovasorum. The specific area in which maximum temperatures are achieved, and the temperature values achieved, can be adjusted by adjusting parameters such as power provided to the microwave antenna as a function of time, coolant temperature as a function of time, microwave duration, volume of coolant provided around the microwave antenna, and others.

Figure 3C:
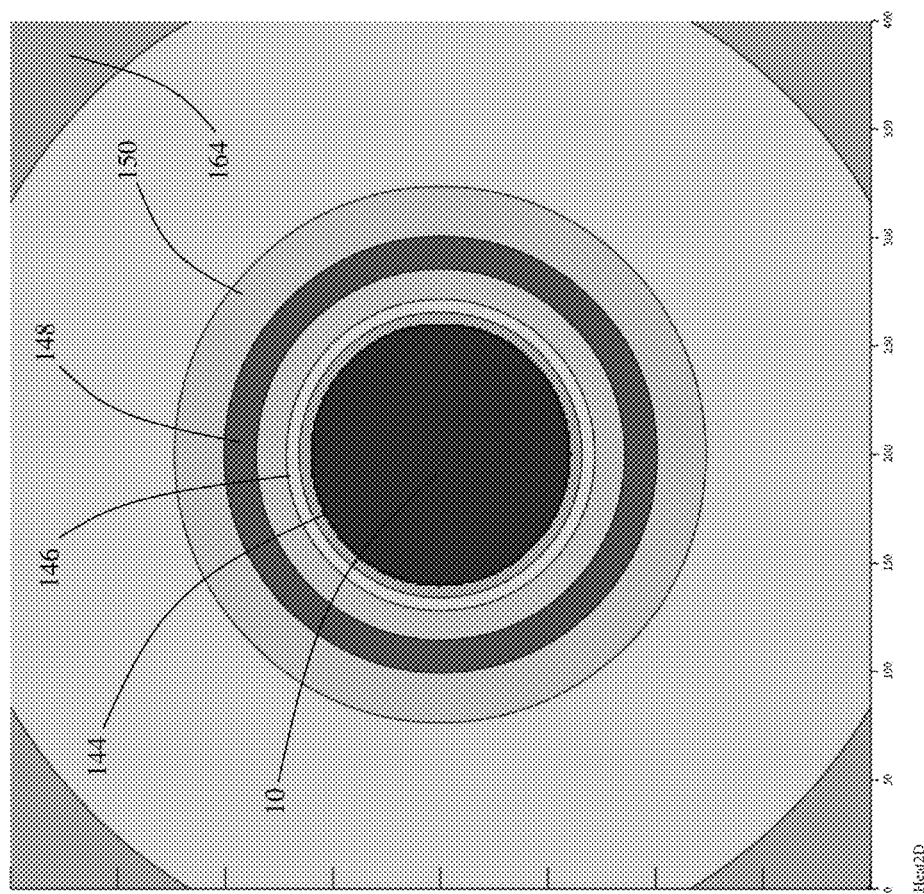

FIG. 3C depicts an extension of the 1-dimensional simulation to a 2-dimensional contour plot cross section within the treatment zone. In this plot the catheter 10 is placed in the middle and the first contour line represents intima temperature (144). The next contour line represents media temperature (146). The adventitia temperature (148) is the maximum temperature and is a dark red ring on the contour plot. This is the region of thermal injury. Beyond the adventitial temperature is the surrounding tissue temperature 150, largely fatty tissue, and beyond that is basal temperature 164.

FIG. 4A is a diagram of a commonly available renal artery guide catheter 80. It includes a tip 84, a central shaft 82, and a manifold 86.

FIG. 4B is a diagram of catheter 10 placed within guide catheter 80. Distal portion 16 of catheter 10 extends just beyond tip 84 when the proximal end 12 is conveniently close to manifold 86.

FIG. 4C is a diagram of the distal portion 16 of catheter 10 exiting guide catheter tip 84.

FIG. 4D is a diagram of the proximal portion 12 of catheter 10 entering manifold 86 of guide catheter 80.

Figure 5A:
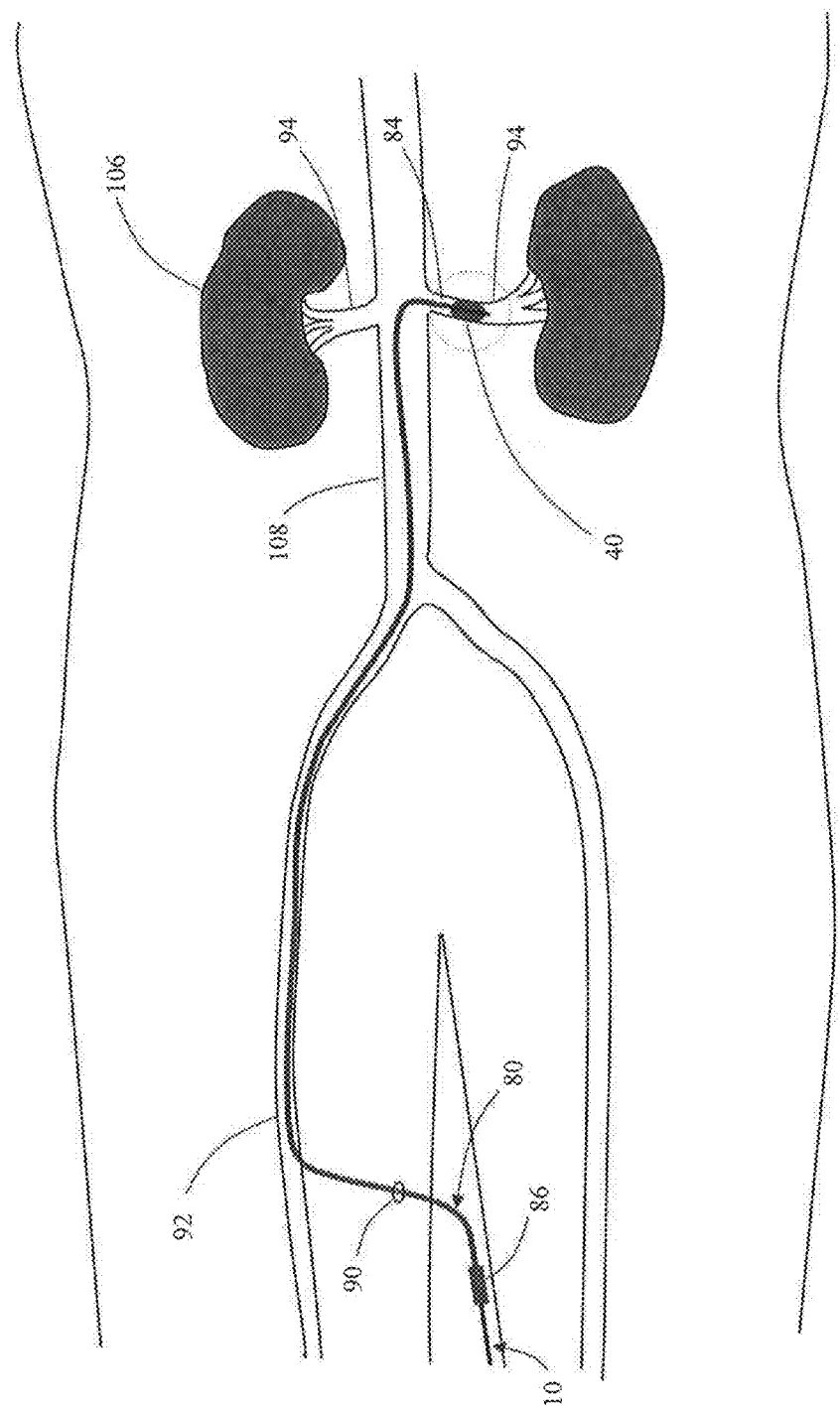
FIG. 5A is a diagram of the in-vivo placement of a guide catheter and microwave antenna carrying catheter to treat the renal nerves from within a renal artery.

FIG. 5A is a diagram of the in-vivo placement of catheter 10 using guide catheter 80 within a human body. In order to perform renal denervation therapy, guide catheter 80 is introduced into femoral artery 92 through access site 90 near the groin of a patient and advanced into the abdominal aorta 108 and into the renal artery 94 under CT guidance as known in the art. Microwave antenna carrying catheter 10 is introduced into guide catheter 80 by manifold 86 and advanced until deflated balloon 40 and microwave antenna 46 are fully extended beyond tip 84 of guide catheter 80 and positioned within the renal artery 94 in the region where renal nerves 102 are targeted for treatment. The position is confirmed by CT prior to initiating the treatment algorithm. Kidneys 106 are also shown.

Figure 5B:
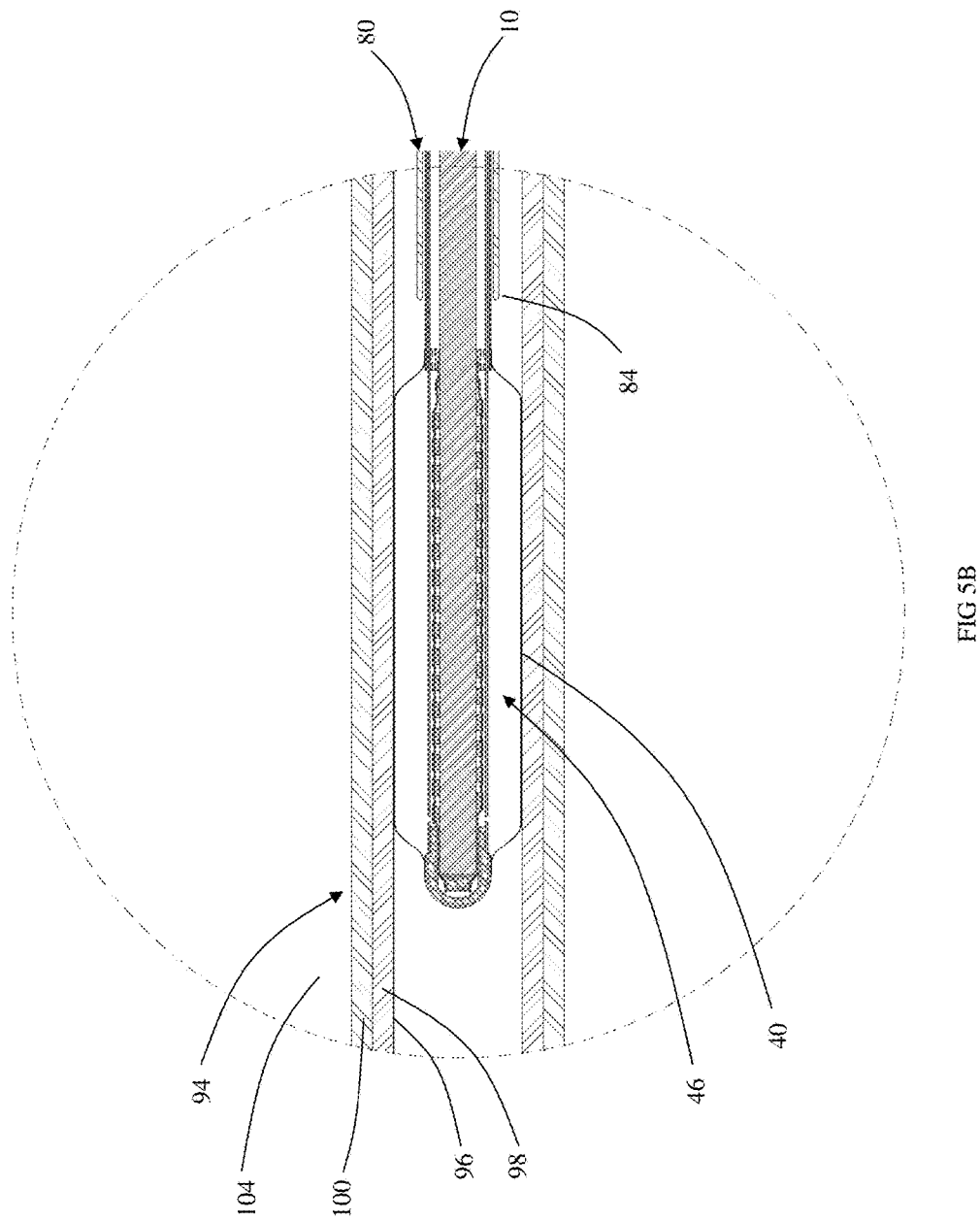
FIG. 5B is a detailed view of the microwave treatment catheter placed within the renal artery along the longitudinal axis.

FIG. 5B is an exploded diagram of the in-vivo placement of balloon 40 and antenna 46 within renal artery 94. Balloon 40 is inflated by circulating cooling fluid to contact intima 96 of renal artery 94. The media is depicted by 98, adventitia by 100, and surrounding tissue by 104. The renal nerves, 102 are not shown in this drawing but are contained within the adventitia 100 and the immediate adjacent surrounding tissue 104.

Once properly located, cooling fluid is circulated through the space 39 between outer body wall 20 and inner body wall 22 to interior region 41 of balloon 40, so that balloon 40 is inflated to be in contact with the wall of the renal artery. Proper inflation of balloon 40 may be confirmed by CT. Simultaneous with the circulation of chilled cooling fluid, microwave power is then initiated according to the treatment algorithm and is supplied by a microwave generator to coaxial cable 30, which feeds microwave antenna 46 and causes microwave energy to be emitted omnidirectionally at distal portion 16 of catheter 10 within renal artery 94. The microwave energy emitted by microwave antenna 46 causes tissue temperature to increase in the area surrounding microwave antenna 46, while cooling fluid circulating through balloon 40 cools the tissue immediately surrounding catheter 10. The net result is that the tissue immediately surrounding distal portion 16 of catheter 10 (such as the intima of the renal artery) is maintained at a temperature where thermal damage will not occur, while tissue surrounding distal portion 16 of catheter 10 that is spaced some distance from inflated balloon 40 (such as the advantitia of the renal artery where the renal nerves are located) is heated to a temperature sufficient to cause thermal damage to the tissue. This allows renal denervation to be performed without damaging the renal artery, in a single energization procedure that can cause the necessary thermal injury to the renal nerves in 30 to 120 seconds in some embodiments (although shorter or longer treatment times are desirable in other embodiments).

FIG. 5C is a diagram illustrating a cross section of catheter 10 placed in the renal artery of a patient during renal denervation. Microwave antenna 46 is shown in the center of the balloon 40 placed within renal artery 94. The intima 96 is in contact with balloon 40 such that heat transfer between intima 96 and the cooling fluid in the interior 41 of balloon may occur to keep intima 96 cooled and protected from thermal injury—this concept can be referred to as "thermal contact" between the cooling fluid and intima 96, through the wall of balloon 40. Media 98 immediately surrounds intima 96 and is cooled by heat transfer to intima 96. The adventitia 100, and immediately adjacent surrounding tissue 104, are the location of the renal nerves 102. More distant surrounding tissue 104 does not receive sufficient heat to cause thermal damage, nor does other tissue maintained close to basal temperature 150.

FIG. 5D is another simulation contour plot as described above for FIG. 3C but here it is scaled to match the size of the renal artery cross section so that the precise targeting of renal nerves by the temperature field can be appreciated. The maximum temperature contour lines 148 coincide with adventitia 100 and immediately adjacent surrounding tissue 104. This is the precise location of the renal nerves 102 as shown in FIG. 5C. It can also be appreciated that the intima temperature 144 and media temperature 146 are located on cooler contour lines and therefore do not experience thermal damage. Temperature at distant tissue 150 is maintained very near basal temperature.

Figure 6:
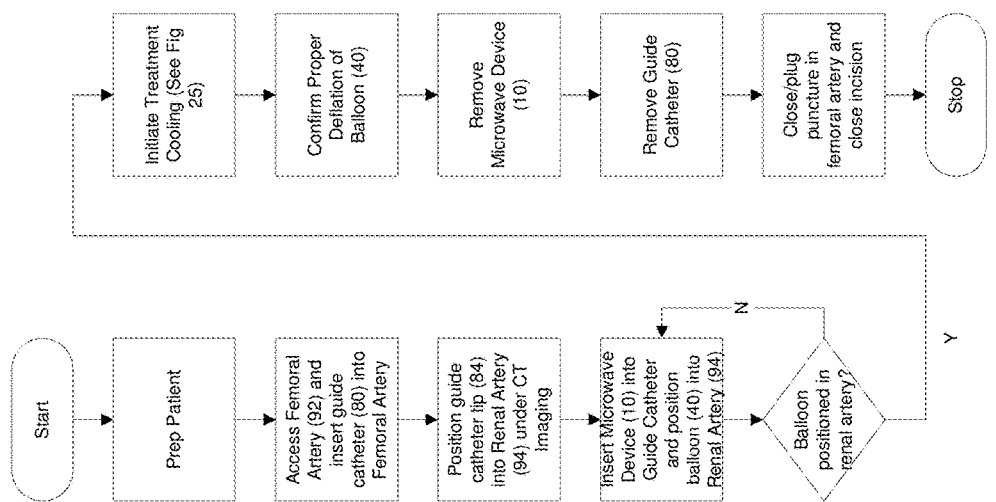
FIG. 6 is a flow chart illustrating the steps to perform renal denervation according to the present invention.

FIG. 6 is a flowchart that depicts steps for the placement of the microwave carrying catheter 10 within the renal artery 94 to accomplish renal denervation in accordance with the present invention. The patient is prepped as is well known in the art, and the femoral artery or another site such as the subclavian artery is accessed. A guide catheter is inserted according to FIG. 5A and advanced into the femoral artery 92 and advanced until the distal tip 84 of guide catheter 80 is positioned within renal artery 94 using techniques known in the art. This is commonly accomplished with the use of CT guidance and the proper position of tip 84 within renal artery 94 may also be verified by CT guidance. Microwave antenna containing catheter, 10, is advanced into guide catheter 80 and positioned such that the entire balloon 40 is contained within the renal artery 94 and the antenna coil windings 48 are placed adjacent to the desired site for renal denervation. Verification of the location of balloon 40 is critical to successful renal denervation so it is checked and repositioned as necessary. Once properly located, renal denervation is initiated according to FIG. 25 to be described in detail later. Proper inflation of balloon 40 by cooling fluid within interior 41 is also verified before initiating microwave power 140. Once the renal denervation treatment algorithm is completed, the balloon 40 will deflate when cooling flow is discontinued. The microwave carrying catheter 10 may then be removed from guide catheter using techniques known in the art. The other renal artery is treated as described above, and then the catheter 10 may be removed. The last steps are to remove guide catheter 80 and close or plug the puncture in femoral artery 92 in accordance with known techniques. The patient's insertion site is then closed and the patient is monitored as is known in the art.

Figure 7A:
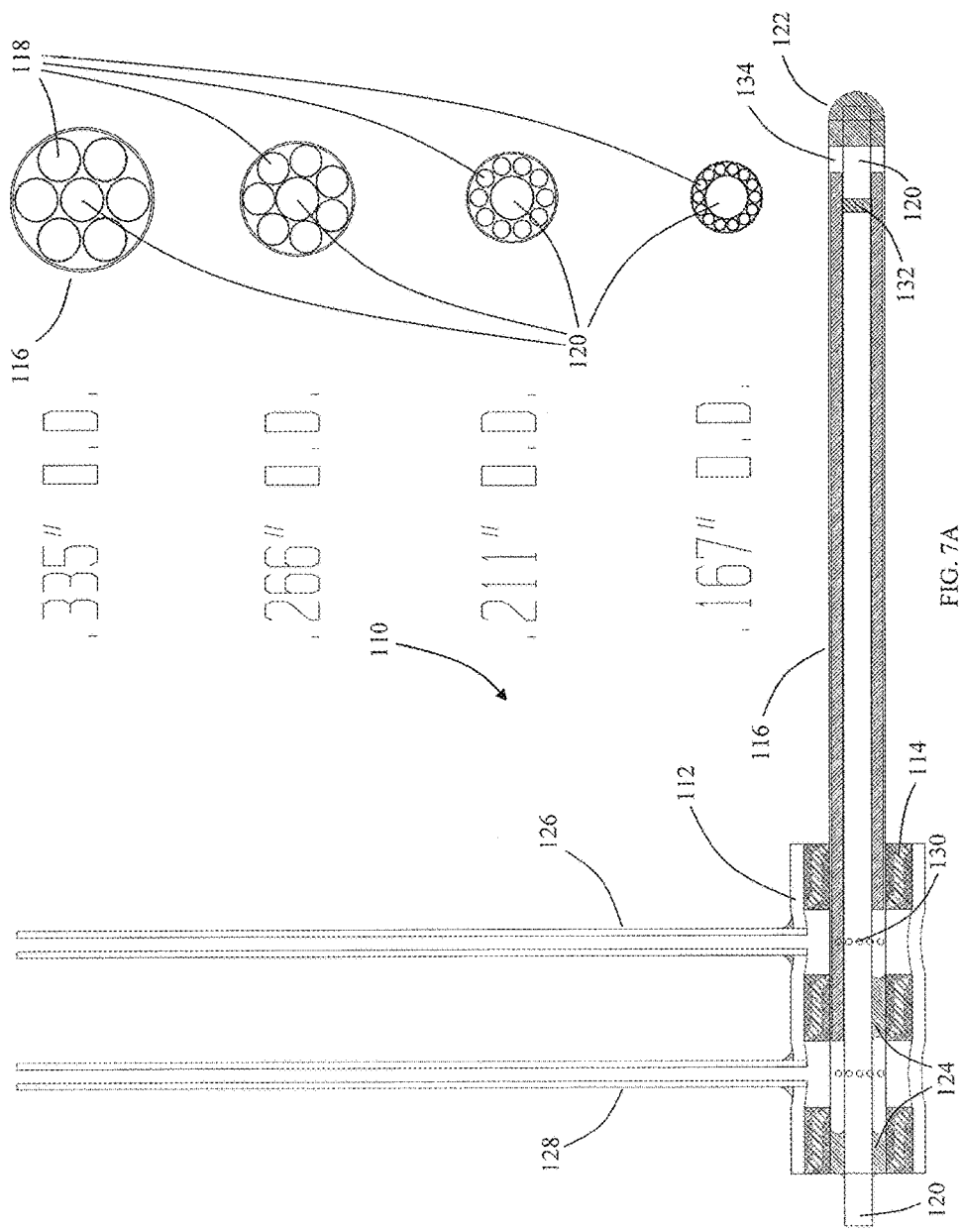
FIG. 7A is a detailed drawing of a microwave antenna carrying "needlestick" device of varying diameters.

FIG. 7A is a drawing of a "needlestick" microwave antenna carrying catheter that mimics the geometry of antenna carrying catheter 10 when balloon 40 is inflated to varying sizes. This device is rigid and does not inflate so it cannot navigate the arterial system as described above but can access the renal artery through a surgical cut down. As can be seen in the cross section insets, this device is comprised of an antenna tube 120 surrounded by spoke tubes 118 of various dimensions and number to fit within an outer tube 116 of varying diameter. FIG. 7B is a table that indicates tubing sizes and configuration (number of spoke tubings) to fabricate different diameter devices. The material for the outer tubing 116, spoke tubing 118, and antenna tubing 120 is thin wall PEEK tubing.

Coolant exchange holes 130 are punched in outer tubing 116 so that coolant may communicate between manifold formed by manifold tube 112 and spacer tubes 114 that may be silicone or another convenient material. Manifold tubing 112 communicates with coolant inlet tubing 126 and coolant exhaust tubing 128, both bonded to manifold tubing with UV cure silicone adhesive. Antenna tubing 120 and spoke tubing 118 are cut to length to fit within outer tubing 116 and arranged as shown in the cross section inset on FIG. 7A. In one embodiment, every other spoke tube is a shorter length such that a dam of adhesive 124 may be injected into the region between the longer spoke tubing, antenna tubing, and outside tubing in the vicinity of the center of manifold tubing 112. This separates groups of spoke tubing so that the inlet coolant flowing within inlet tubing 126 at temperature 142 will flow down to the distal exchange area 134 within the short spoke tubes and the space between spoke tubes, antenna tube, and outside tube. The coolant exchanges at 134 and flows back through the longer spoke tubes through the coolant exchange holes 130 and on to the exhaust tubing 128 via the manifold tubing 112 and manifold spacer tubing 114. The antenna tubing 120 and outside tubing 116 are sealed at the distal end by plug 122 formed by adhesive. The adhesive used for plug 122 and potting 124 may be a UV cure adhesive such as Loctite® 3311 or 3341. The adhesive used to bond inlet and outlet tubing (126 and 128) to manifold tubing 112 may be UV cure silicone adhesive such as Loctite® 5083. In some sizes, it is useful to include a shim 132 to help keep the spoke tubing 118 and antenna tubing 120 stationary.

Figure 8A:
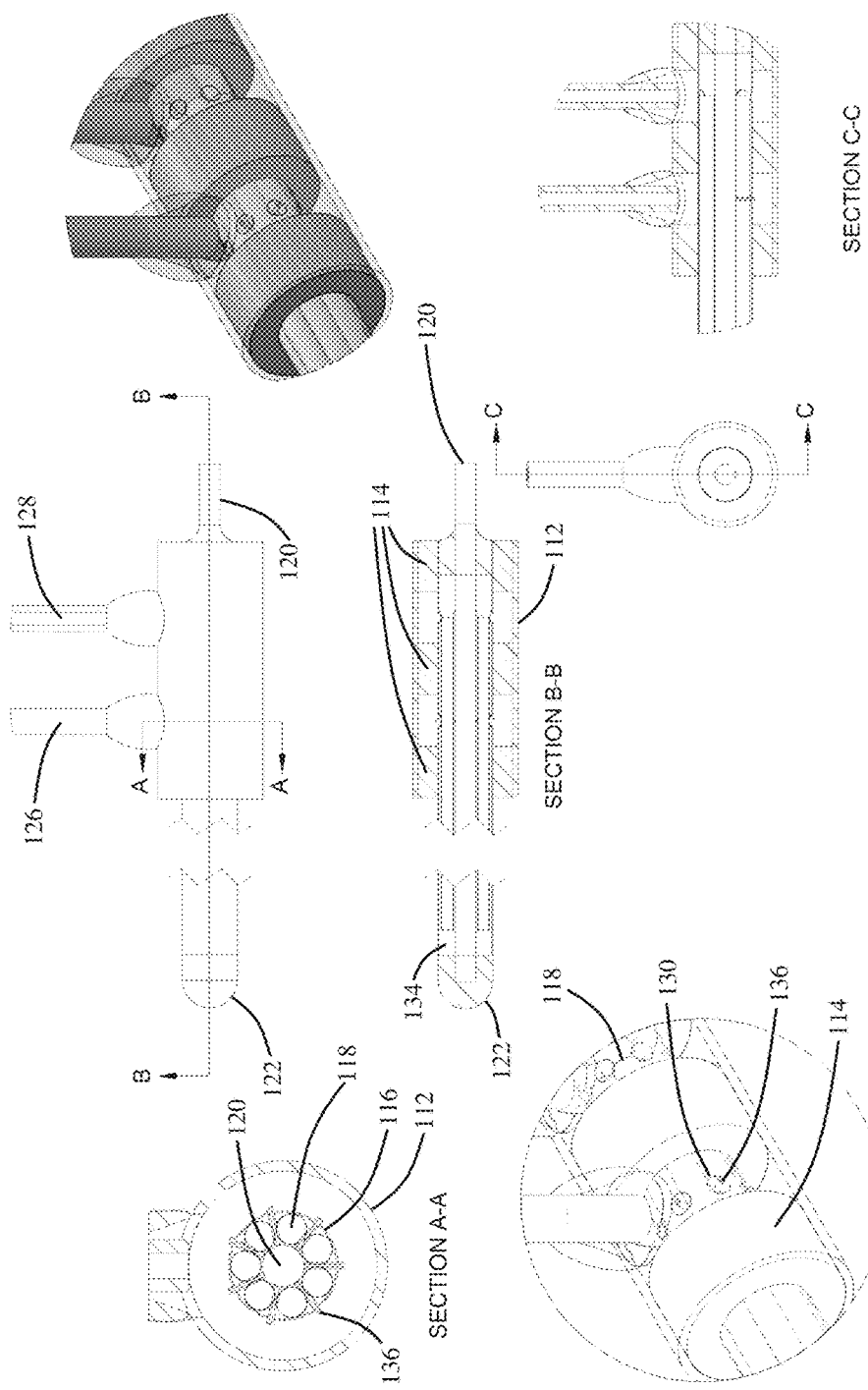
FIGS. 8A-8D are photographs of various prototype "needlestick" devices.

In an alternate arrangement of spoke tubing, the tubes are all of equal length and potting is applied in the space between tubes in the vicinity of the center of the manifold tubing. In this case, coolant flows down to exchange area 134 in the spaces between the spoke tubes and returns within the spoke tubes. In the manifold, it is helpful to include spoke tubing shims 136 as shown in FIG. 8A to allow coolant to flow between the spoke tubes and communicate with coolant exchange holes 130.

Figure 8B:
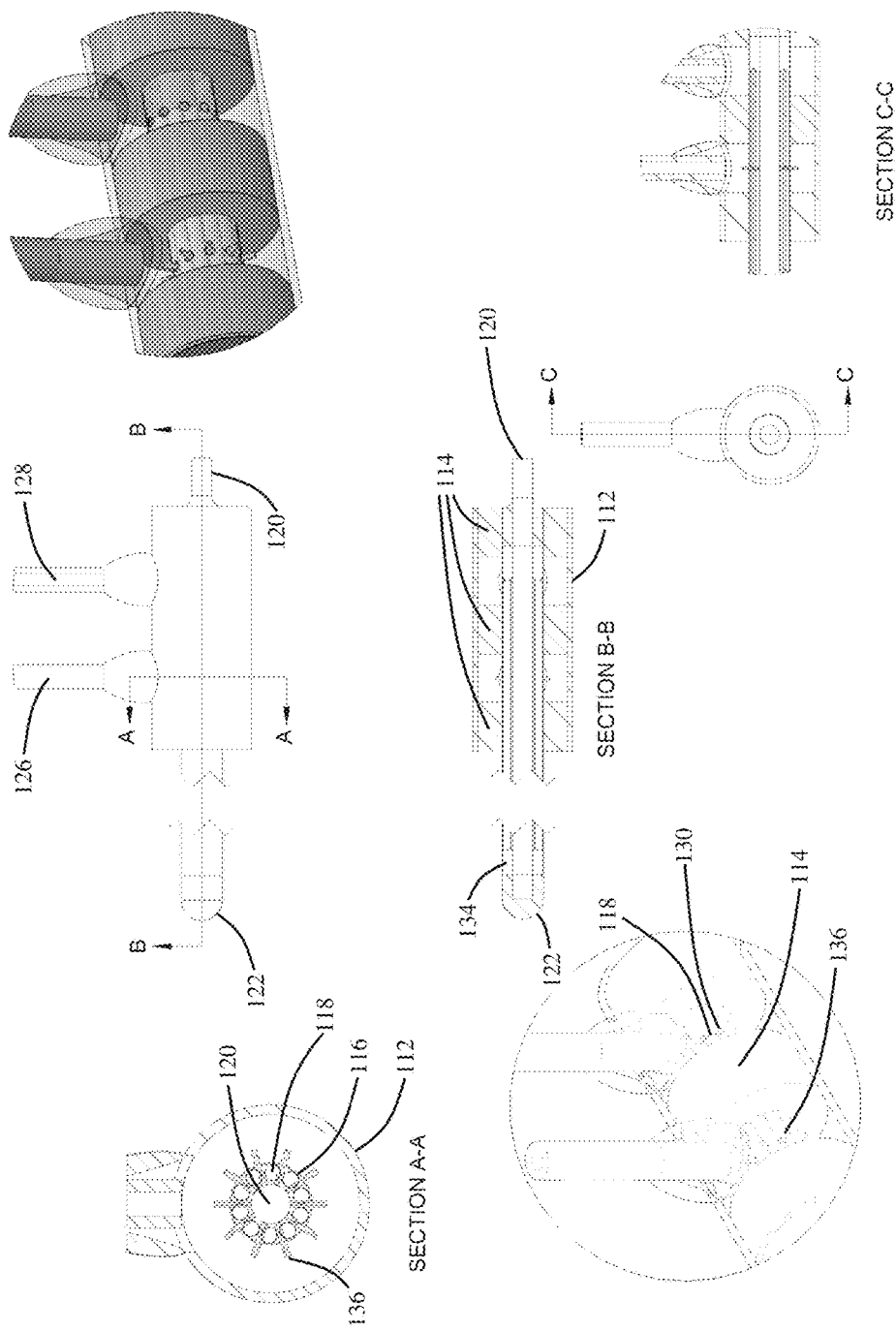
Figure 8C:
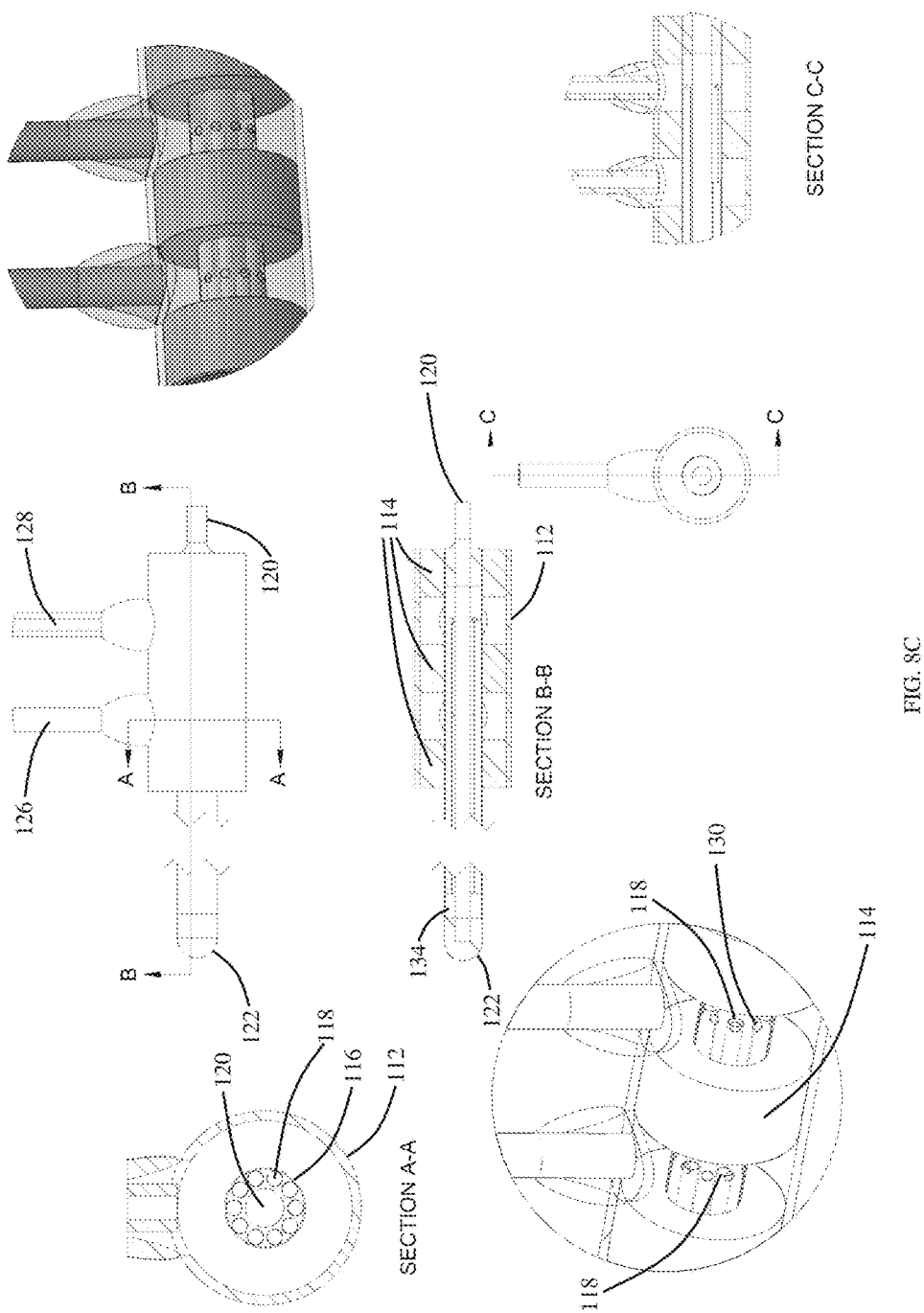
Figure 8D:
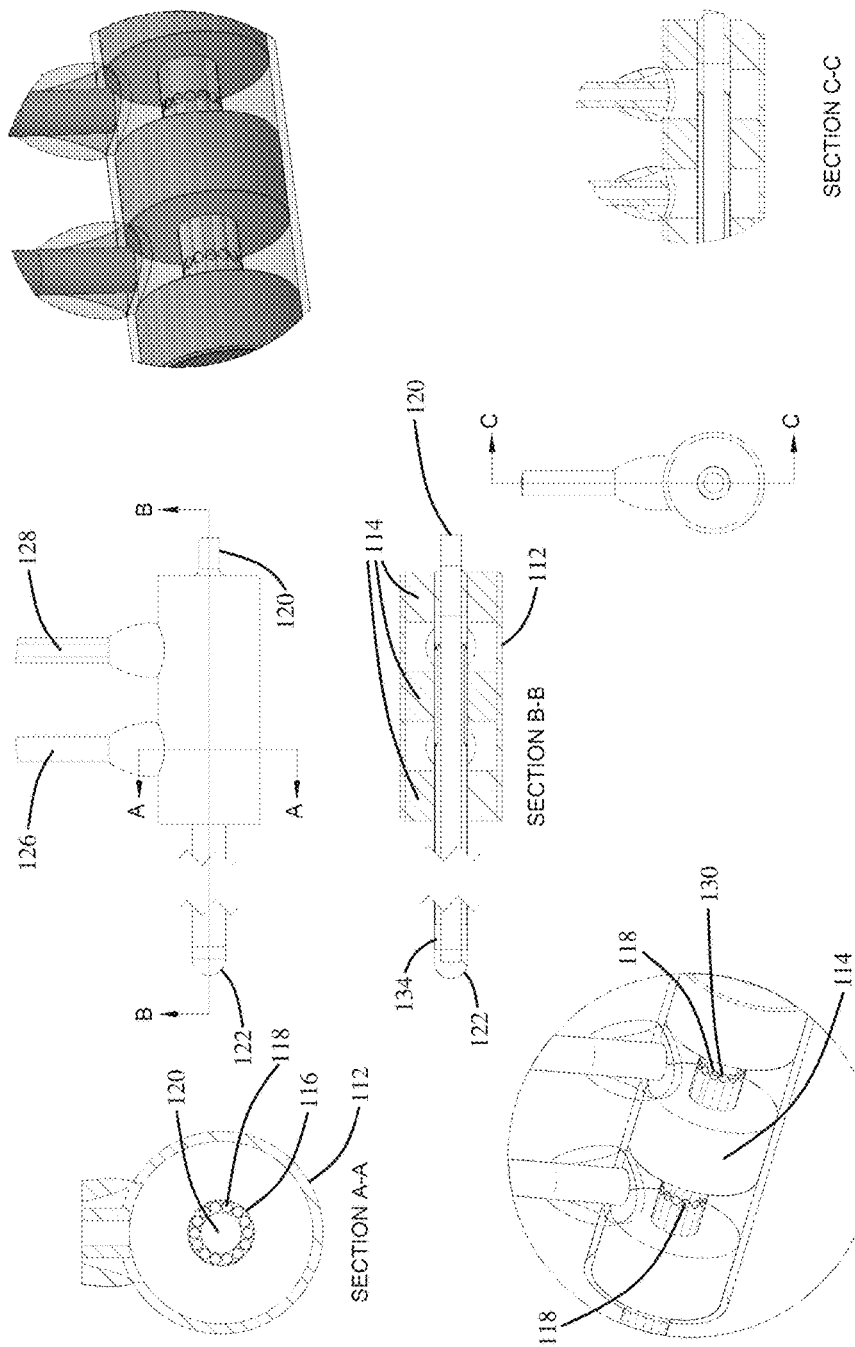

FIG. 8B-8D are photographs of various size devices that were fabricated to perform bench and animal testing of microwave renal denervation in accordance with the present invention. FIG. 8A is a 6.76 mm O.D. device and, per table in FIG. 7B, contains 7 spoke tubes 118 of 0.102" O.D. surrounding the antenna tube 120 also of 0.102" O.D. FIG. 8A has reference numbers to mark components as described above. Spoke tubing shim 136 is visible extending through coolant exchange holes 130.

FIG. 8B is a 5.36 mm O.D. device and is fabricated with the use of spoke tubing shims 136.

FIG. 8C is also a 5.36 mm O.D. device but is fabricated using alternate short/long length spoke tubes 118 separated by adhesive potting 124. The alternate length spoke tubing 118 adhesive potting, 124, and coolant exchange holes 130 are clearly visible. There is one coolant exchange hole 130 centered on the location of each of the short spoke tubes.

FIG. 8D is a 4.24 mm O.D. device and is fabricated using alternate short/long length spoke tubes 118 separated by adhesive potting 124. Fourteen (14) spoke tubes 118 are visible surrounding antenna tube 120.

Bench Top/Phantom Study

Figure 9:
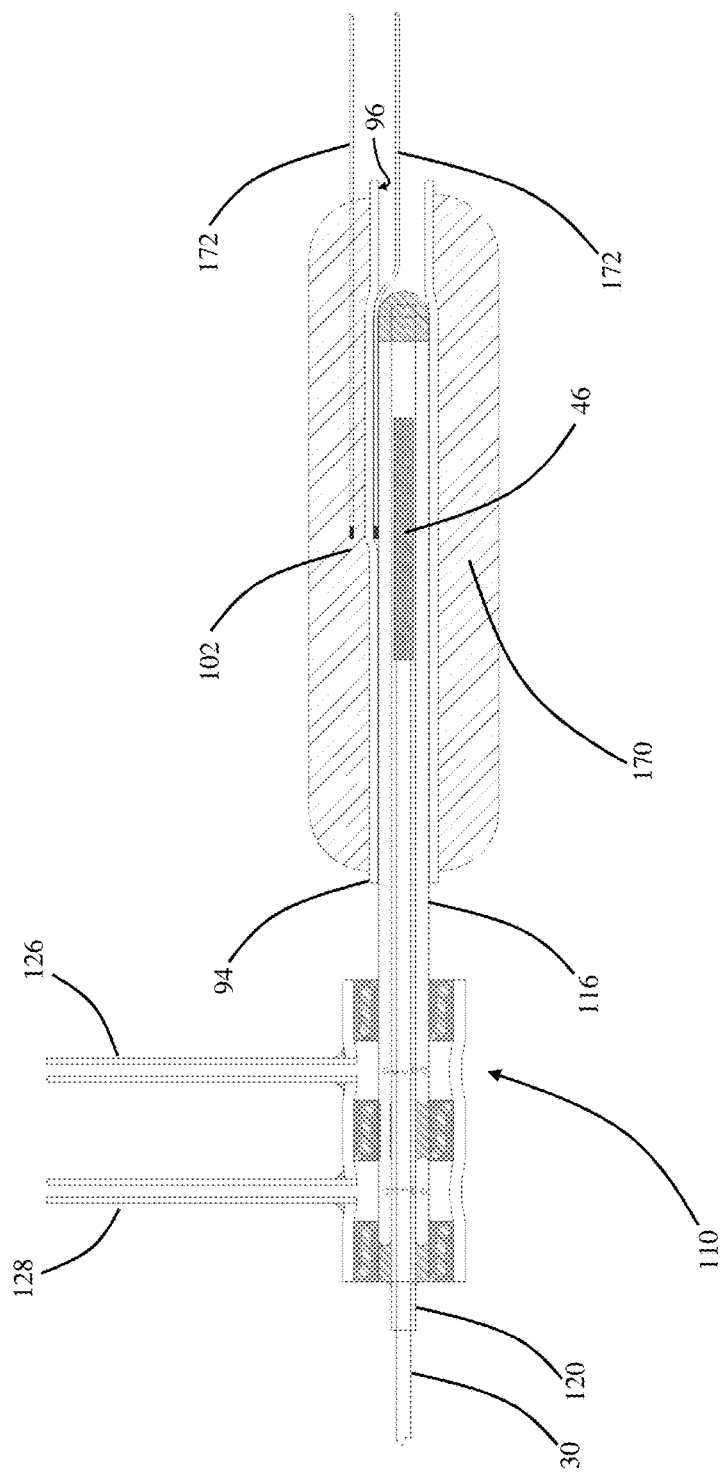
FIG. 9 is a photograph illustrating the catheter prototype of FIG. 7A configured with an ex vivo porcine renal artery surrounding the catheter and positioned within a gel-filled tube that serves as a phantom for the tissue and fat located around the renal artery.

A bench simulation of microwave based renal denervation therapy was performed to show that the principles shown in the computer simulation described above could be physically produced. FIG. 9 is a photograph illustrating the needlestick catheter prototype 110 as described above configured with an ex vivo renal artery 94 surrounding the catheter positioned within a tissue phantom gel 170 filled in a tube that serves as a phantom for the tissue and fat located around the renal artery. Fiber optic temperature probes 172 are placed between the intima 96 of renal artery 94 and the outer tubing 116 of needlestick device 110 to enable direct measurement of intima temperature. Additional fiber optic temperature probes are placed between the adventitia 110 and tissue phantom gel 170 to capture temperature at the location of renal nerves 102. Fiber optic temperature probes 172 are used because they do not interact with the microwave field generated by the antenna 46 within needlestick prototype 110 and as a result there is no temperature artifact that would otherwise invalidate the recorded temperature. With the bench top setup shown in FIG. 9 and described above, a renal denervation treatment was run by applying circulating coolant and microwave power as shown in FIG. 10.

Figure 10:
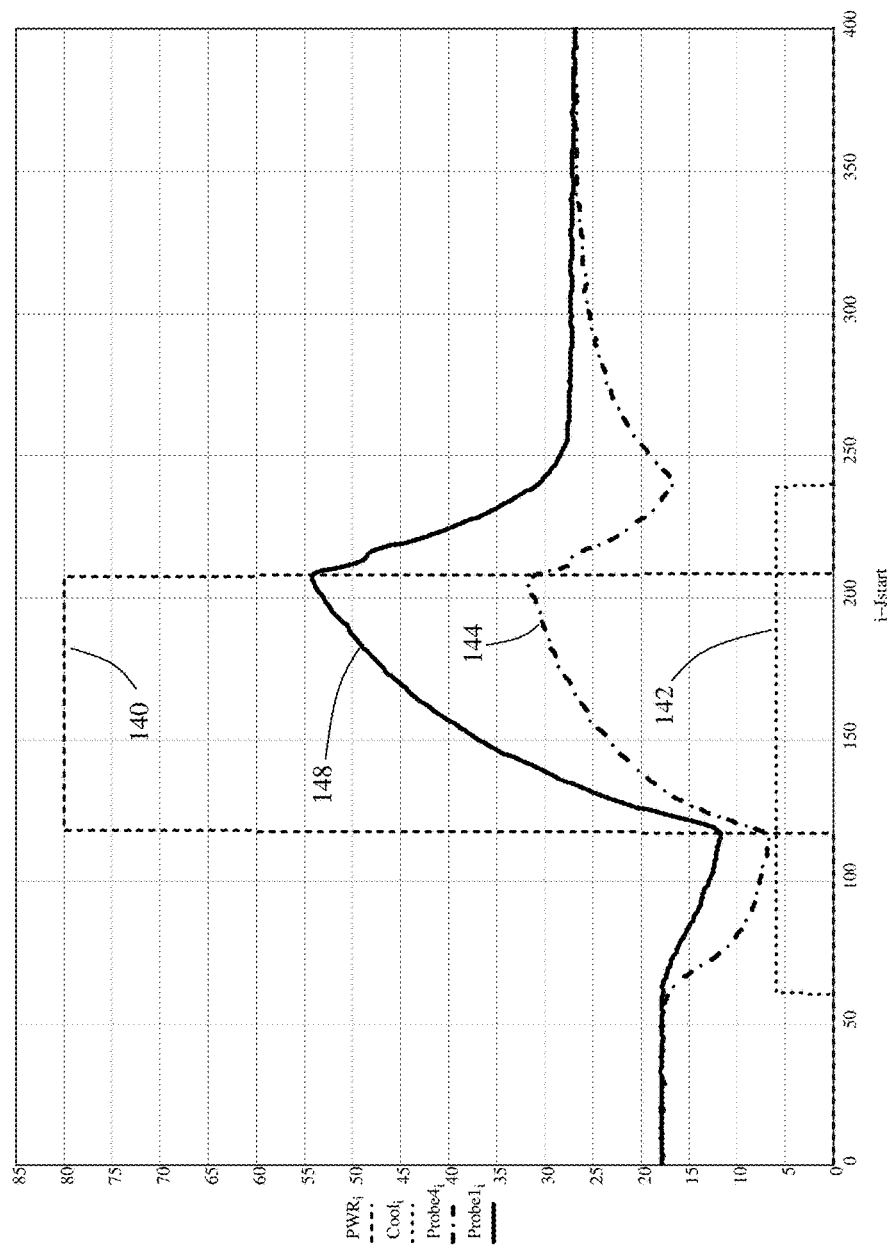
FIG. 10 is a graph illustrating empirical temperature readings obtained from the bench simulation of microwave based renal denervation therapy as shown in FIG. 9 using a prototype device as shown in FIG. 7A.

FIG. 10 is a graph illustrating cooling inlet temperature 142, microwave power 140, and the resulting temperatures at the intima 144 and adventitia 148 during a bench top study. Cooling fluid at about 6° C. (142) was circulated for approximately 60 seconds prior to initiating microwave power (140) for about 90 seconds. A "cool down" period of about 30 seconds follows the discontinuation of microwave power. As can be seen, the maximum advantitia temperature is over 20° C. warmer than the maximum intimal temperature in this representative phantom run. This temperature difference will enable renal denervation without damage to the intima or media.

Figure 11:
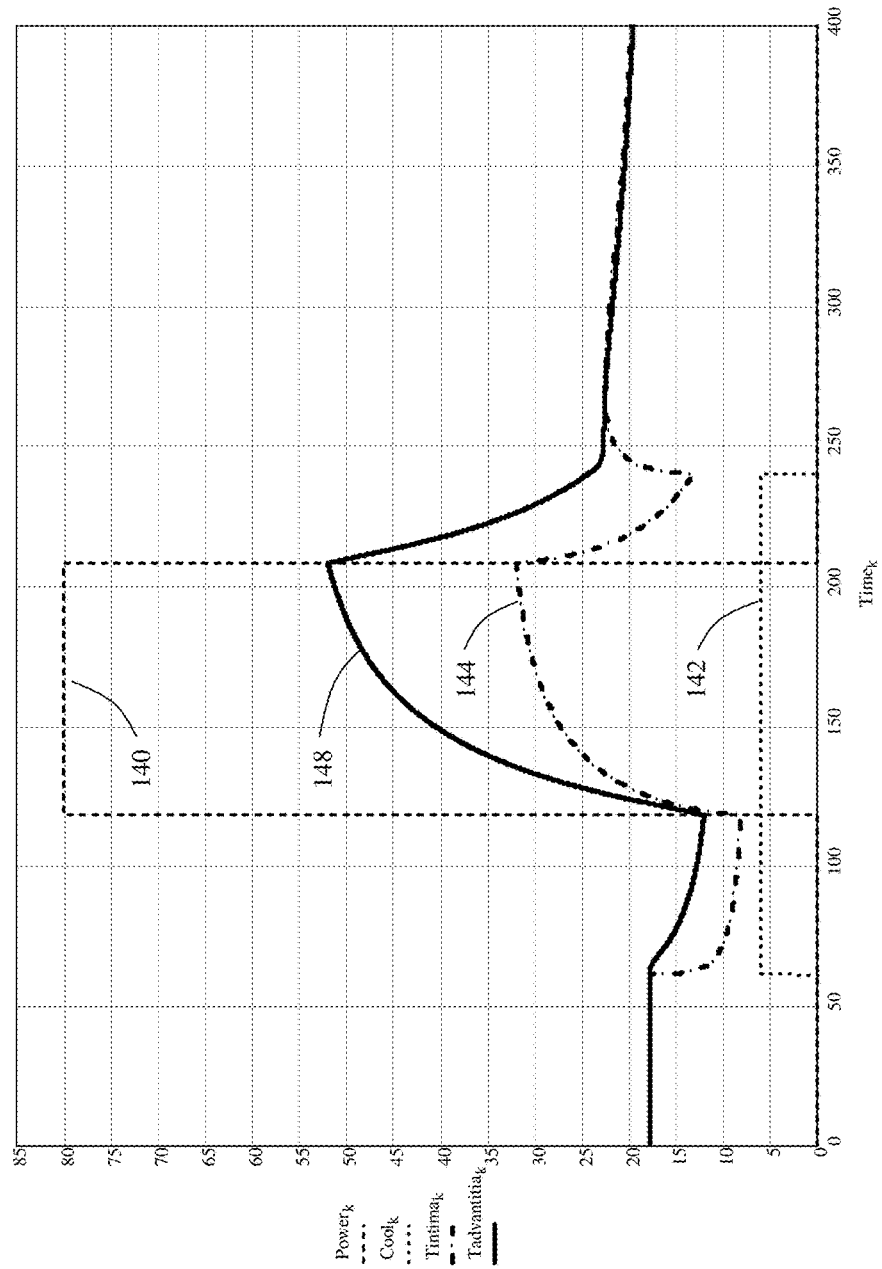
FIG. 11 is a graph illustrating a computer simulation of the bench simulation that resulted in the graph of FIG. 10.

FIG. 11 is a computer simulation as described above for the specific bench top phantom study described above and plotted in FIG. 10. Coolant temperature (142) and microwave power (140) as functions of time were input into the model and the intimal temperature (144) and adventitial temperature (148) were simulated and are plotted in FIG. 11. As observed empirically, the simulation also indicates a bit over 20° C. difference between intimal and adventitial temperature. The simulated temperature plots are in excellent agreement with the empirical data described above and plotted in FIG. 10.

Porcine Study

A porcine study was performed by performing a surgical cut down to access the abdomen, remove the intestines, and access the abdominal aorta with minimal disruption to the kidneys and renal arteries. This procedure was done immediately after stopping the heart to enable incising the abdominal aorta without obscuring view due to blood loss. Once the abdominal aorta was accessed and incised, the renal artery ostium was identified by palpating the appropriate kidney and observing blood flowing backwards out the renal ostium. A prototype needlestick device (110) was inserted into the renal ostium and advanced into the renal artery until the tip 122 reached the terminal branches. Fiber optic temperature sensors 172 were also placed into the renal artery between the prototype 110 and the intima 96 and advanced until the temperature sensing portion of 172 was adjacent to the SAR producing portion of the antenna coil 48. Additional sensors were placed immediately adjacent to the adventitia with the use of an 18 G needle inserted through the abdominal aorta and parallel to the prototype 110 and then the needle was withdrawn, leaving the sensor 172 in place. Temperatures from all fiber optic probes were captured and logged to a file for later analysis.

Figure 12:
FIGS. 12 and 13 are photographs illustrating a catheter prototype and temperature probes inserted into a right renal artery of a porcine carcass.
Figure 13:

FIGS. 12 and 13 are photographs illustrating a catheter prototype and temperature probes inserted into a right renal artery of a porcine carcass as described above.

Figure 14A:
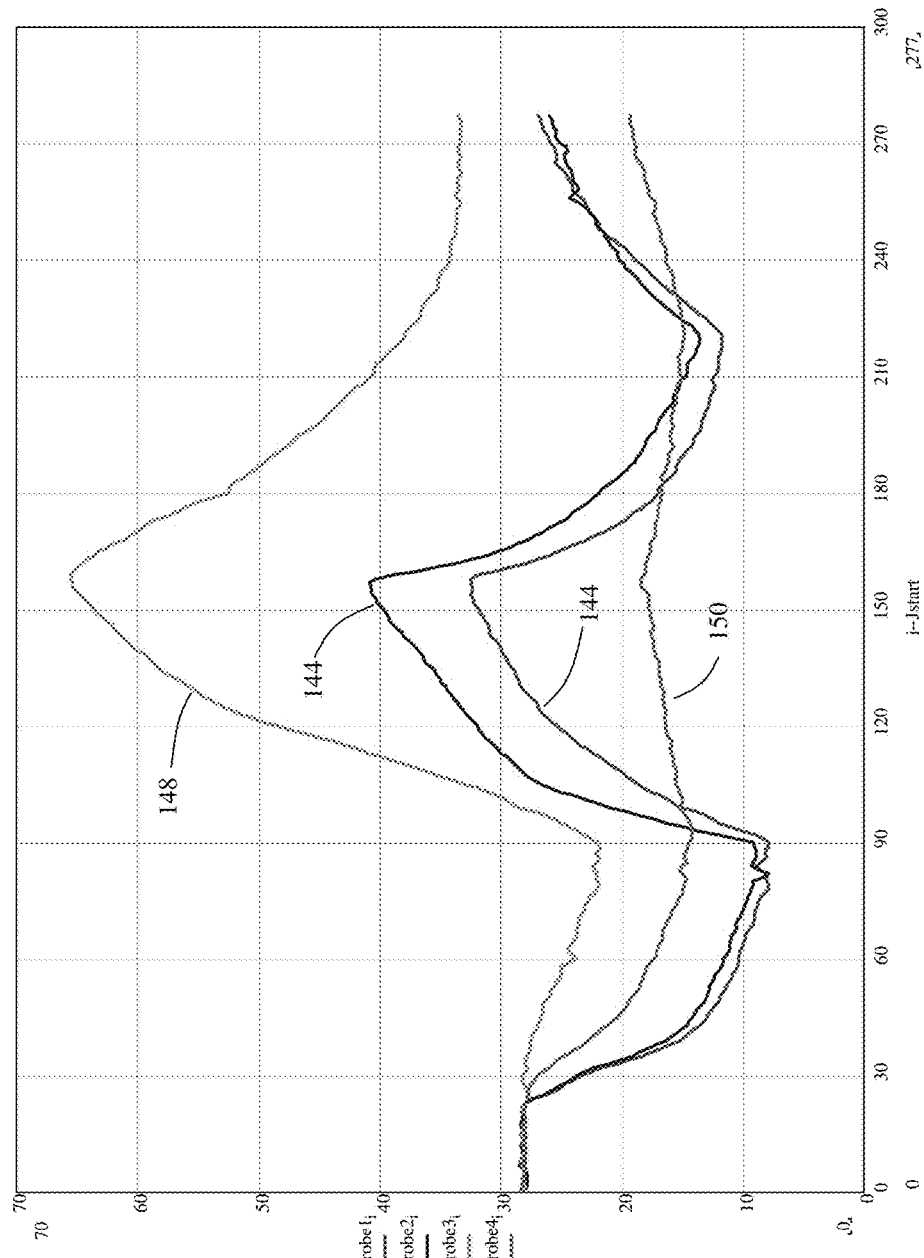
FIG. 14A is a graph illustrating temperature data obtained in a region of the right renal artery during the porcine study shown in FIGS. 12 and 13.
Figure 15:
FIGS. 15-18 are photographs illustrating a catheter prototype and temperature probes inserted into a left renal artery of a porcine carcass.
Figure 16:
Figure 17:
Figure 18:

FIG. 14A is a plot of all recorded fiber optic temperature sensors captured in the right renal artery. Please note that one of the sensors measuring temperature at the intima (144) was not placed adjacent to the maximum SAR producing portion of the antenna coil, 48, and therefore did not record temperature data quite as high.

FIG. 14B is a plot of the intimal (144) and adventitial (148) temperature adjacent to the maximum SAR portion of antenna coil 48. As can be seen from this graph, the adventitial peak temperature is about 24° C. higher than the intimal peak temperature.

FIG. 14C is a plot of simulated intimal (144) and adventitial (148) temperature adjacent to the maximum SAR portion of antenna coil 48. Excellent agreement exists between simulation (FIG. 14C) and empirical (FIG. 14B) temperature data.

FIGS. 15-18 are photographs illustrating a catheter prototype and temperature probes inserted into a left renal artery of a porcine carcass as described above.

Figure 19A:
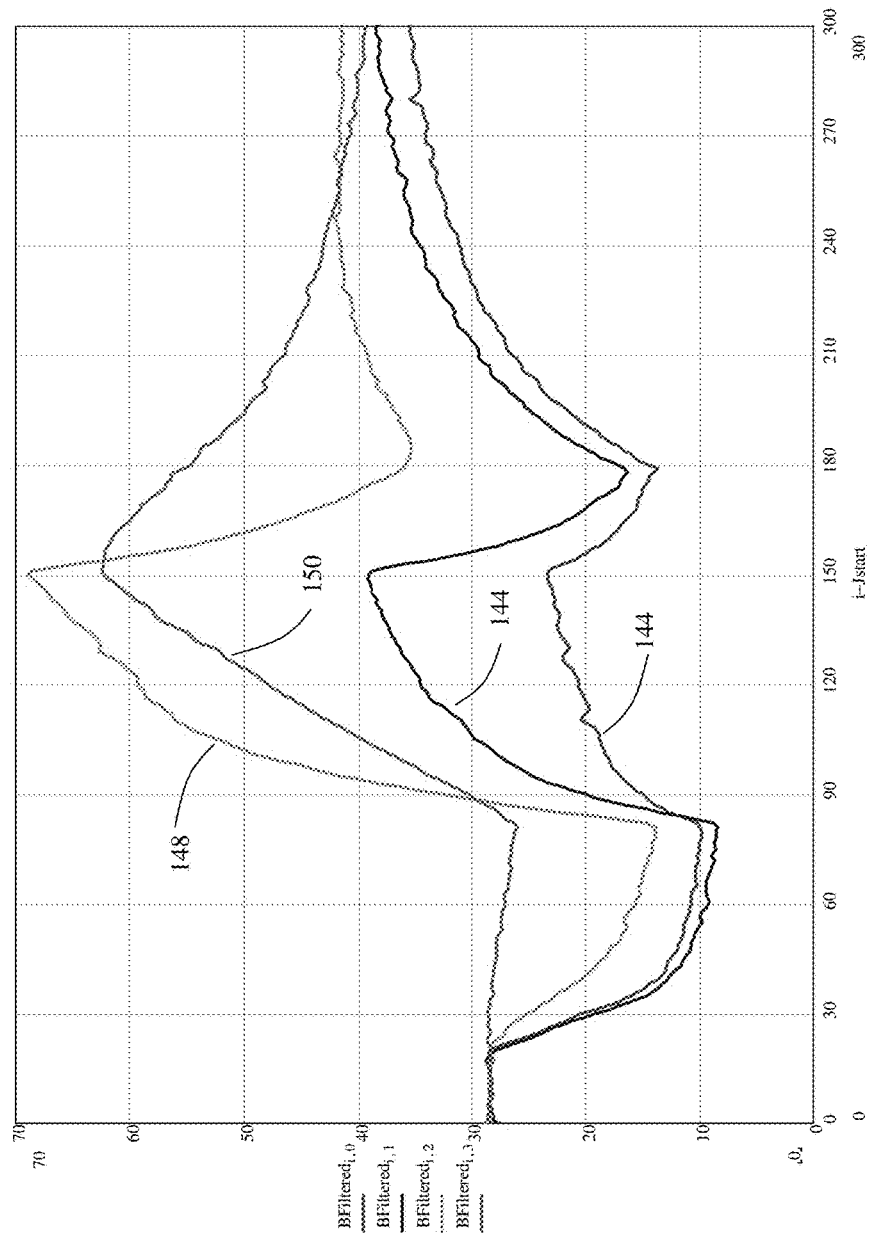
FIG. 19A is a graph illustrating temperature data obtained in a region of the left renal artery during the porcine study shown in FIGS. 15-18.

FIG. 19A is a graph illustrating temperature data obtained from all temperature sensors in a region of the left renal artery during the porcine study described above. As above, one of the intima sensors did not record temperature as high as the other due to placement difficulties.

Figures 19B, 19C:
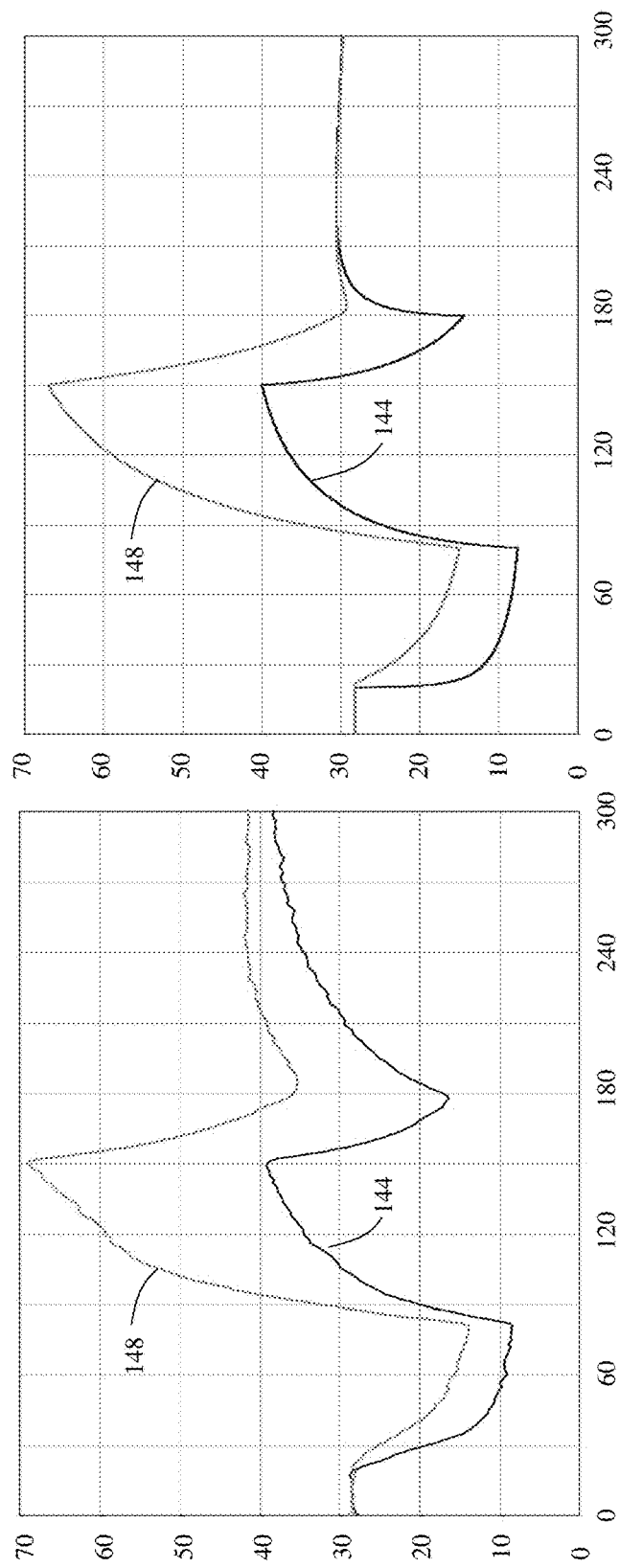
FIG. 19B is a graph illustrating specific temperature data obtained in a region of the left renal artery during the porcine study shown in FIGS. 15-18.
FIG. 19C is a graph illustrating a computer simulation of the specific temperature data plotted in FIG. 19B.

FIG. 19B is a graph of intimal (144) and adventitial (148) temperature data captured in the porcine study described above adjacent to the maximum SAR portion of antenna coil 48.

FIG. 19C is a graph of simulated intimal (144) and adventitial (148) temperature adjacent to the maximum SAR portion of antenna coil 48. As for the opposite renal artery, excellent agreement exists between empirical (FIG. 19B) and simulated (FIG. 19C) data. Additionally, there is greater than 20° C. difference between intimal and adventitial tissue temperature, thus enabling renal denervation without thermal damage to the intima or media.

Histology Study

An additional porcine study was performed to study cellular injury at a cellular level in order to demonstrate that renal denervation according to the present invention is possible without damage to the intima or media of the renal artery. Nitro blue tetrazolium (NBT) staining was performed on porcine tissue sections following renal denervation using the prototype device 110 as described previously. Temperature data was captured as before and the tissue was stained, frozen, sliced and mounted on slides for viewing under a microscope. NBT stained tissue appears deep blue if viable (not thermally injured) and appears yellow-tan in regions of cell death.

Figure 20A:
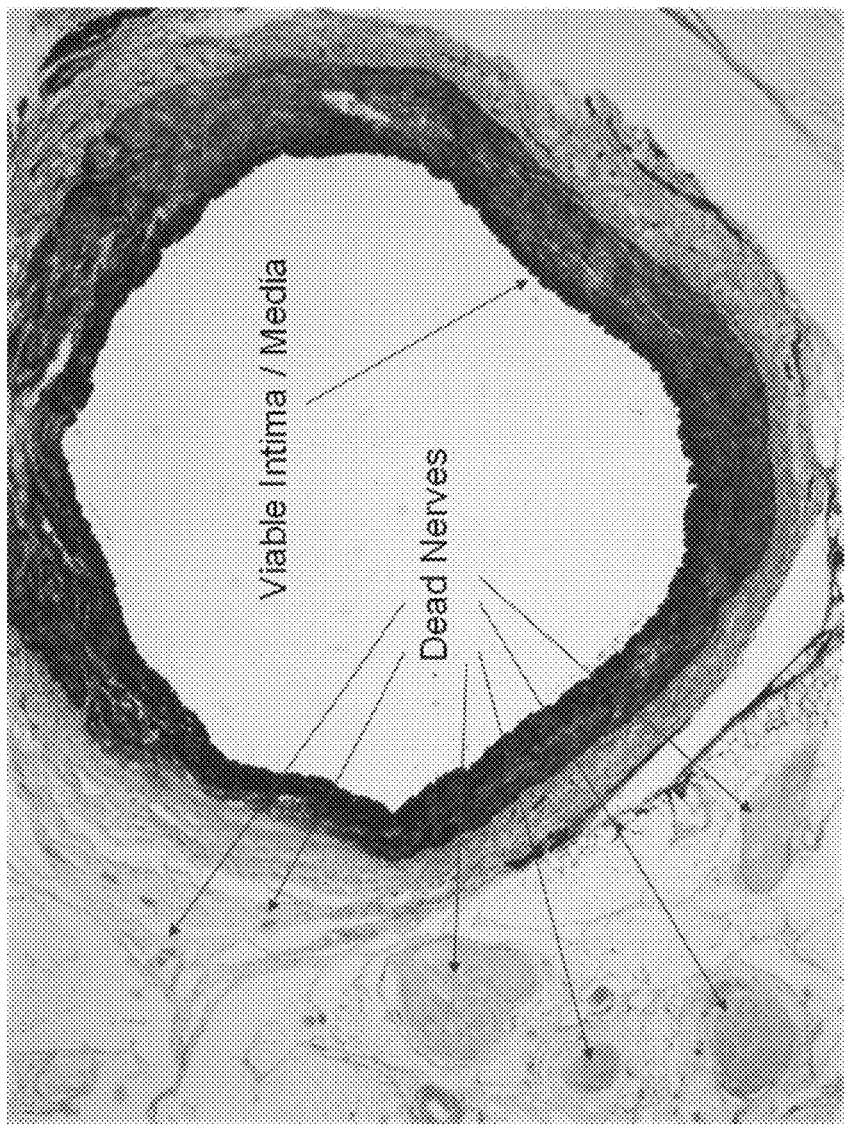
FIGS. 20A-20C are histology slides that demonstrate thermal destruction of renal nerves without any damage to the intima and media of a representative porcine renal artery using a prototype device as shown in FIGS. 7A and 7B in accordance with the present invention.

FIG. 20A is a cross section of an NBT stained porcine artery following microwave renal denervation. As can be seen the intima and media are deep blue indicating undamaged living tissue, all the way around the artery. A fully circumferential region of thermal injury is evident surrounding the viable media tissue; within that zone, the renal nerves identified in FIG. 20A are all dead.

Figure 20B:
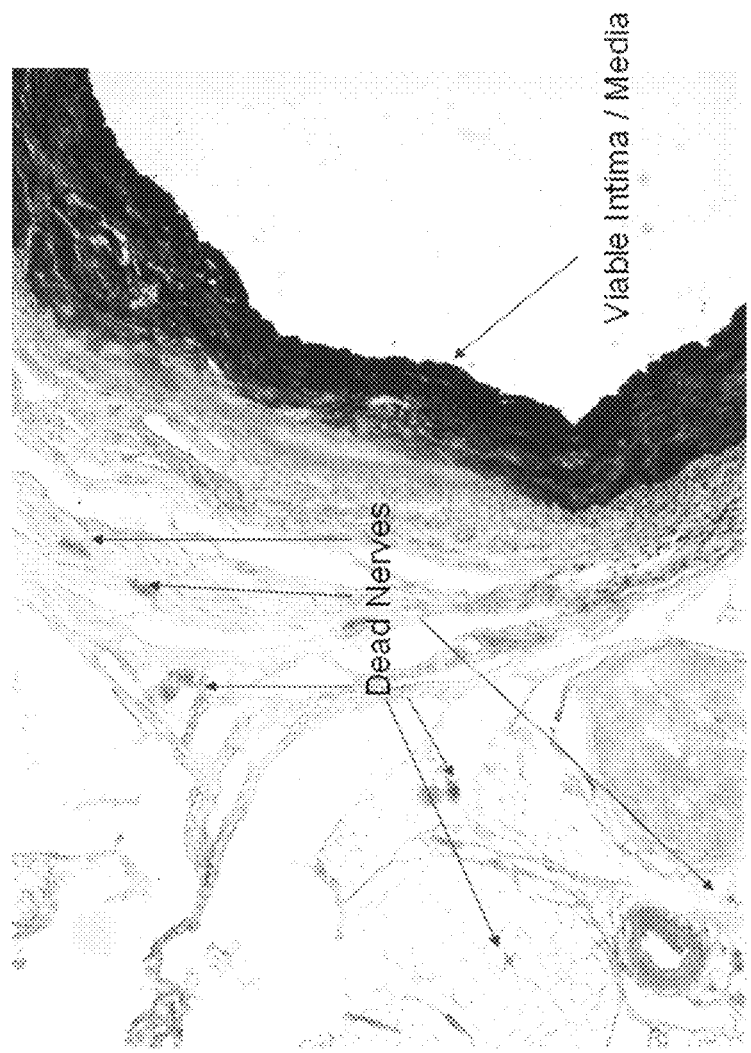

FIG. 20B is another cross section of the artery in FIG. 20A, but at a different position. As above, the nerves are dead but the intima and media are viable.

Figure 20C:
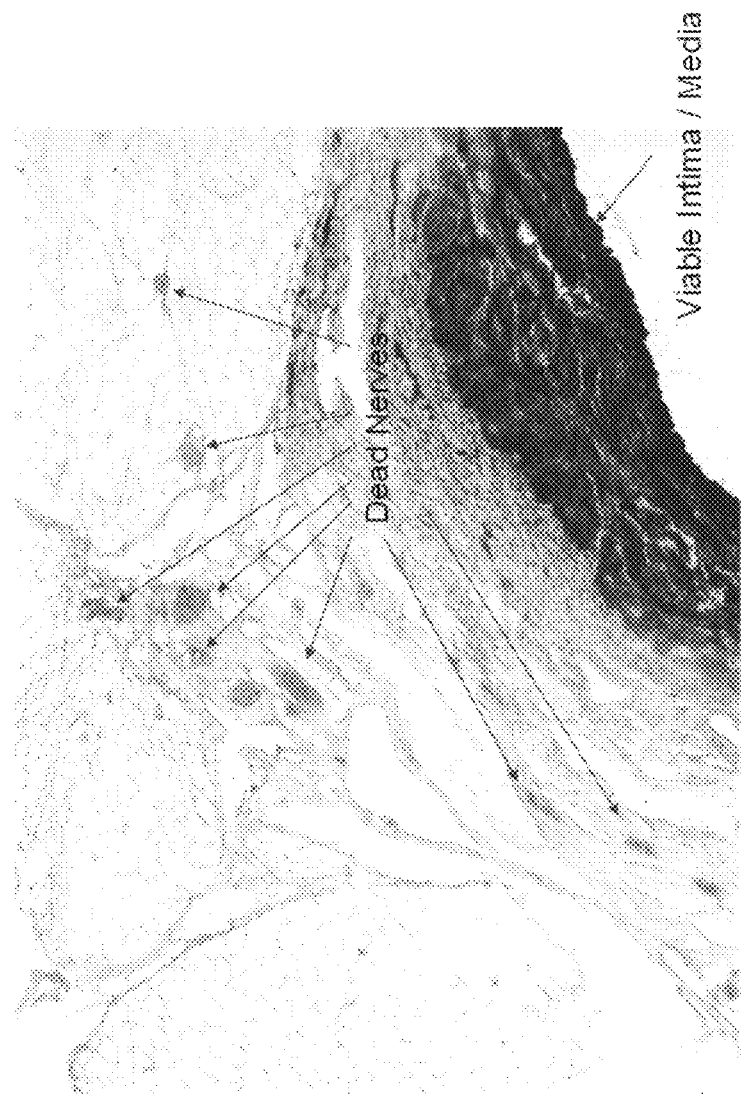

FIG. 20C is yet another cross section of the artery in FIG. 20A at another position. As above, the nerves are dead but the intima and media are viable.

Figure 20D:
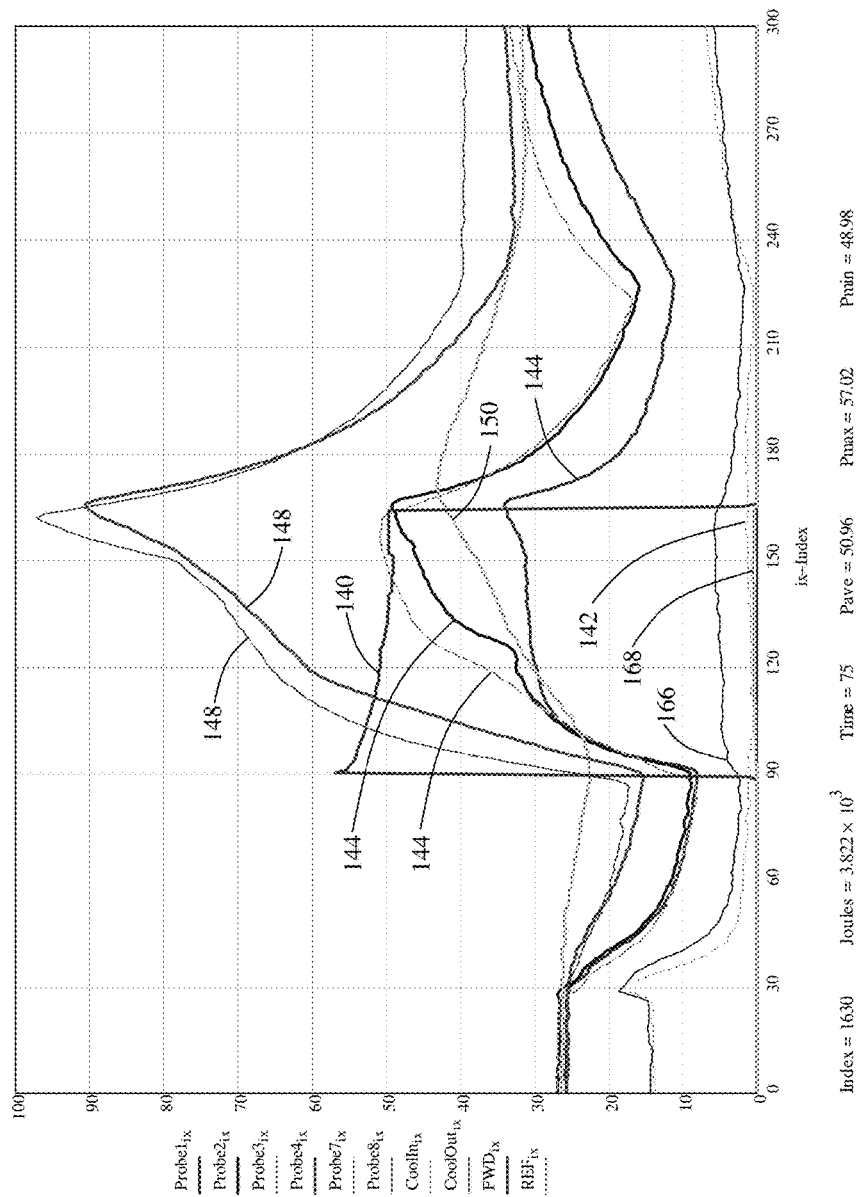
FIG. 20D is a graph of the microwave power, microwave reflected power, coolant temperature, and tissue temperatures in the region of a porcine renal artery during microwave renal denervation in accordance with the present invention that produced the histology sections shown in FIGS. 20A-20C.

FIG. 20D is a graph of the renal denervation parameters and measured temperature data that produced the histology depicted in FIG. 20A-20C. Microwave power (140) was applied for 75 seconds with an exponentially decaying amplitude that will be described later. Coolant inlet temperature (142), outlet temperature (166) and reflected power in Watts (168) are plotted as shown. Intimal temperature sensors (144) located in various positions are plotted as are adventitial temperatures (148) and surrounding tissue temperature (150).

Figure 21A:
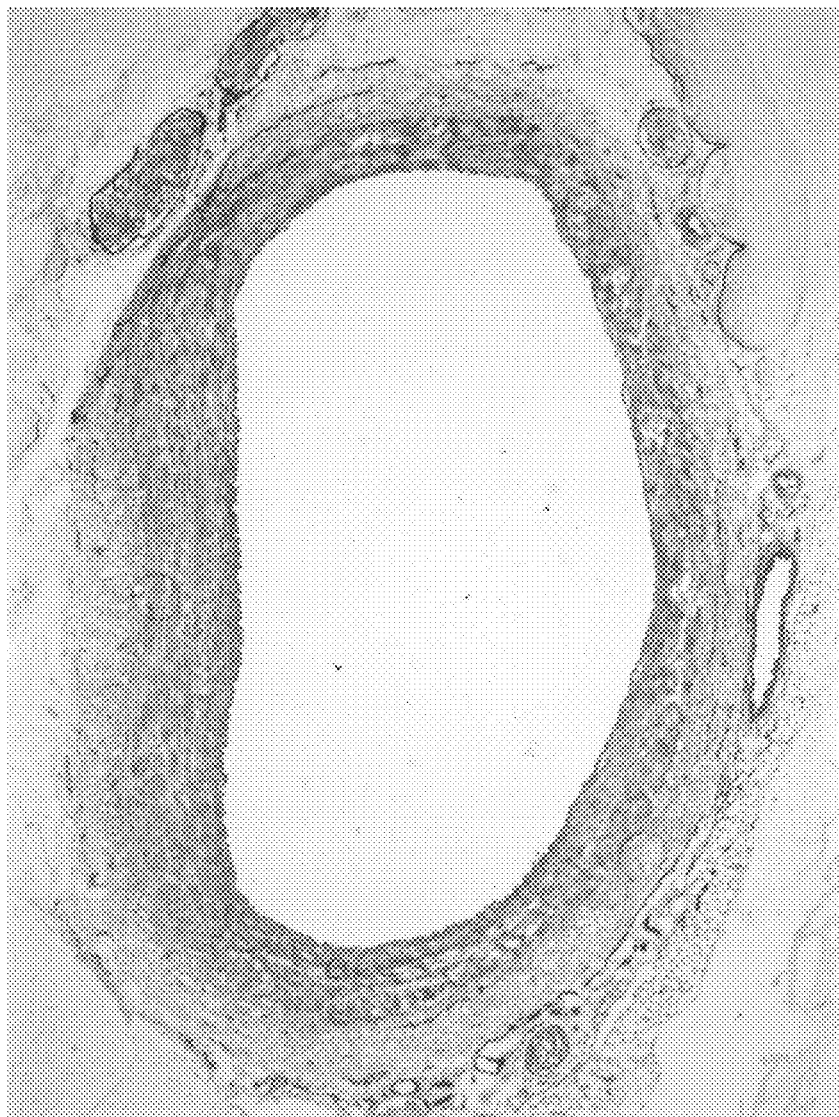
FIGS. 21A, 22A, 23A and 24A are additional histology slides of representative porcine arteries.
Figure 21:
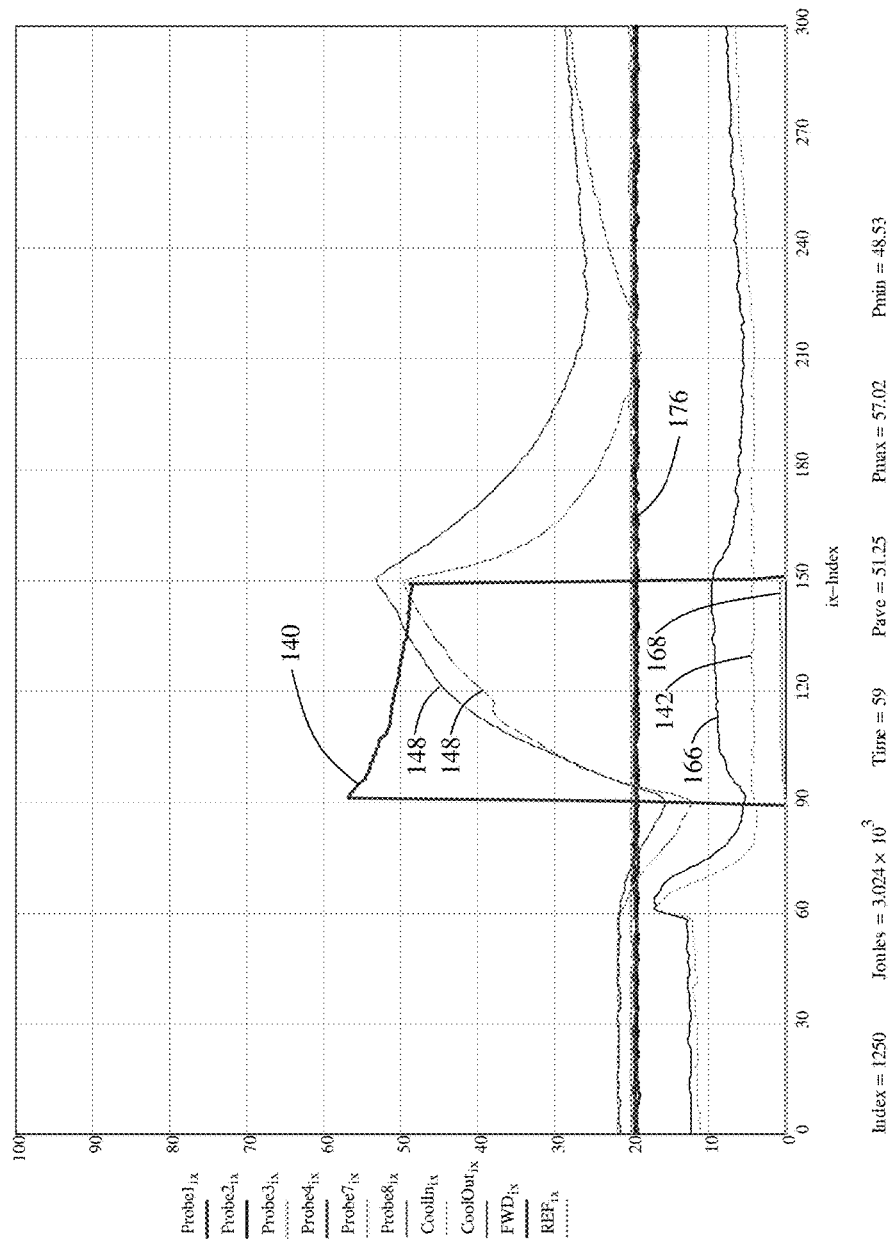
FIGS. 21B, 22B, 23B and 24B are additional representative graphs of microwave power, microwave reflected power, coolant temperature, and tissue temperatures in the region of a porcine renal artery during microwave renal denervation in accordance with the present invention that produced the accompanying histology sections depicted in FIGS. 21A, 22A, 23A and 24A.

FIG. 21A is another cross section of a different NBT stained renal artery following the microwave renal denervation parameters shown in FIG. 21B. Temperature data is as above except several probes labeled 176 were unused.

Figure 22A:
Figure 22B:
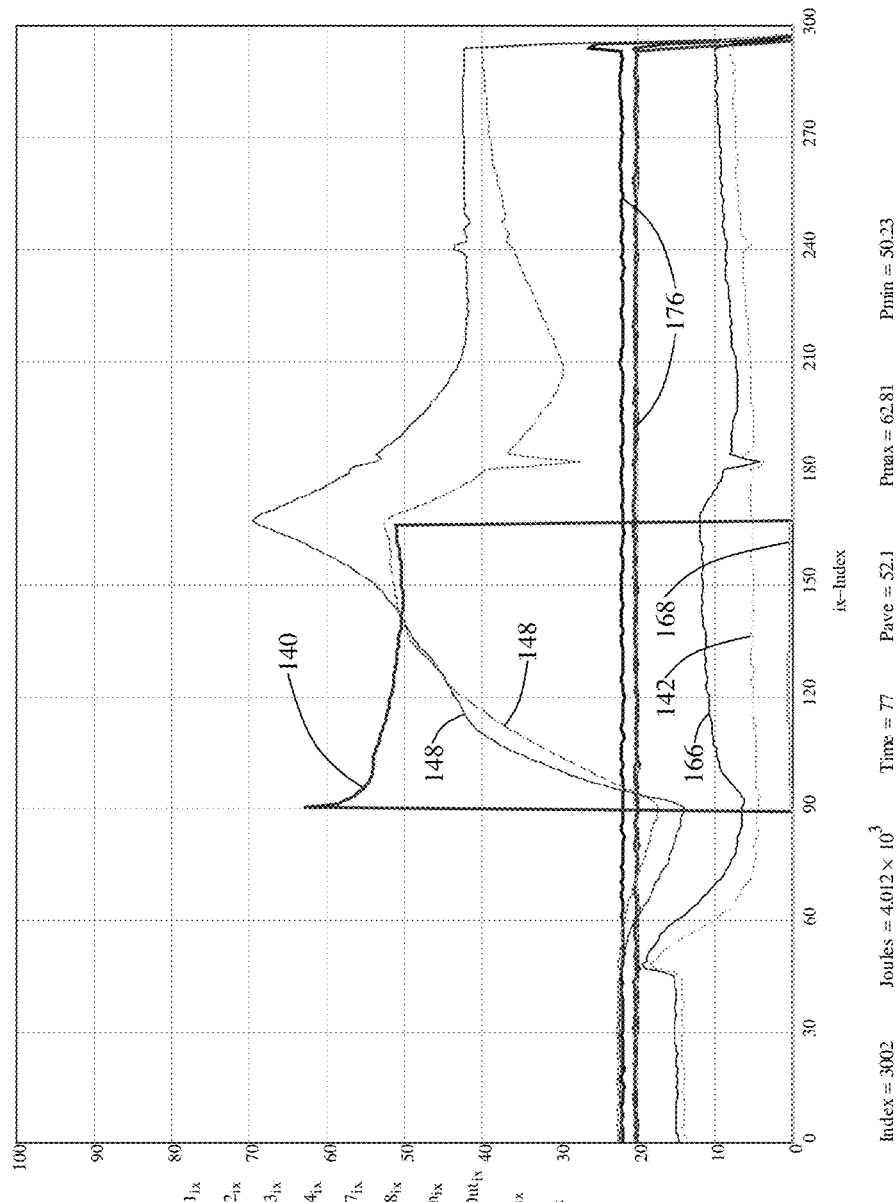

FIG. 22A is another cross section of a different NBT stained renal artery following the microwave renal denervation parameters shown in FIG. 22B. Label designators are as described above.

Figure 23A:
Figure 23B:
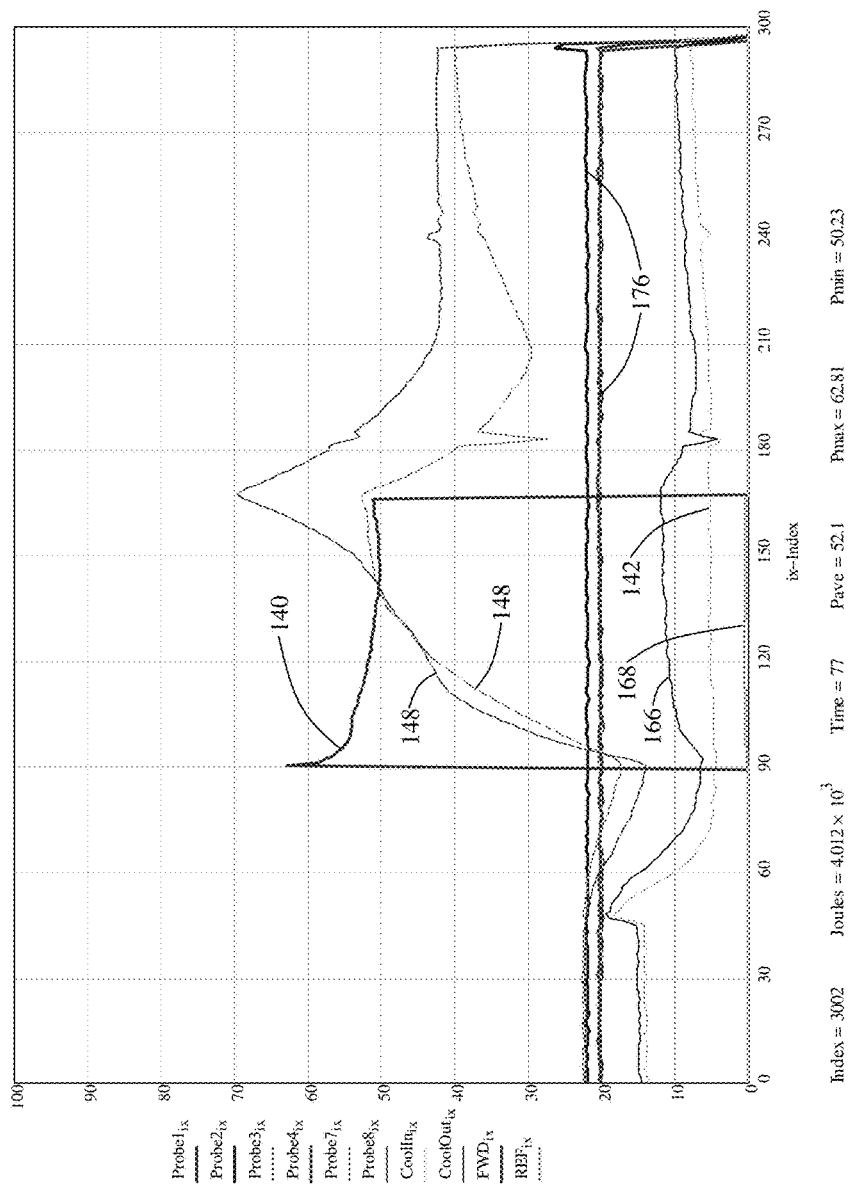

FIG. 23A is another cross section of a different NBT stained renal artery following the microwave renal denervation parameters shown in FIG. 23B. Label designators are as described above.

Figure 24A:
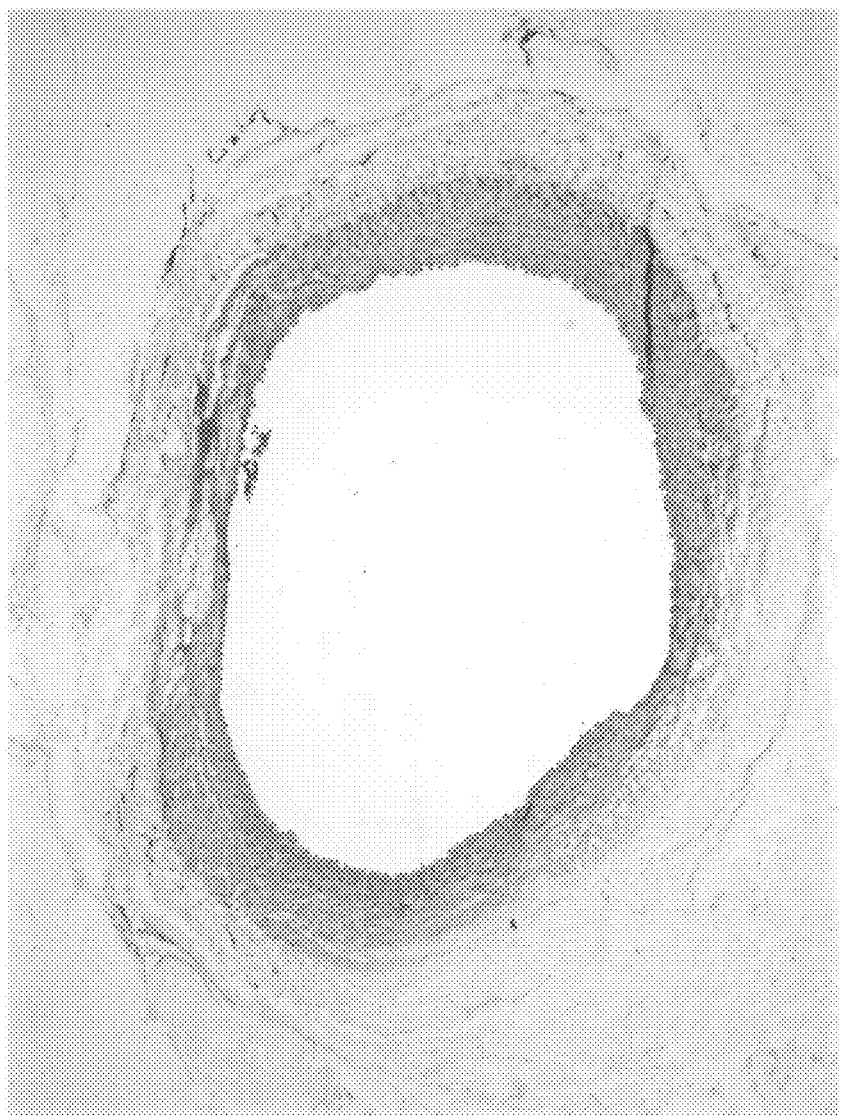
Figure 24B:
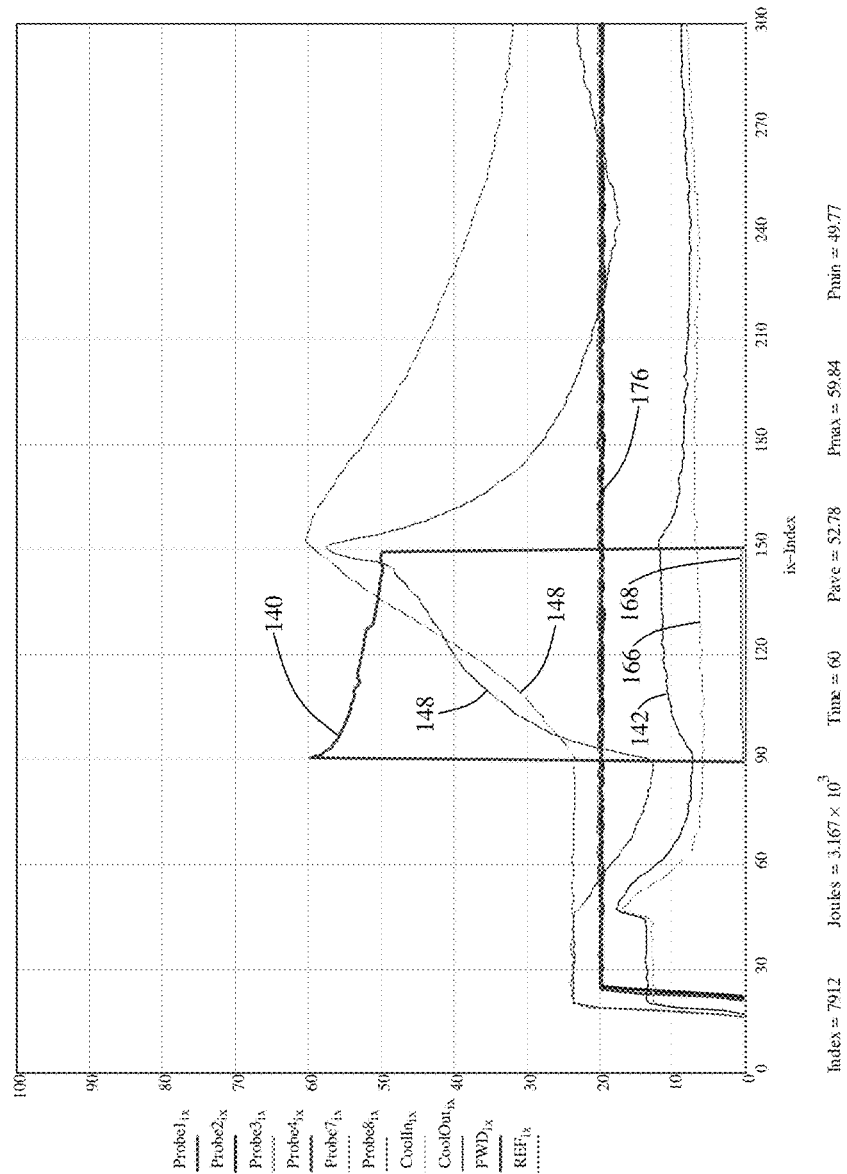

FIG. 24A is another cross section of a different NBT stained renal artery following the microwave renal denervation parameters shown in FIG. 24B. Label designators are as described above.

It should be noted that the empirical temperature data presented in FIGS. 20B-24B is data that does not necessarily capture the maximum tissue temperature that existed within the targeted adventitia and immediately adjacent surrounding tissue due to difficulty placing the small fiber optic thermometry sensors without expensive imaging instruments that were unavailable. As a result, temperatures recorded in FIG. 21B, for example, are lower than what was necessary to produce the corresponding histology slide depicted in FIG. 21A.

Figure 25:
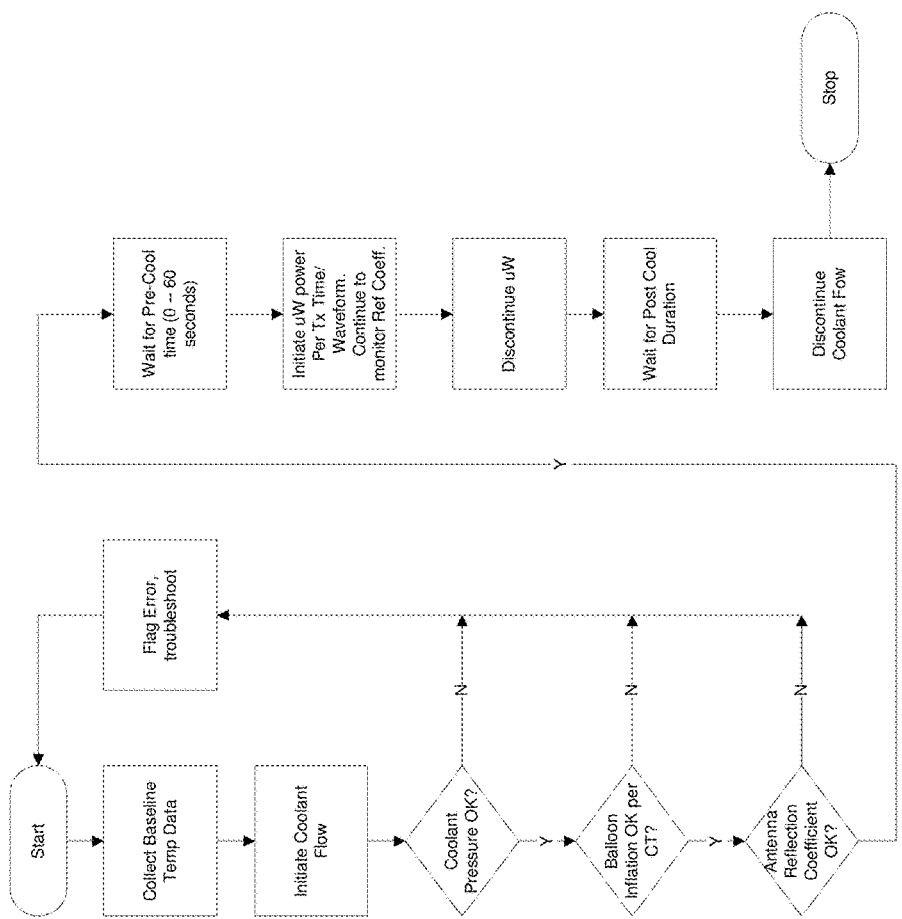
FIG. 25 is a flowchart illustrating treatment algorithm steps used to accomplish renal denervation.

FIG. 25 is a flowchart of the treatment algorithm used to accomplish renal denervation according to the present invention. The basic steps of a preferred embodiment include collecting baseline temperature data and logging it to a file prior to performing any step that will influence this data. Once baseline data is collected for later reference, coolant flow is initiated. Balloon 40 inflates due to the dynamic pressure from coolant flowing within interior region 41. Coolant pressure is measured typically within the coolant inlet port 26 to ensure proper inflation of balloon 40 and coolant pressure may be controlled passively with the use of a pressure regulator on the exhaust tubing port 28 exiting the microwave antenna containing catheter 10 or may be actively controlled with a closed loop feedback system that adjusts flow rate or a controllable restriction placed the output port 28 in accordance with an automatic control algorithm such as a Proportional Integral Derivative mode controller as known in the art.

Coolant pressure is verified to ensure proper operation as described above. Then the balloon 40 inflation will be verified using imaging such as fluoroscopy to ensure proper wall contact with intima 96 within renal artery 94. This ensures the intima 96 and media 98 will be protected from thermal injury during renal denervation.

A reflection coefficient of microwave antenna 46 is measured using techniques known in the art such as with the use of a dual directional coupler placed in the coaxial cable transmission line between the microwave generation source and antenna 46 within catheter 10. The reflection coefficient magnitude may be expressed as a linear ratio, in dB as the "return loss," as power with units such as Watts, or it may be expressed as a percentage of the excitation power. For convenience it is expressed in FIG. 20-24 in units of Watts and is very low. Typically, it is desired to keep the reflected power below 10% of the forward power for efficient and controlled microwave antenna operation as has been described in U.S. Pat. No. 5,300,099 and other sources.

With balloon inflation and reflection coefficient verified, coolant may be applied for additional time totaling (total time from initiation of coolant during the prior verifications) essentially one to 60 seconds (or not at all in some alternative embodiments). In the histology study this time was typically 30 seconds.

Figure 27:
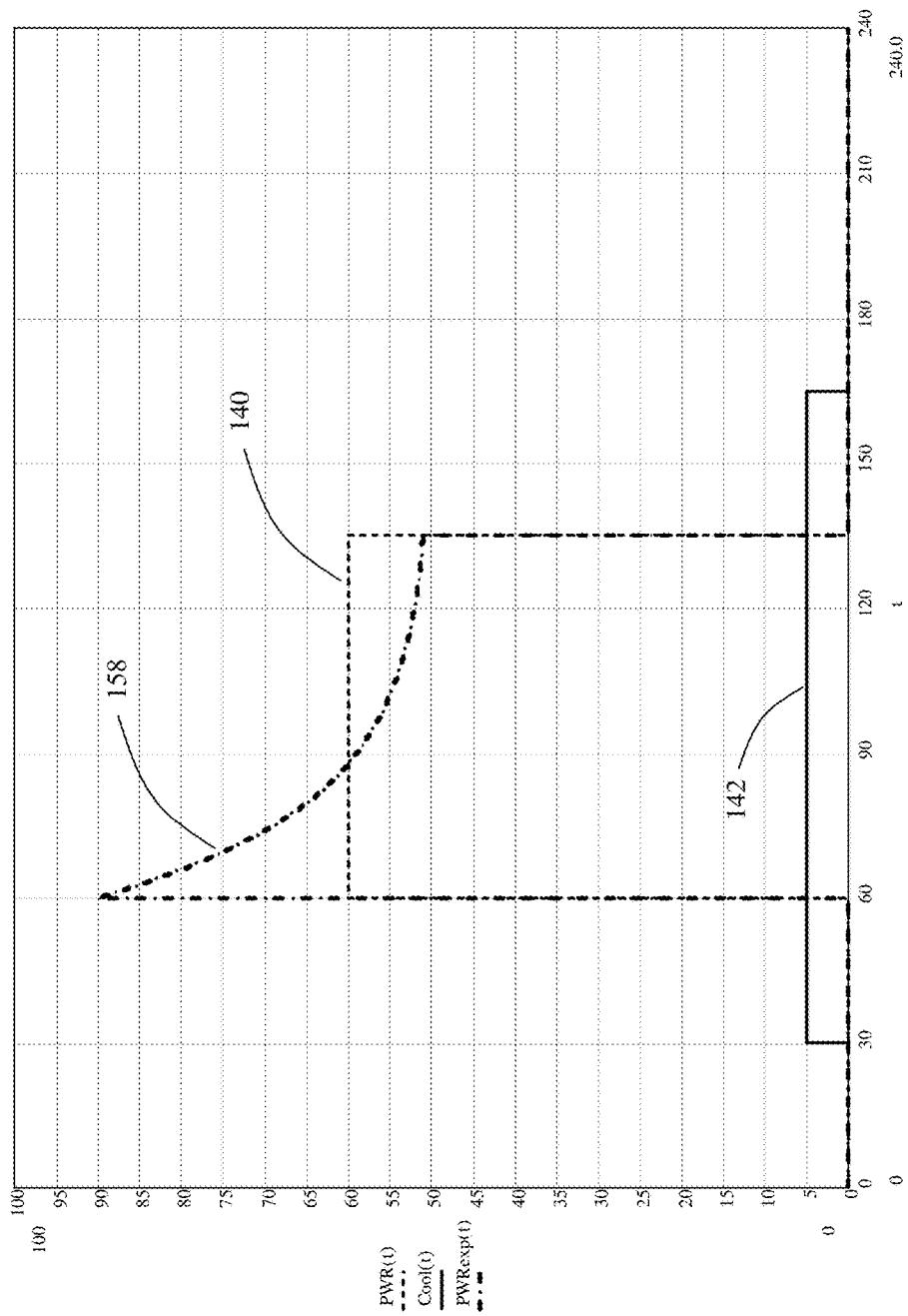
FIG. 27 is a graph of alternate treatment parameters for accomplishing renal denervation using an exponentially decaying microwave power function.

Once the coolant time has completed, microwave power may be applied as a fixed value for a period of time, as a time varying function such as the exponential decay function graphed in FIG. 27, or as the result of a Proportional Integral Derivative mode controller that adjusts power automatically to achieve a desired control variable such as temperature. Since the duration of applied microwave power is very short and ranges up to around 180 seconds it is advantageous to use one of the waveforms in FIG. 27 to be described later.

The microwave power is then discontinued after the previous step. Cooling flow is continued for from one to 60 seconds (or alternatively not at all in some embodiments) to continue to protect the intima and media as the high temperature in the surrounding advantitia tissue dissipates safely without elevating intima temperature or media temperature. Coolant flow may then be stopped, balloon deflation checked, and the renal denervation is complete for this artery and may be performed in the opposite renal artery as needed.

Figure 26:
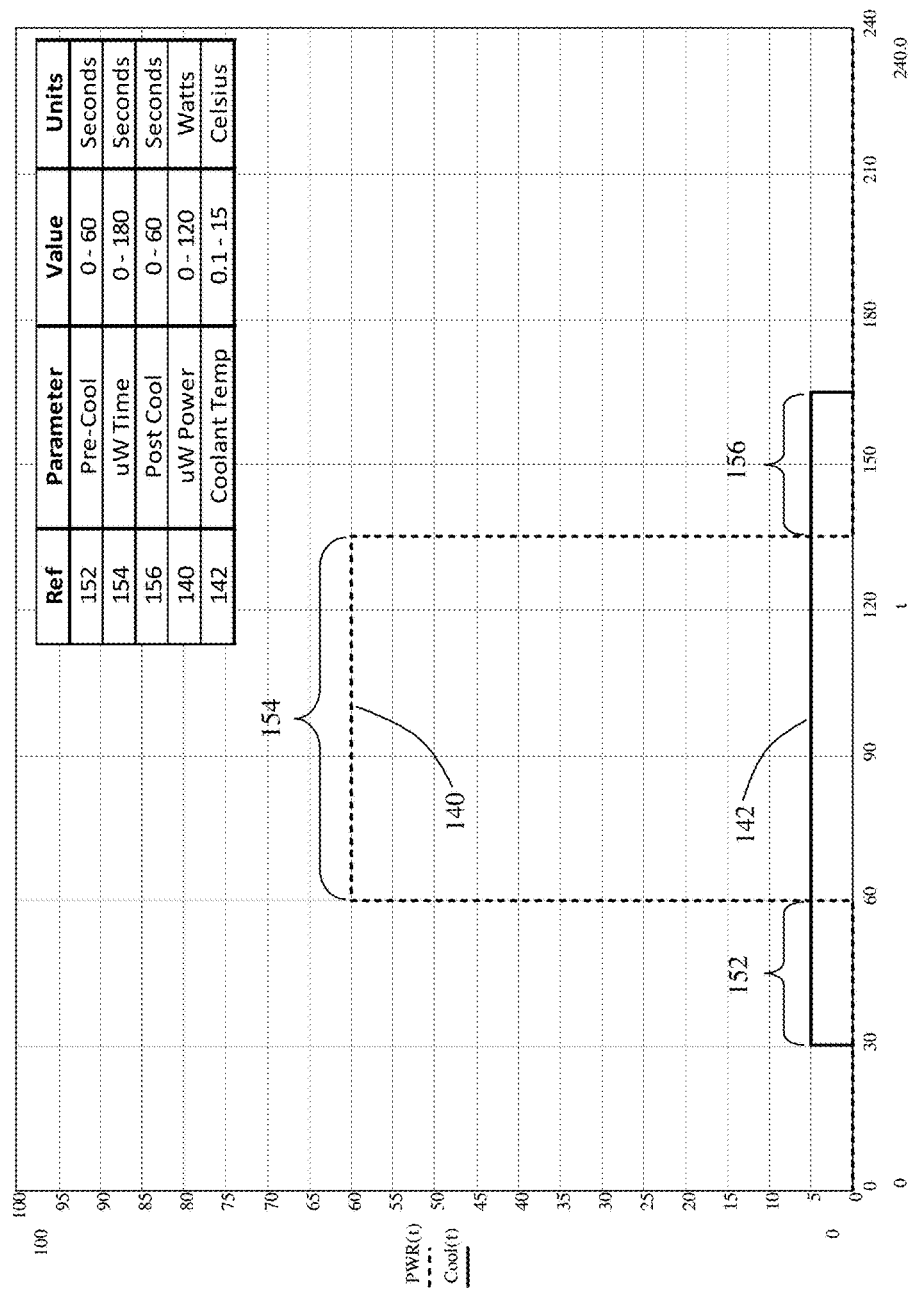
FIG. 26 is a graph of treatment parameters for accomplishing renal denervation using constant applied microwave power and constant coolant temperature.

FIG. 26 is a graph of treatment parameters using a constant applied microwave power (140) of 60 Watts and a constant applied coolant temperature (142) of 5° C. for example. The applied microwave power duration (154), coolant pre-cool duration (152) and coolant post-cool duration (156) are identified on the plot. The inset table includes preferred ranges for these parameters. The small zone of thermal injury desired to precisely target the renal nerves is best achieved with the use of relatively high power (60 Watts) for a short duration (60-75 seconds) with coolant near the ice point of water at 5° C. or cooler. This short exposure prevents the thermal injury from propagating further due to thermal conduction and damaging adjacent tissue. It minimizes or eliminates the influence of local tissue perfusion on the resulting temperature field and thermal injury zone, and it is convenient and desirable to keep the treatment time as short as possible.

FIG. 27 is a graph of an alternate microwave power profile as a function of time. 158 is an exponential decay function of microwave power and it is an advantage over the fixed power 140 because it accelerates heating when the intima temperature is lowest but slows heating as the intimal temperature approaches its final value for greater control. This has the overall effect of reducing the time necessary for microwave duration and keeps the thermal injury tightly controlled.

Antenna Embodiments

Figure 28:
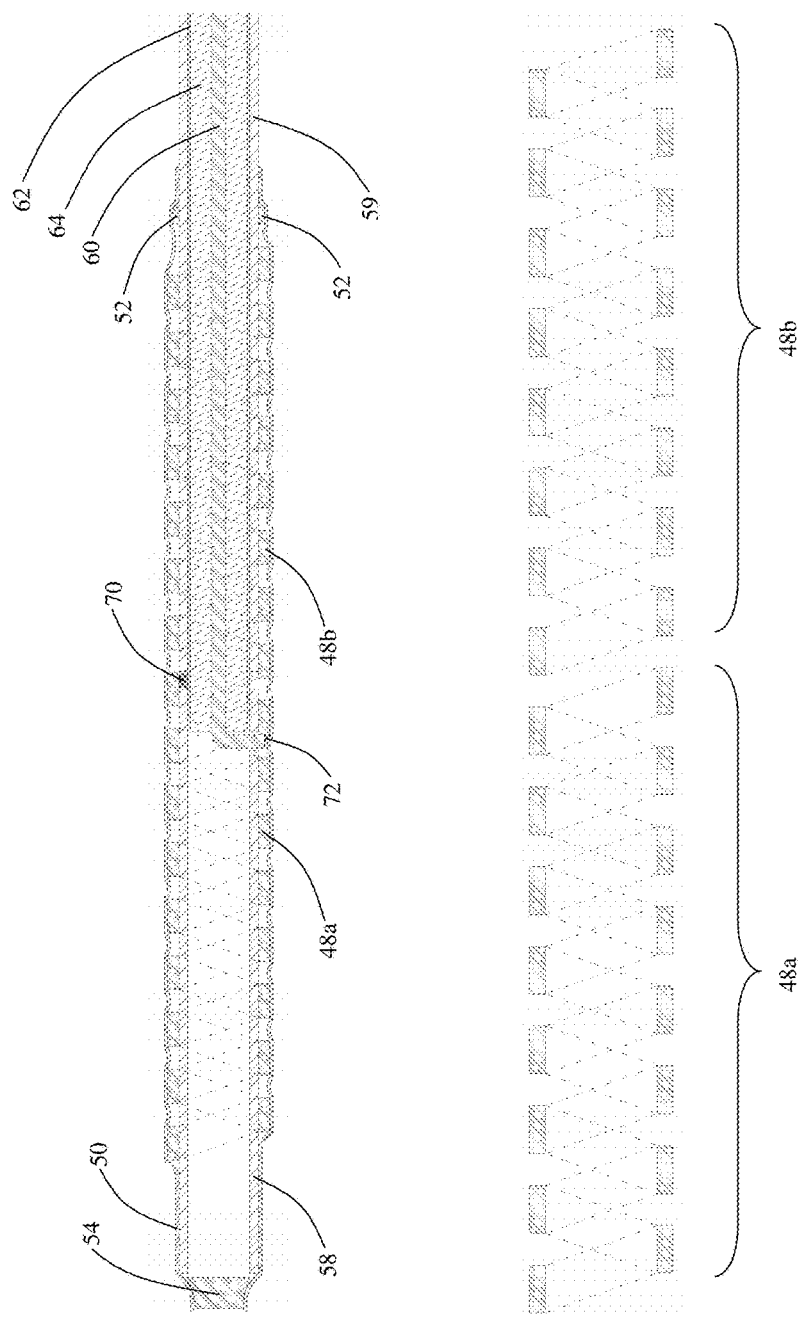
FIG. 28 is a diagram of an antenna embodiment suitable for microwave renal denervation that uses two separate antenna coils.

FIG. 28 is a diagram of an antenna particularly suited for renal denervation. It is comprised of two antenna coils, 48*a* and 48*b*, where coil 48*a* is connected to the center conductor 60 of coaxial cable 30 at location 72 and coil 48*b* is connected to the outer conductor 62 of coaxial cable 30 at location 70. A tubular extension, 58, provides support for coil 48*a*. Thin wall shrink 50 compresses against both coils and keeps them mechanically aligned and it seals against antenna plug 54 and antenna gasket 52 that may be fabricated of silicone rubber to keep the circulating coolant from directly touching coils 48*a* and 48*b*. Coaxial cable 30 also has jacket 50 and dielectric 64. This antenna can be configured to create a single maximum SAR at the "gap" between coil 48*a* and 48*b* and is suitable for achieving renal denervation.

Figure 29:
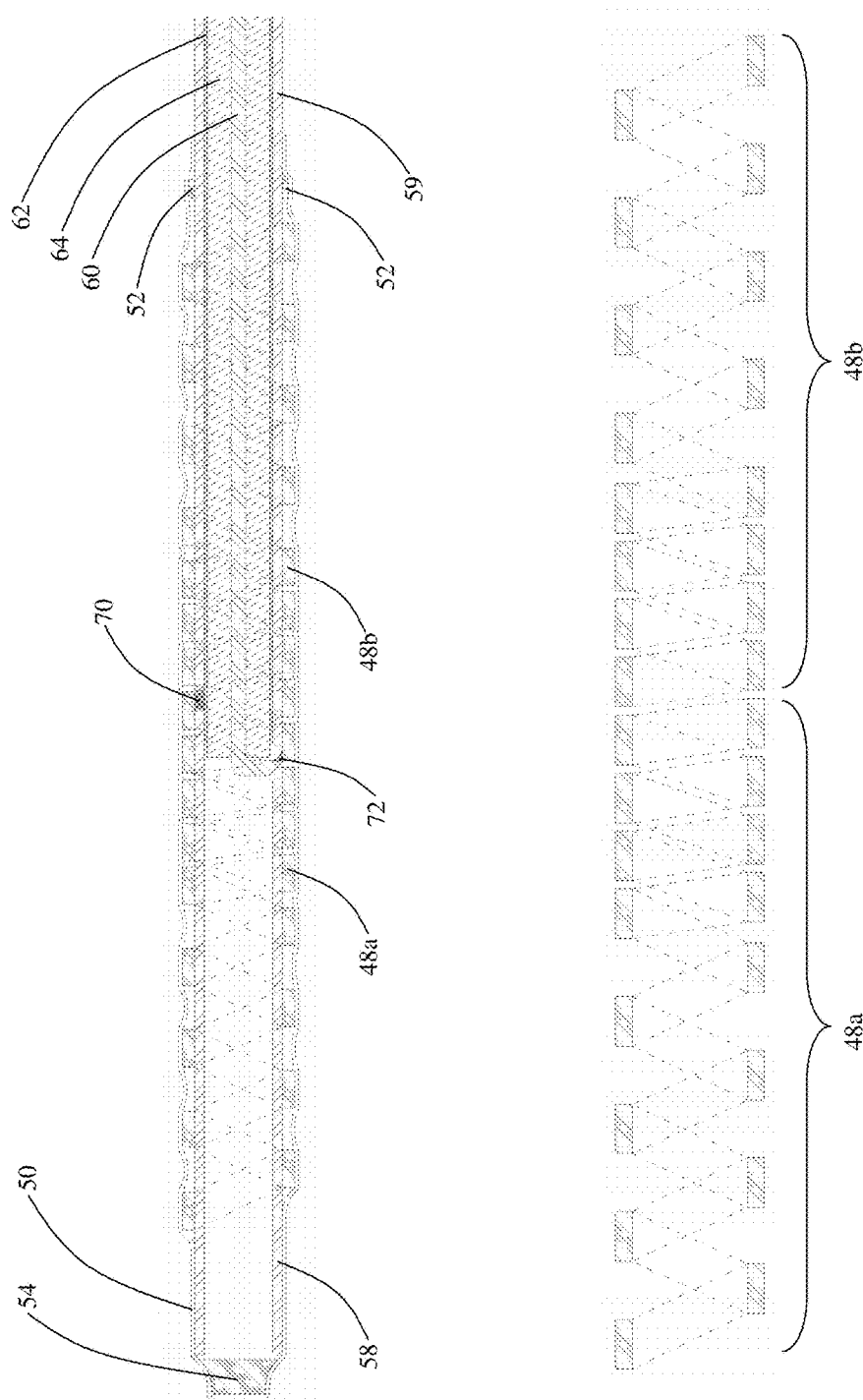
FIG. 29 is a diagram of an alternate antenna embodiment suitable for microwave renal denervation that uses two separate antenna coils.

FIG. 29 is a diagram of an additional antenna embodiment in with coil 48*a* and 48*b* have non uniform pitch. The non uniform pitch has the effect of narrowing the SAR peak to accommodate the geometry necessary for renal denervation. As described in FIG. 28, all reference numbers are the same.

Figure 30:
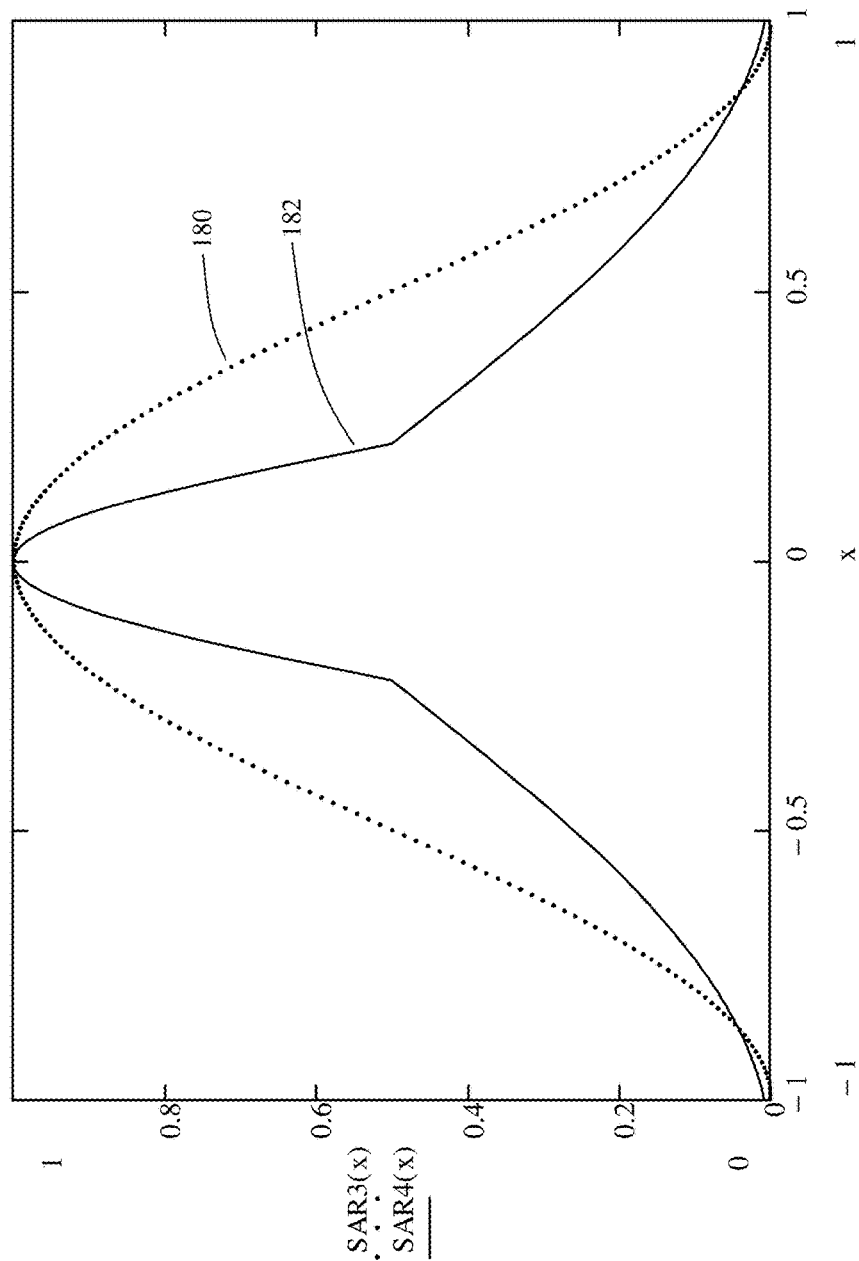
FIG. 30 is a graph of a normalized SAR pattern for the dual coil antenna embodiments depicted in FIGS. 28 and 29.

FIG. 30 is a graph of a SAR plot for the antenna in FIG. 28 (180) and the antenna in FIG. 29 (182). The single peak in SAR (180) may be adjusted in length according to the coil pitch and may be narrowed further by making the coil pitch non uniform (182).

Figure 31:
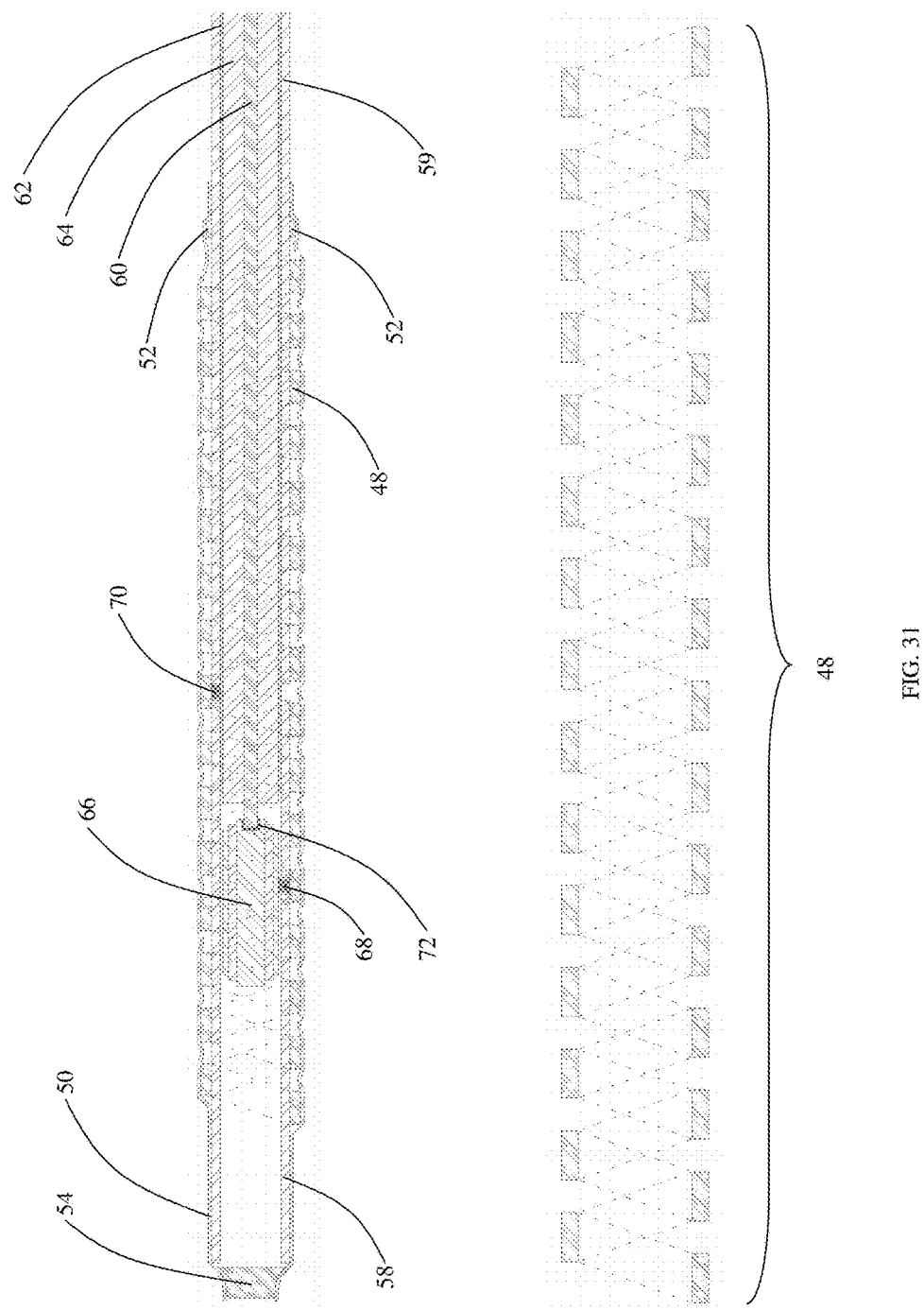
FIG. 31 is a diagram of the antenna embodiment as described in U.S. Pat. No. 5,300,099.

FIG. 31 is a diagram of the antenna described in detail in U.S. Pat. No. 5,300,099. Components include matching capacitor 66, antenna coil 48, and tubular extension 58. Shrink tubing 50 seals against gasket 52 and antenna plug 54 to keep cooling fluid from directly touching antenna coil 48. Center conductor 60 of coaxial cable 30 is connected to matching capacitor 66 at 72. Matching capacitor 66 is connected to coil 48 at 68 to form a "tap point" as described in U.S. Pat. No. 5,300,099. This antenna produces a SAR field with two equal maximums and is ideally suited for treating a prostate, kidney, liver, or other organ where a very large volume of thermal injury (may be 20 cubic centimeters or more) is desired and treatment times of 10 to 60 minutes are acceptable. However, the following adaptations to this basic design make it more suitable for renal denervation.

Figure 32:
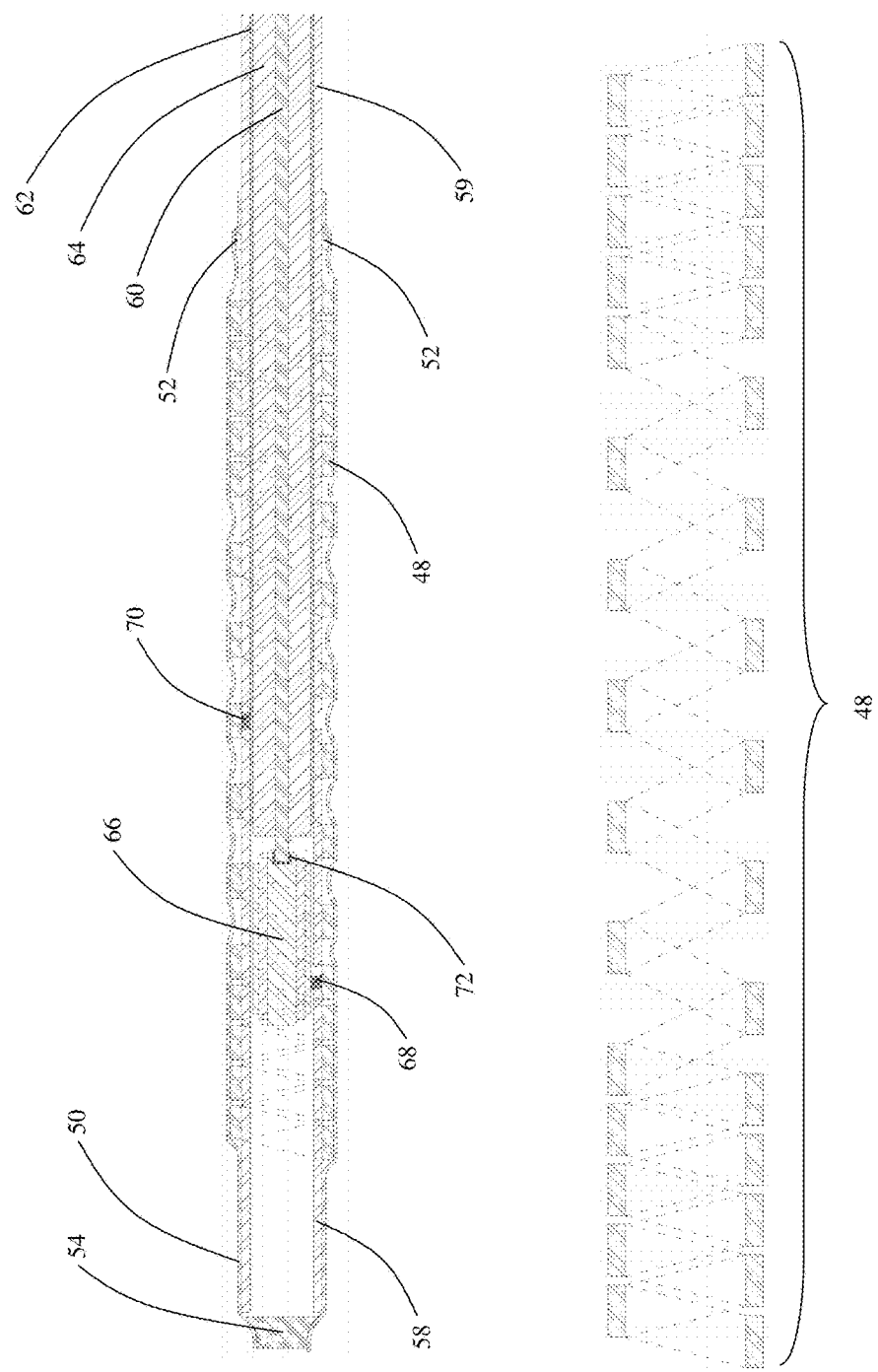
FIG. 32 is a diagram of a modification to the embodiment depicted in FIG. 31 to enable the creation of two narrow circumferential thermal injury zones for microwave renal denervation.

FIG. 32 is a diagram of a modification to the antenna of FIG. 31 to provide two very narrow SAR maximum zones. It has two regions of narrow pitch at each end of coil 48. Other features are as described above. This antenna is capable of producing two separated rings of thermal injury and may be particularly useful to accomplish renal denervation as a second narrow ring of thermal injury will make nerve regeneration even more unlikely as nerves would need to "find" each other through two zones of injury.

Figure 33:
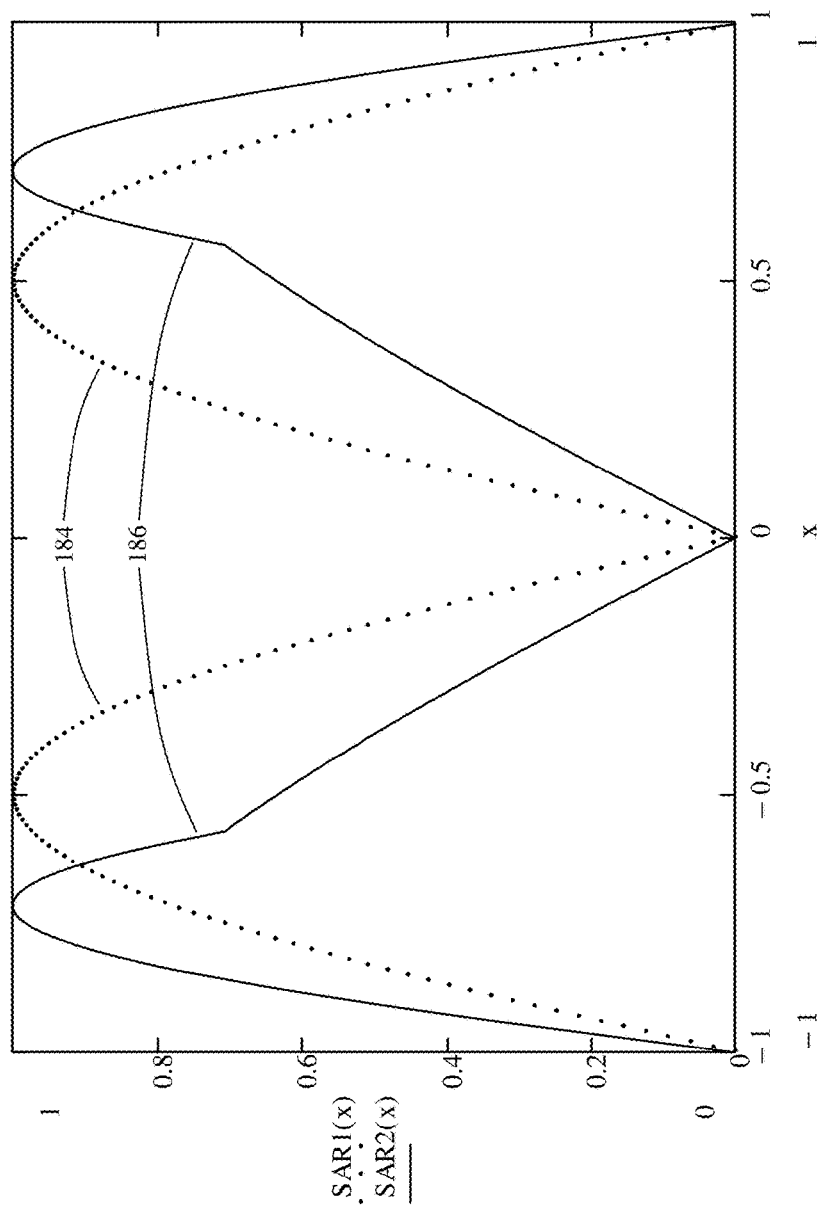
FIG. 33 is a graph of a normalized SAR pattern for the antenna embodiments depicted in FIGS. 31 and 32.

FIG. 33 is a graph of a SAR plot for the antennas of FIGS. 31 and 32 described above. SAR curve 184 is for the antenna of FIG. 31 as described in U.S. Pat. No. 5,300,099. SAR curve 186 is for the modified antenna of FIG. 32. It can be easily visualized that this modification results in more separated, narrower SAR peaks ideally suited for renal denervation to produce two separate zones of injury to the renal nerves.

Figure 34:
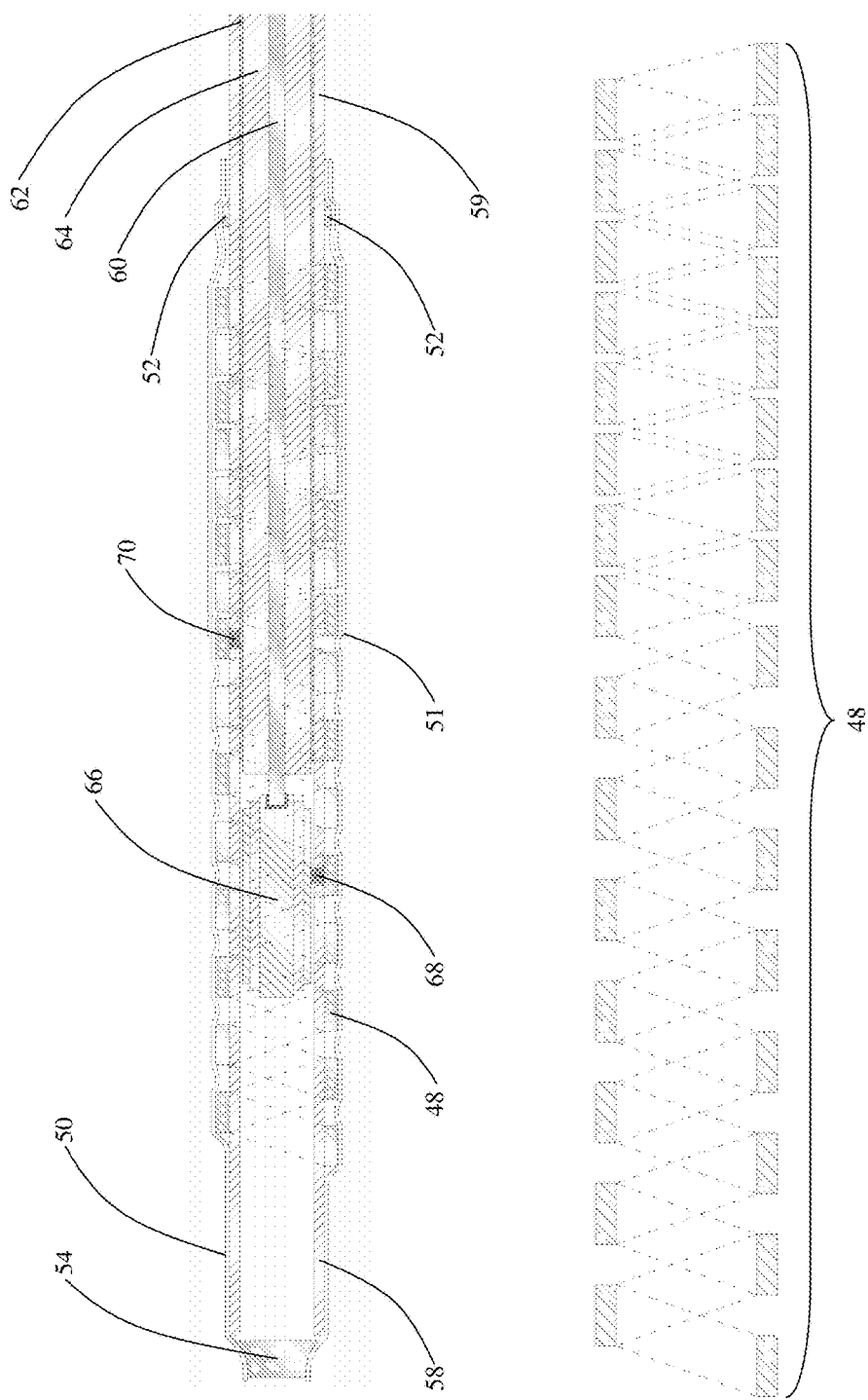
FIG. 34 is a diagram of an additional alternate modification to the embodiment depicted in FIG. 31 to enable the creation a single narrow circumferential thermal injury zone for microwave denervation.

FIG. 34 is a diagram of a further adaptation to the antenna of FIG. 31 as described above and in U.S. Pat. No. 5,300,099. It incorporates a second layer of shrink, 51, to increase the thickness of dielectric shrink material between coil 48 and coolant occupying region 39 within catheter 10. This changes the electrical loading due to the near field dielectric and creates an asymmetry in the SAR peaks. For the applications discussed in U.S. Pat. No. 5,300,099 this is undesirable but for renal denervation this can be utilized to emphasize SAR from one element of 48 so much that the SAR contribution from the second element will not produce thermal injury. An antenna configured with this modification will accordingly create a single narrow region of thermal injury that may be of particular advantage for accomplishing renal denervation.

An additional enhancement of this effect is to narrow the pitch of the proximal winding of antenna coil 48 such that the enhanced SAR produced as described above will be further concentrated along a shorter radiation length.

Figure 35:
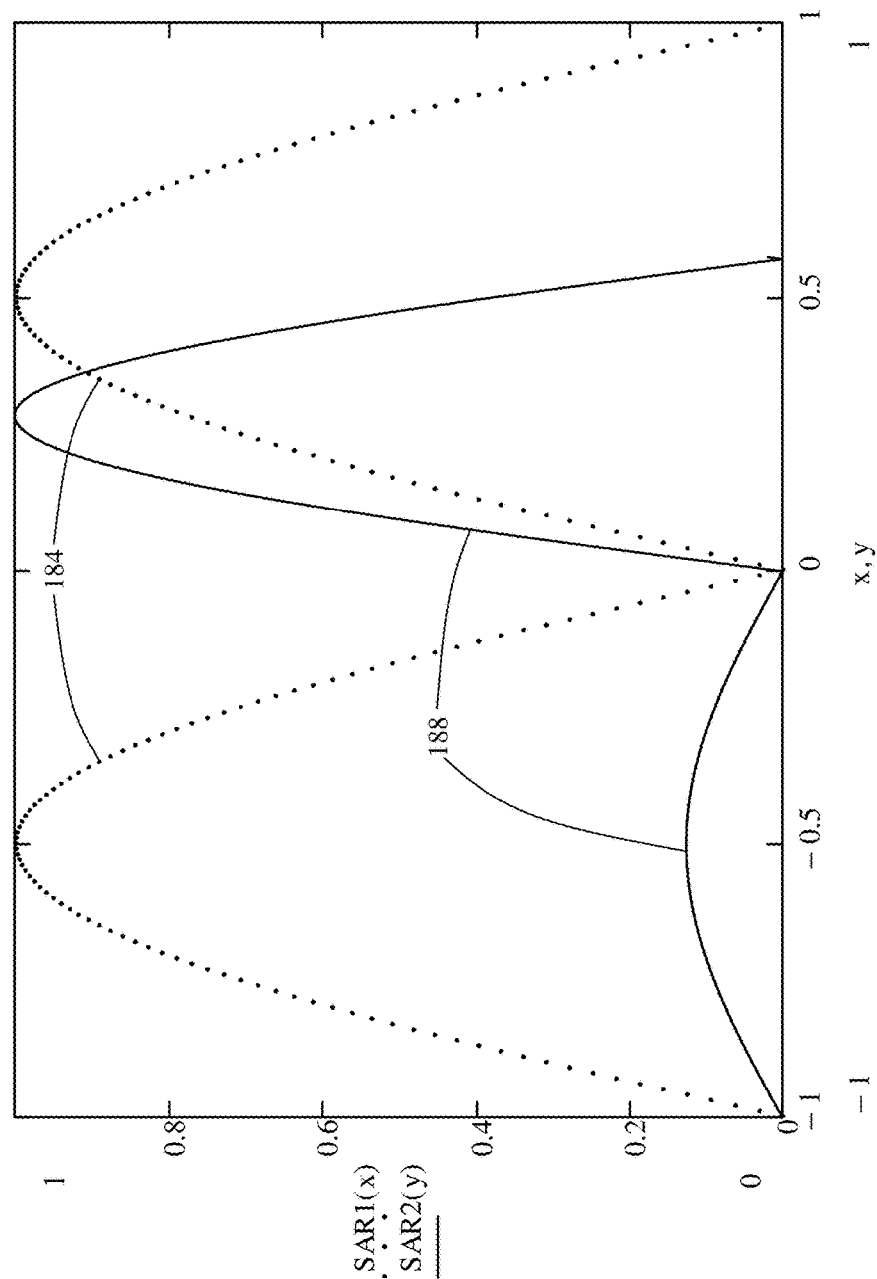
FIG. 35 is a graph of a normalized SAR pattern for the antenna embodiments depicted in FIG. 31 and FIG. 34.

FIG. 35 is a graph of a SAR plot for the antennas depicted in FIG. 31 (184) and in FIG. 34 (188). It can be easily visualized that the distal SAR peak has been minimized to a non-significant level and the essentially single remaining SAR peak has been made narrower. This SAR distribution will accomplish renal denervation in shorter renal arteries than is possible with the unmodified antenna of FIG. 31 as described above and in U.S. Pat. No. 5,300,099.

FIG. 36 is a diagram of an alternate antenna embodiment adapted to place the antenna coil in the cooling balloon 40 rather than within the catheter body wall. This adaptation was applied to the antenna shown in FIG. 28 for illustration but may be applied to any other antenna described above.

Inner body wall 22 is sized to create interior region 39 for cooling flow between tubular extension 58 and coaxial cable jacket 59 and the inner surface of inner body wall 22. Center conductor 60 of coaxial cable 30 is connected to antenna coil 48a at connection 72, and outer conductor 62 of coaxial cable 30 is connected to coil 48b at connection 70 as described above, but in this adaptation sealant adhesive 53 is applied to seal the connections and prevent water from entering coaxial cable 30 or the region between inner body wall 22 and antenna shrink 50 where antenna coils 48a and 48b are located. An additional gasket 52, for a total of two (2) gaskets, is configured to seal antenna shrink 50 to inner body wall 22 at both ends of antenna coil 48a and 48b. Adhesive sealant 53 is also applied within tubular extension 58 to also keep coolant out of coaxial cable 30. Coolant ports 44 allow coolant to flow from region 41 within balloon 40 and inner region 39 between tubular extension 58 and inner body wall 22.

Additional Catheter Embodiments

Figure 37:
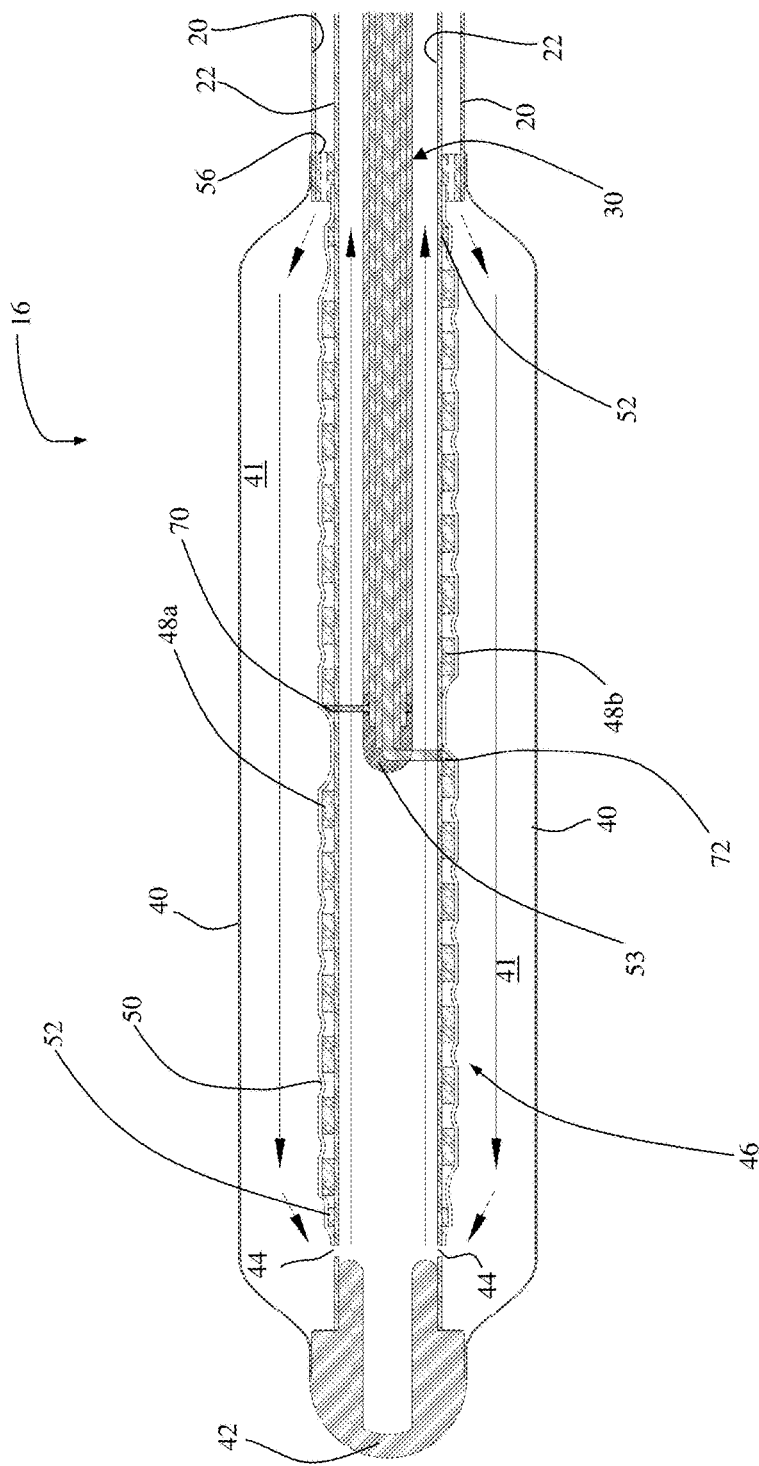
FIG. 37 is a more detailed diagram of the device embodied in FIG. 1F. It includes details of the antenna depicted in FIG. 36 and the inner wall has been re-scaled to better illustrate cooling flow.

FIG. 37 is a more detailed diagram of the device embodied in FIG. 1F, depicting an embodiment of catheter 10 that locates antenna coil 48 within balloon 40 as in FIG. 1F. Coolant flows between inner body wall 22 and outer body wall 20, through spacer 56, and into interior region 41 formed by balloon 40 as before. Antenna coil windings 48a and 48b are placed within this region as well, separated only by shrink tubing 50 from coolant 41 within. The outer conductor of coaxial cable 30 is connected to proximal antenna winding 48b through connection 70. The inner conductor of coaxial cable 30 is connected to distal antenna winding 48a through connection 72. The end of coaxial cable 30 is sealed with potting adhesive 53 to prevent coolant ingress. Coolant flows through ports 44 and between the jacket of coaxial cable 30 and inner body wall 22 within the antenna.

Figure 38:
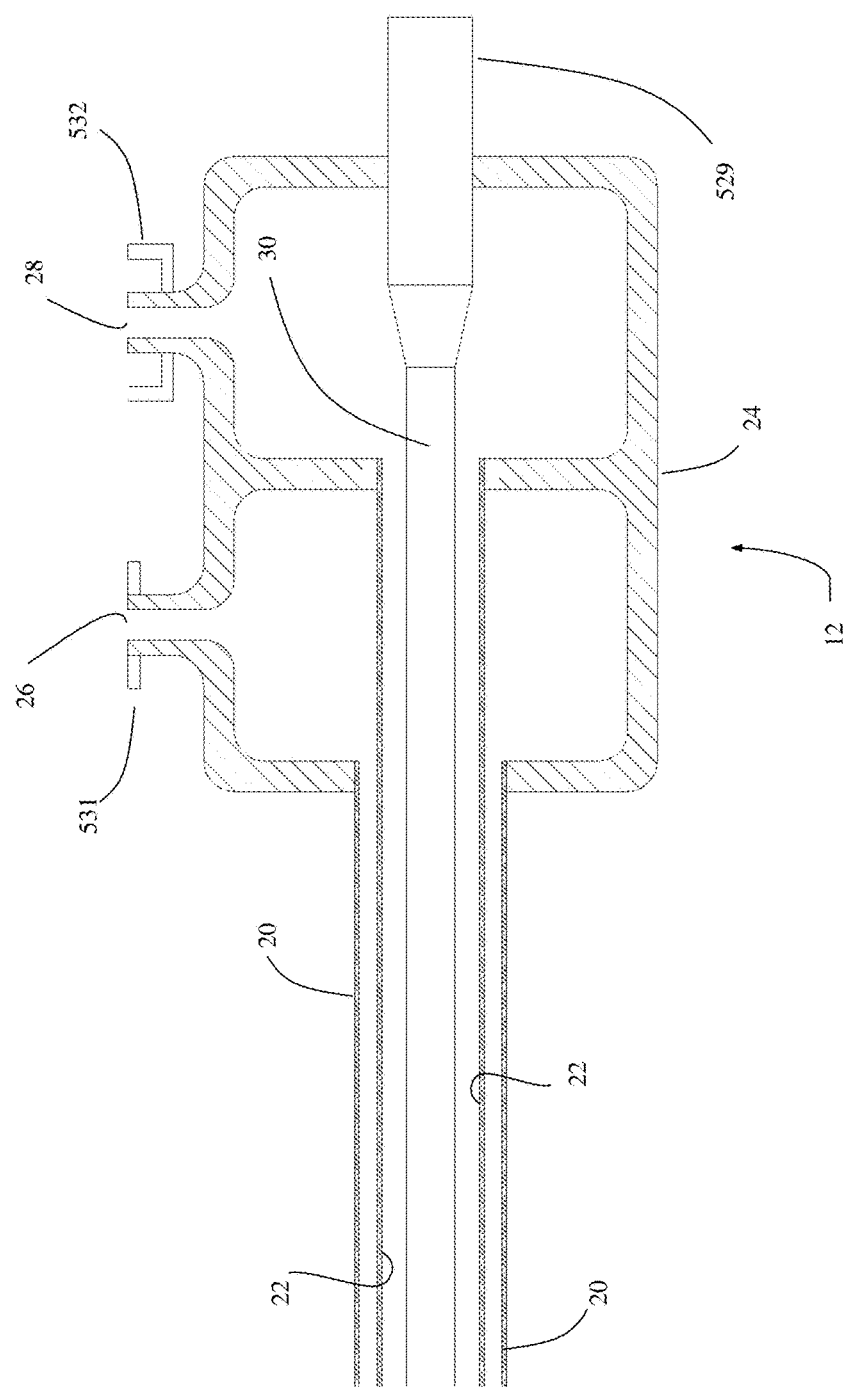
FIG. 38 is a revised diagram of the device embodied in FIG. 1B. It includes the re-scaled inner wall as in FIG. 37 to better illustrate cooling flow.

FIG. 38 is a revised diagram of the device embodied in FIG. 1B and scaled to be compatible with the embodiment described in FIG. 37. It includes the re-scaled inner wall as in FIG. 37 to better illustrate cooling fluid flow. Cooling fluid enters port 26 through tubing or a fluid connector 531 such as a female Luer connector, and enters the input chamber of manifold body 24. From there, coolant flows through the space between the inner catheter wall 22 and outer catheter wall 20 down to distal portion 16 of microwave antenna carrying catheter 10. After the coolant circulates through distal portion 16 as described above, it returns through the space between inner catheter wall 22 and coaxial cable 30 and enters the exhaust chamber of manifold body 24. From there it exits through port 28 through tubing or a fluid connector 532 such as a male Luer connector. Alternately, it may be desirable for coolant to flow in the reverse direction to manage pressure drop and/or minimize heat rise prior to entering the interior of cooling balloon 41 at the distal portion 16 of microwave antenna carrying catheter 10. Coaxial cable 30 may exit manifold body 24 or may be terminated with RF connector 529, such as a male SMA connector, mounted directly on manifold body 24.

Figure 39:
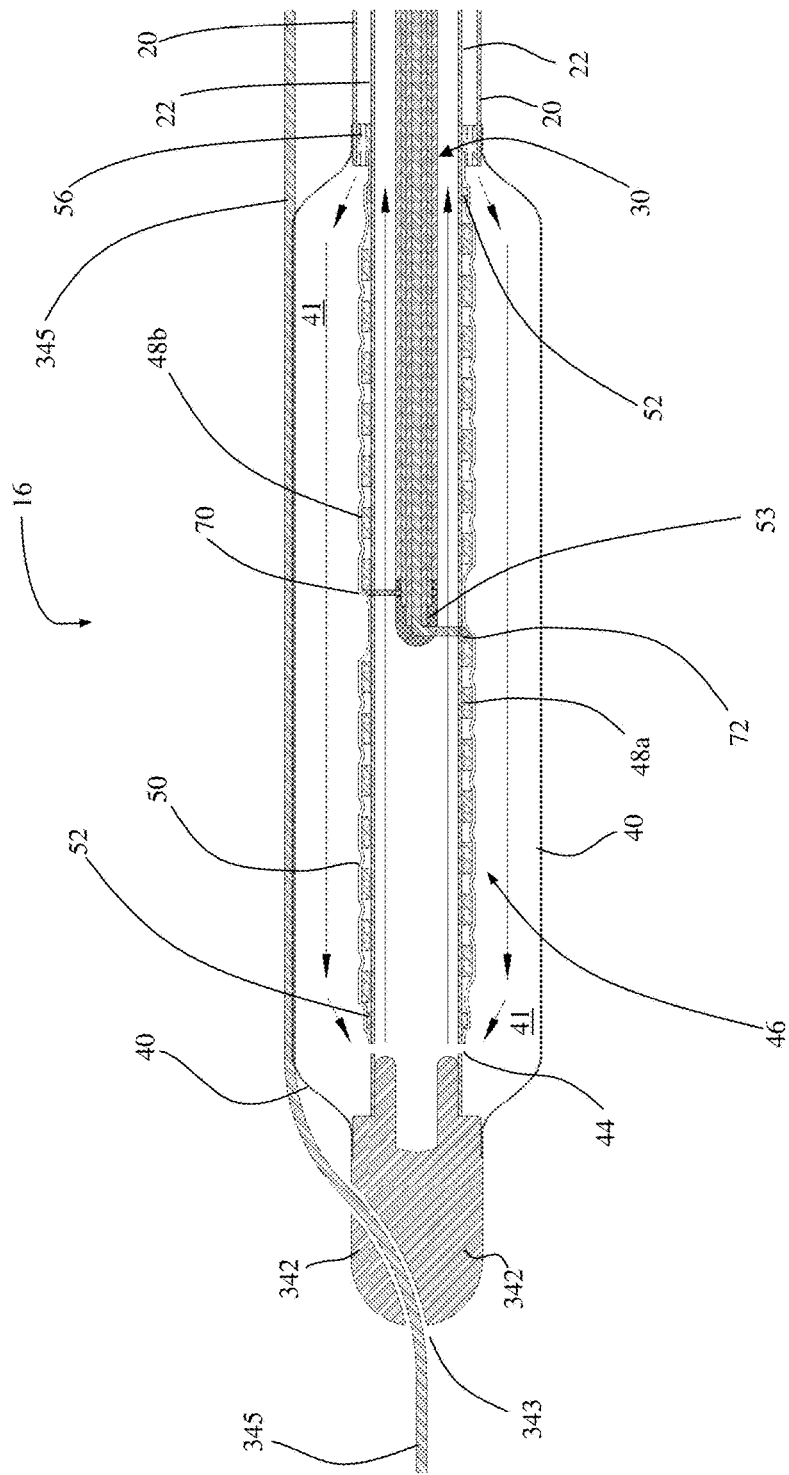
FIG. 39 is a diagram of a tip embodiment that is compatible with a guide wire to allow introduction and positioning with a guide wire instead of or in addition to a guide catheter as may be preferred by certain physicians.

FIG. 39 is a diagram of a tip embodiment that is compatible with a guide wire to allow introduction and positioning with a guide wire instead of or in addition to a guide catheter as may be preferred by certain physicians. Such a tip is sometimes referred to as a "monorail" tip. Tip 342 connects with balloon 40 and catheter wall 22 and/or catheter wall 20 as before. However, tip 342 includes channel 343 through which guide wire 345 may pass. This enables microwave antenna containing catheter 10 to track guide wire 345 previously placed using well adopted procedures. Guide wire 345 may be retracted past balloon 40 or removed prior to initiating the denervation procedure to avoid interfering with the microwave field or cooling.

Figure 40:
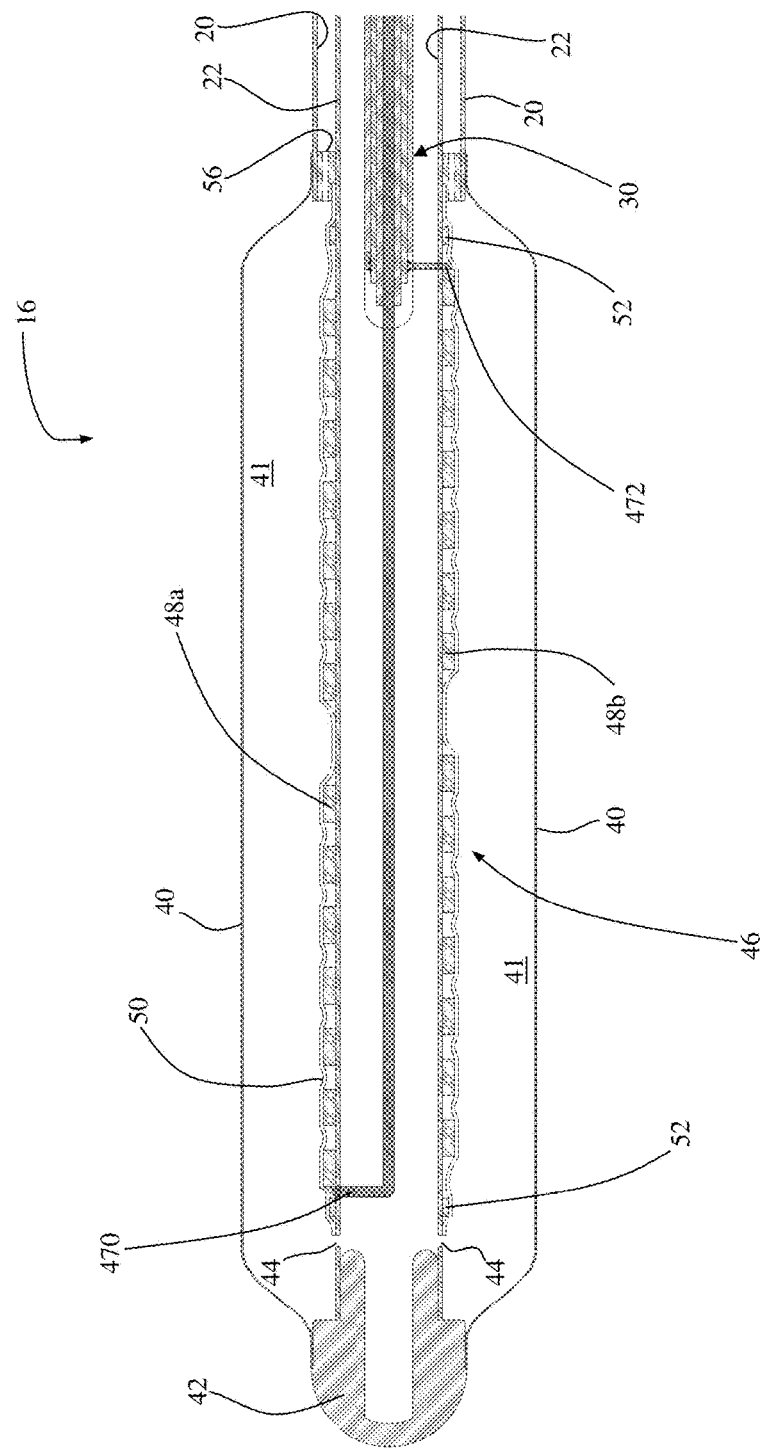
FIG. 40 is a diagram of an end-fed antenna embodiment.

FIG. 40 is a diagram of an end-fed antenna embodiment. In this antenna embodiment, the distal end of distal coil winding 48a is attached to the center conductor of coaxial cable 30 by interconnect 470. The proximal end of distal coil winding 48a is unconnected. The proximal end of proximal antenna coil winding 48b is connected to outer the outer conductor of coaxial cable 30 through connection 472. The distal end of proximal coil winding 48b is unconnected. The coaxial cable is sealed using potting adhesive 53, and additionally potting adhesive may be used to isolate connections 470 and 472 from the coolant. Catheter inner and outer wall 22 and 20, spacer 56, balloon 40, tip 42 and coolant ports 44 function as described previously.

Figure 41A:
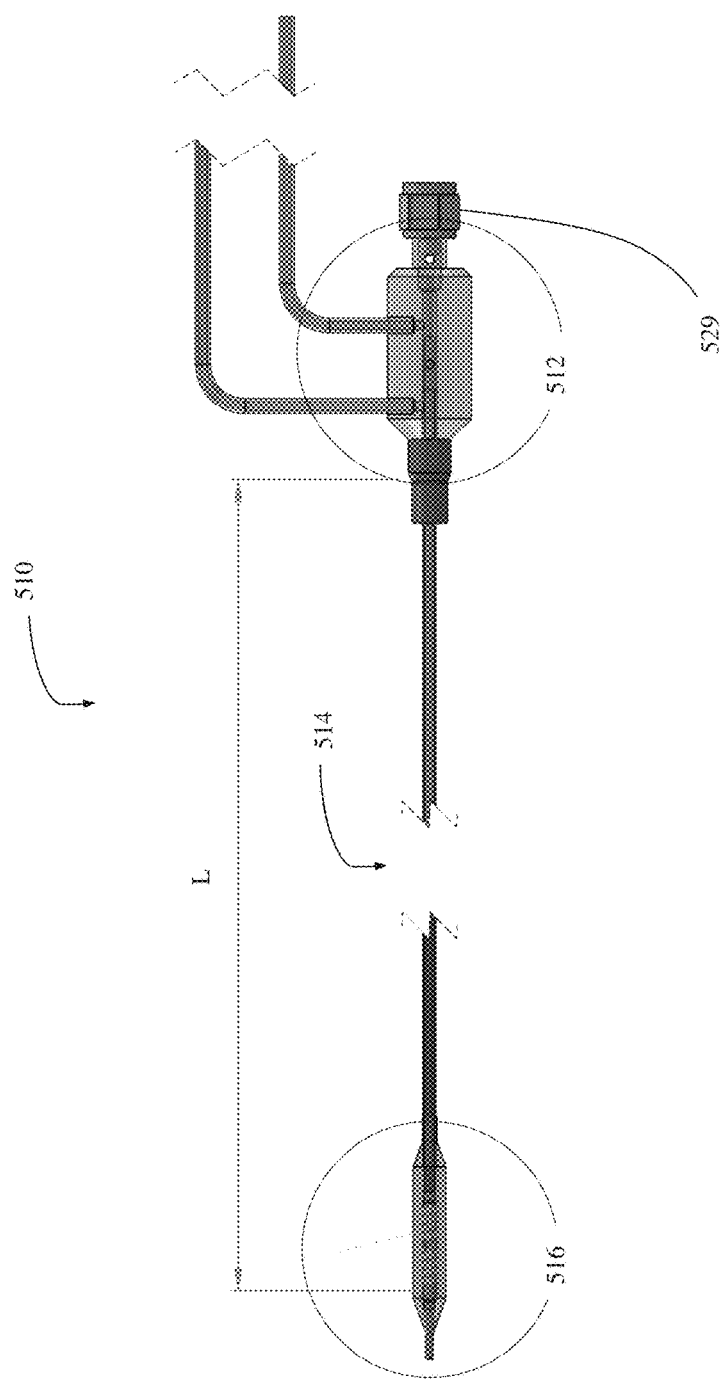
FIGS. 41A-41D are drawings of a catheter embodiment as fabricated for testing.

FIG. 41A depicts the entire microwave antenna carrying catheter 510 as fabricated and tested in an exemplary embodiment. Catheter 510 fits through an off-the-shelf 8 French renal guide catheter. Distal portion 516 of catheter 510 incorporates the antenna and cooling balloon. Middle portion 514 of catheter 510 is comprised of the flexible catheter tubing and coaxial cable. Proximal portion 512 of catheter 510 is comprised of a manifold, strain relief, coolant tubing, and coaxial connector as is illustrated in FIG. 41D. Length L may be adjusted as needed to provide a convenient working distance but it is desirable to keep it as short as possible to mitigate coaxial cable loss, coolant pressure drop, and coolant temperature warming due to heat absorption along the length of the catheter.

Figure 41B:
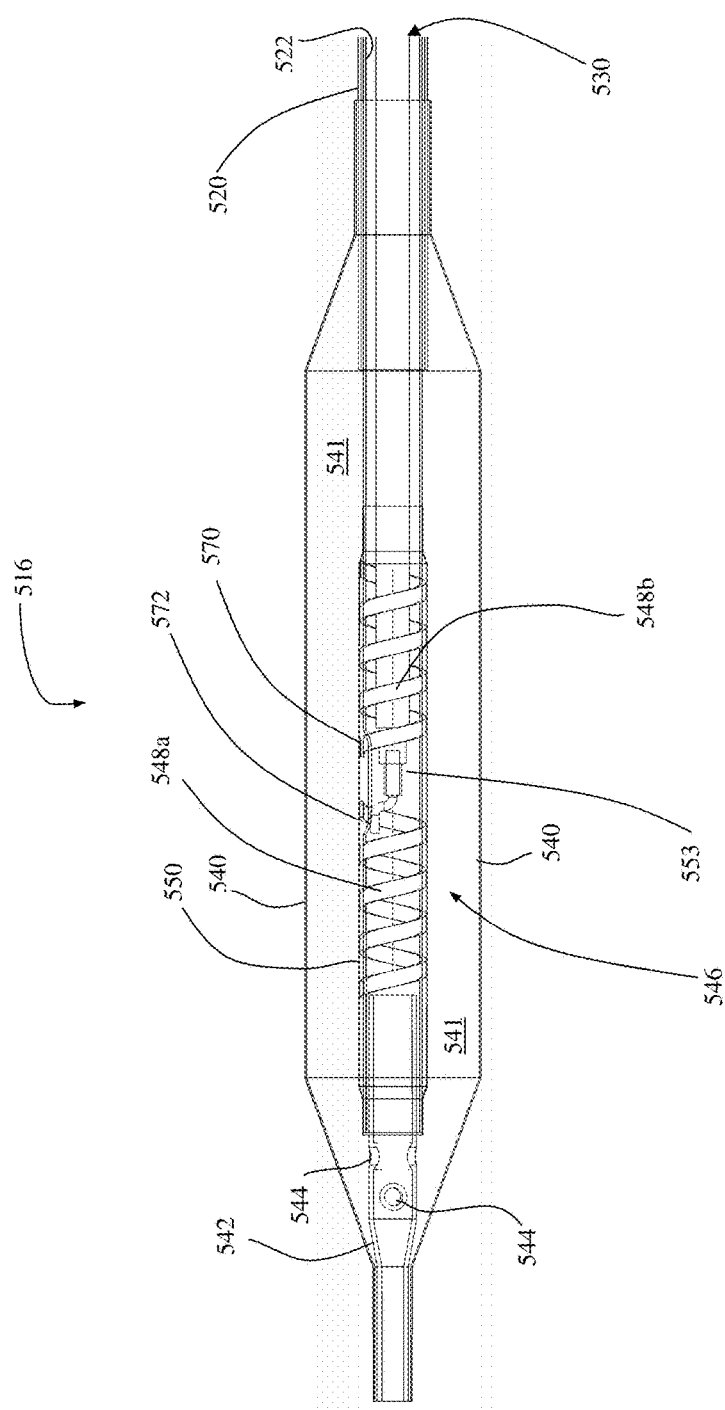

FIG. 41B depicts distal portion 516 of microwave antenna carrying catheter 510 in detail. As described previously, coolant flows between outer catheter wall 520 and inner catheter wall 522 and enters interior chamber 541 of balloon 540. Balloon 540 inflates due to coolant pressure and contacts the artery wall (not shown). Coolant flows through ports 544 of tip 542 and into the space between inner catheter wall 522 and coaxial cable 530. Coolant returns to proximal portion 512 of microwave antenna carrying catheter 510 through the region between coaxial cable 530 and inner catheter wall 522. Alternately, coolant may flow in the opposite direction as described previously. Distal and proximal antenna winding coils 548a and 548b, respectively, are wound about inner catheter wall 520. Thin shrink material 550 surrounds antenna coils 548a and 548b to isolate these coils from the coolant in interior chamber 541. The center conductor of coaxial cable 530 is attached to distal coil 548a at connection 572. The outer conductor of coaxial cable 530 is attached to proximal coil 548b at connection 570. These connections are sealed with potting adhesive 553 to prevent fluid ingress.

Figure 41C:
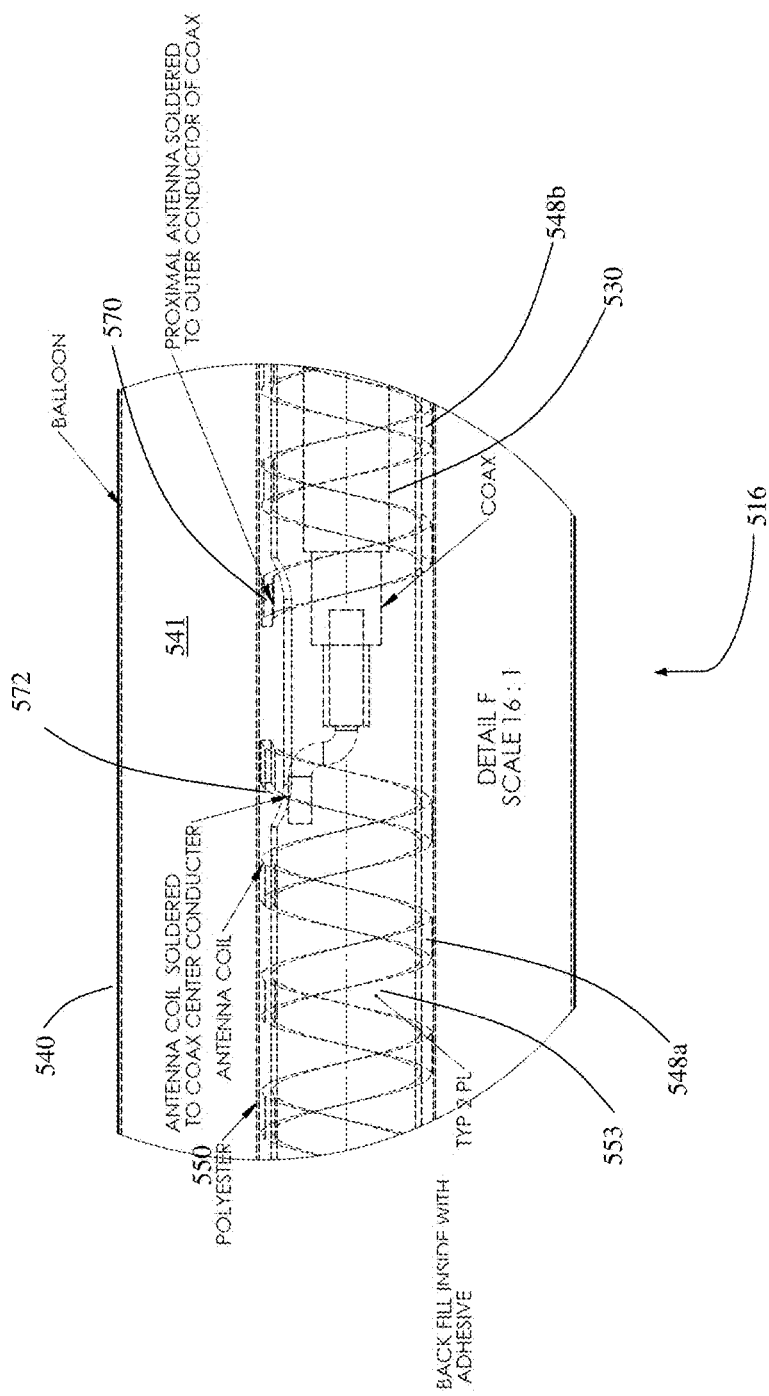
Figure 41D:
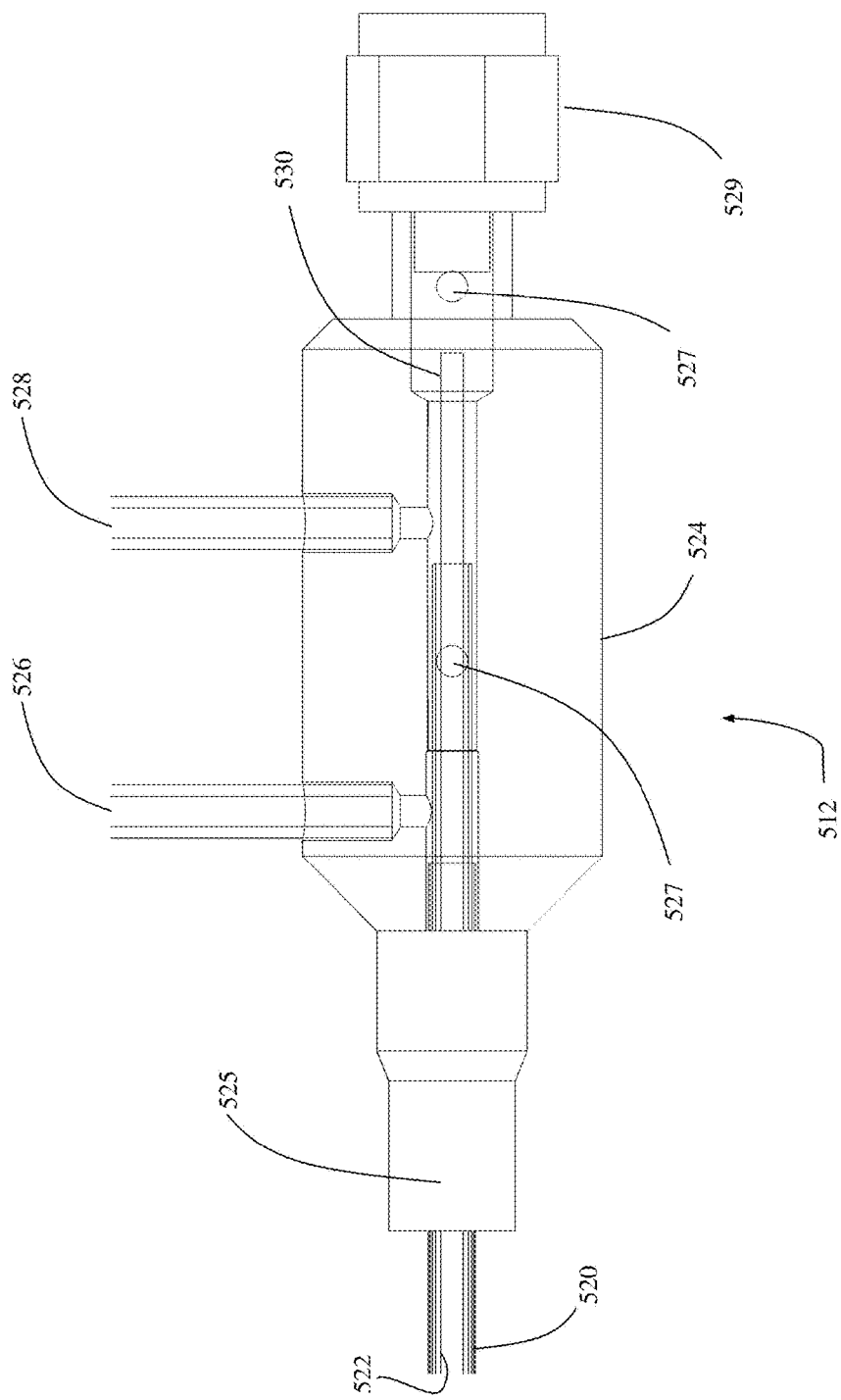

FIG. 41C is an exploded view of distal portion 516 of an exemplary embodiment of microwave antenna carrying catheter 510 including construction details. In the exemplary embodiment shown, balloon 540 is made of Nylon, shrink material 550 is made of polyester, and potting adhesive 553 is Loctite 331. In other embodiments, balloon 540 may be made of other materials, including materials having compliant or blended properties. Solder is used to make connections 570 and 572 that connect the proximal and distal antenna coils 548b and 548a, respectively (although other means of attachment such as welding may be used in other embodiments). Balloon 540 has interior chamber 541 as described above.

FIG. 41D depicts a detailed drawing of proximal portion 512 of microwave antenna carrying catheter 510. Catheter inner wall 522 is advanced into manifold body 524 and bonded using adhesive fill port 527. Catheter outer wall 520 is advanced inside distal end of manifold body 524 and bonded. Flexible strain relief 525 is placed over catheter tubing where it enters the distal end of manifold body 524, and supports the tubing during bending so it does not kink. Coolant enters manifold body 524 through passage 526 and into the space between inner catheter wall 522 and outer catheter wall 520. Coolant returns from the space between inner catheter wall 522 and coaxial cable 530 and out through passage 528 as described previously. Alternately, the coolant flow may be reversed. Coaxial cable 530 is terminated to connector 529 and potting adhesive delivered through port 527 seals and affixes connector 529 to manifold body 524.

Figure 42:
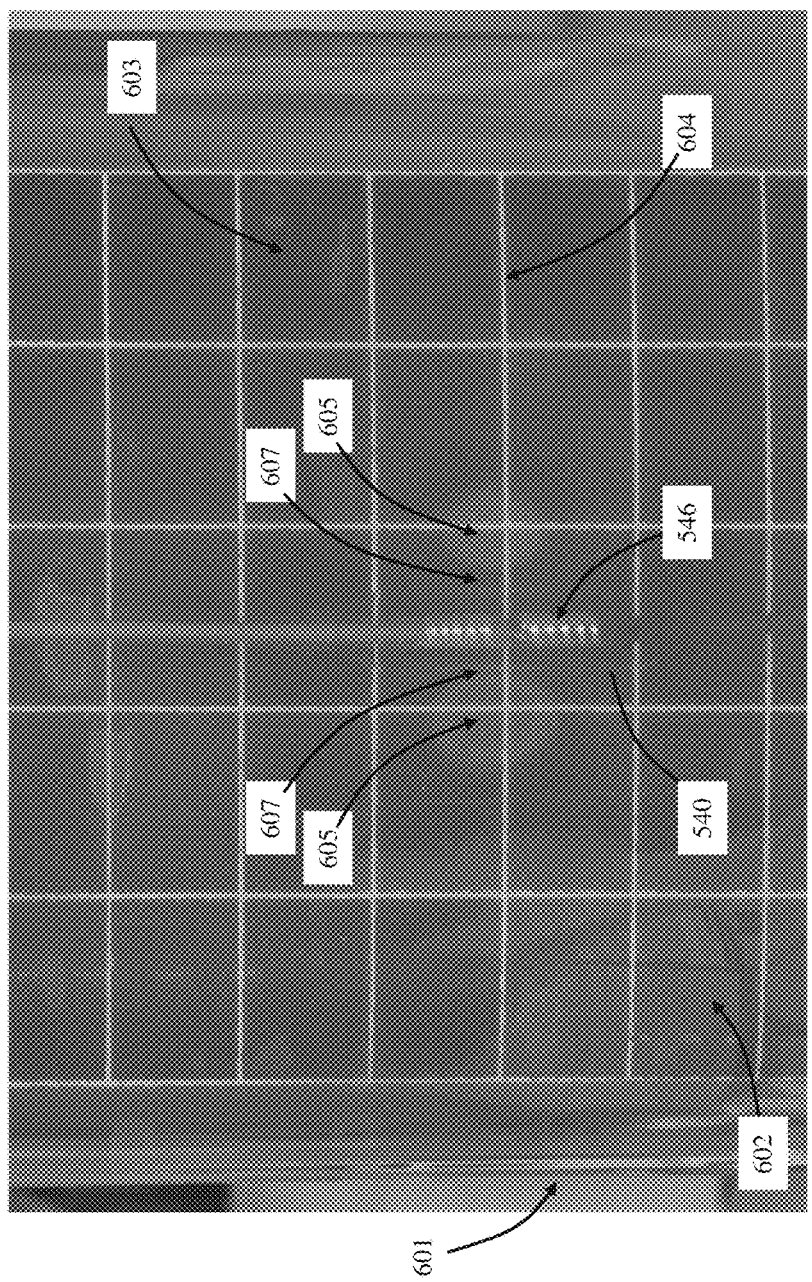
FIG. 42 is a photograph of a tissue equivalent phantom containing sheets of Liquid Crystal Temperature sensing film that enables visualization of the temperature field produced by the present embodiment.

FIG. 42 is a diagram illustrating tissue equivalent phantom containing sheets of Liquid Crystal Temperature sensing film 603 that enables visualization of the temperature field produced by the present invention. Specially formulated and cross linked gel 602 fills container 601 and mimics dielectric and thermal properties of tissue. Sheets of Liquid Crystal Temperature sensing film, 603 are placed within gel 602. Graticule lines 604 are spaced 10 mm apart and are screened directly to Liquid Crystal Temperature sensing film 603 (graticule lines 604 may appear non-square in FIG. 42 due to geometric distortion from the phantom container 601 and/or the camera lens). Catheter 510, carrying microwave antenna 546, is advanced into gel 602 adjacent the liquid crystal sensing film 603. Catheter 510 is energized with microwave power and provided with circulating cooling fluid in accordance with the techniques described herein, and the resulting temperature field can be viewed on the Liquid Crystal Temperature sensing film, 603, as rings of color corresponding to isotherms. FIG. 42 clearly depicts two tightly controlled regions 605 of temperature elevation spaced from balloon 540 by a cooler region 607 that prevents ablation of the renal artery. Additionally, it may be observed that the size of the heated zones 605 is ideal for targeting renal nerves and sparing the artery.

Figure 43:
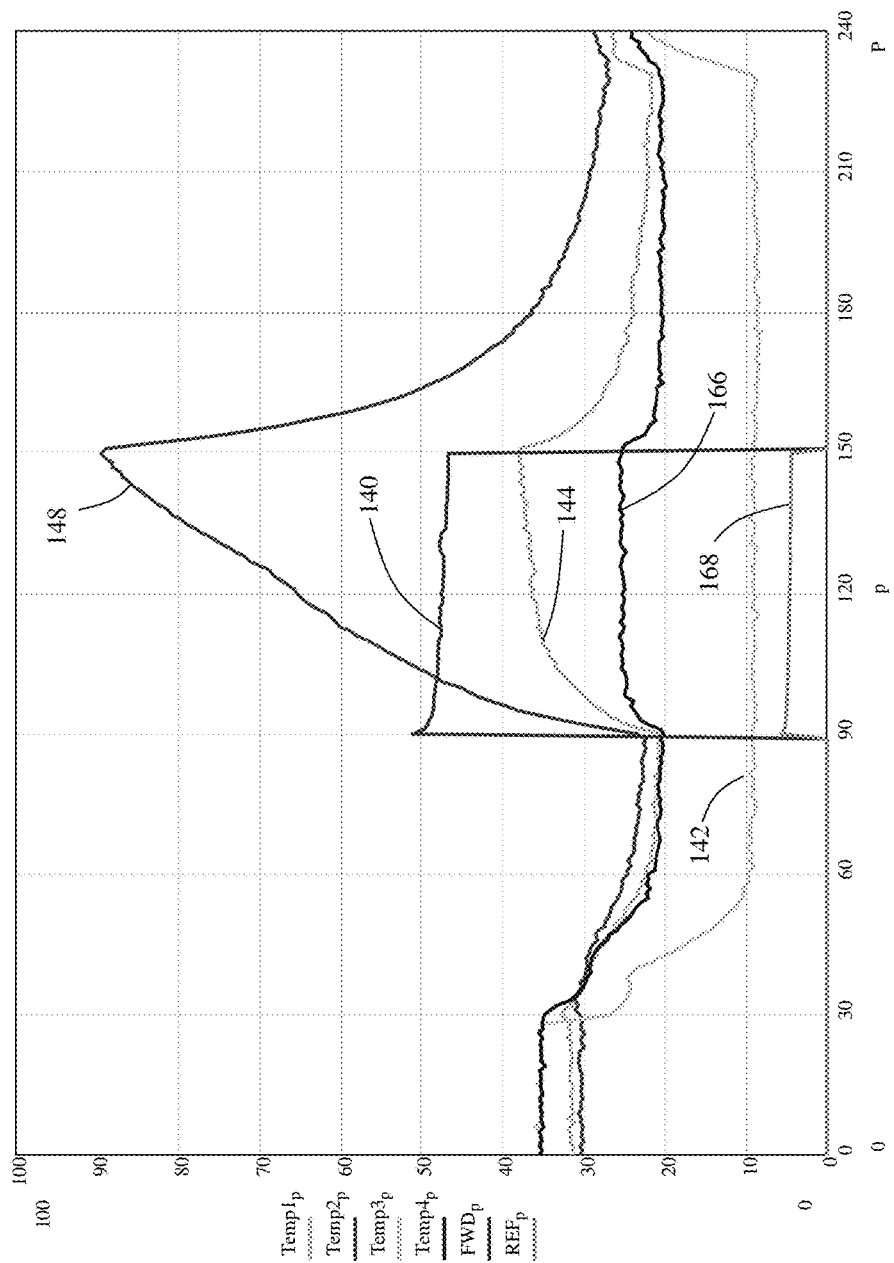
FIG. 43 is a graph of the microwave power, microwave reflected power, coolant temperature, and tissue temperatures in the region of a porcine renal artery during microwave renal denervation in accordance with the present embodiment that produced the histology sections shown in FIGS. 44A-44D.

FIG. 43 is a graph of the microwave power, microwave reflected power, coolant temperature, and tissue temperatures captured by temperature sensors placed in the region of a porcine renal artery during microwave renal denervation using the microwave antenna carrying catheter of the present embodiment. This temperature field produced the histology sections shown in FIGS. 44A-44D. The x-axis is time in seconds. The y axis is temperature in degrees C. for the temperature data (curves 142, 144, 166 and 148) and power in Watts for the forward & reflected power (curves 140 and 168, respectively). Tissue temperature data in the target zone, approximately 2 mm from the intima, is labeled 148 and reaches a temperature above 80° C. Tissue temperature data from a sensor located adjacent the intima (between balloon 540 and the artery wall) is labeled 144 and remains below 40° C. Coolant input temperature is labeled 142 and is substantially below body temperature. Coolant outlet temperature is labeled 166 and is also substantially below body temperature. Forward power in Watts is labeled as 140. Reflected power in Watts is labeled as 168.

FIGS. 44A-44D are histology slides that demonstrate thermal destruction of renal nerves without any damage to the intima or media of a representative porcine renal artery using the present embodiment in accordance with the present invention.

Figure 44A:
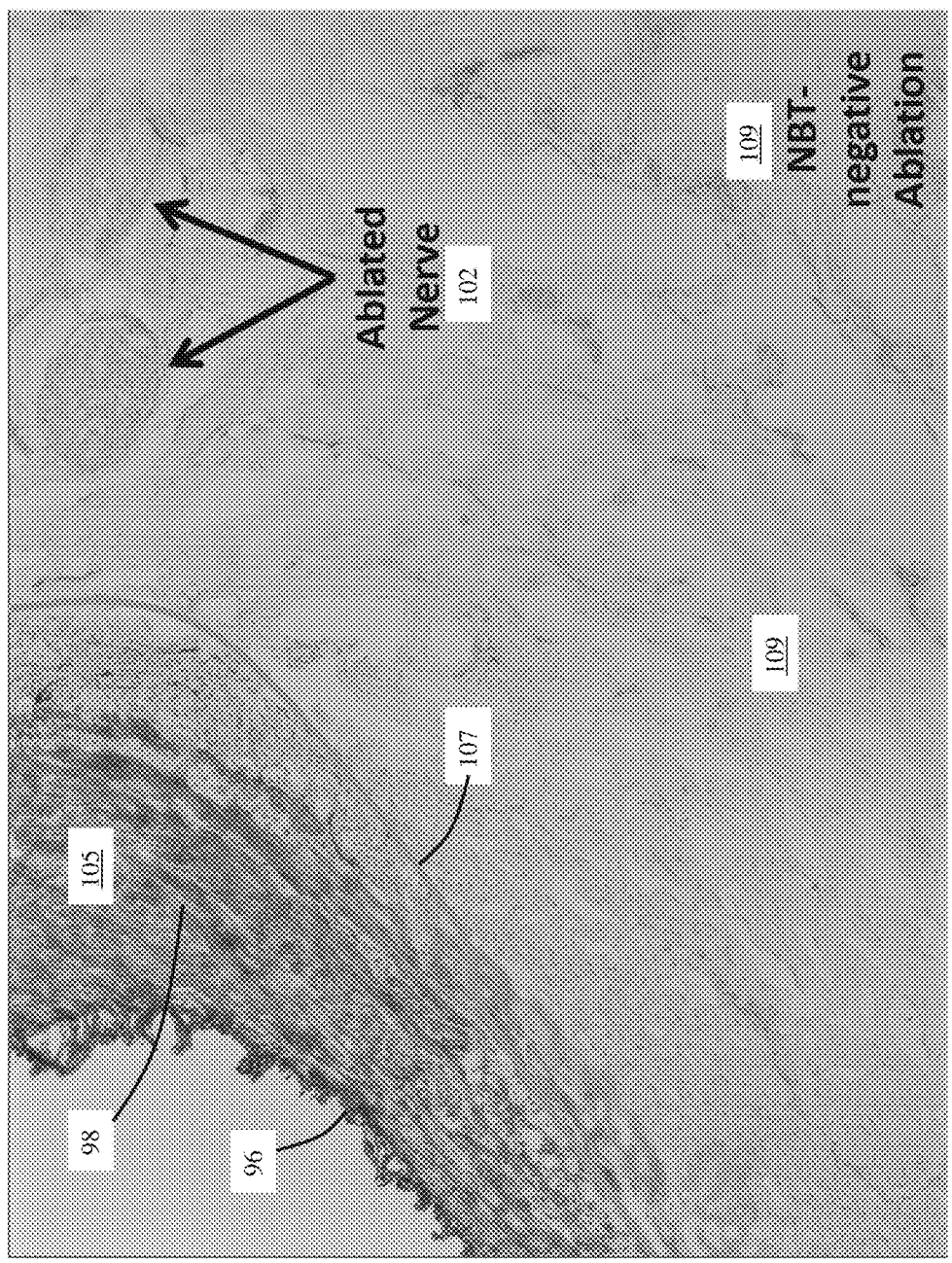
FIGS. 44A-44D are histology slides that demonstrate thermal destruction of renal nerves without any damage to the intima and media of a representative porcine renal artery using the present embodiment in accordance with the present invention.

FIG. 44A depicts the intima 96 and media 98 of a porcine renal artery in the upper left region of the picture as treated by the present invention. Both intima 96 and media 98 are viable as evidenced by nitro blue tetrazolium (NBT) positive staining throughout region 105. Line 107 has been drawn by pathology to illustrate the boundary between NBT Positive (viable) tissue in region 105 and NBT Negative (ablated) tissue in region 109. All tissue within region 109 is ablated, including ablated nerves 102.

Figure 44B:
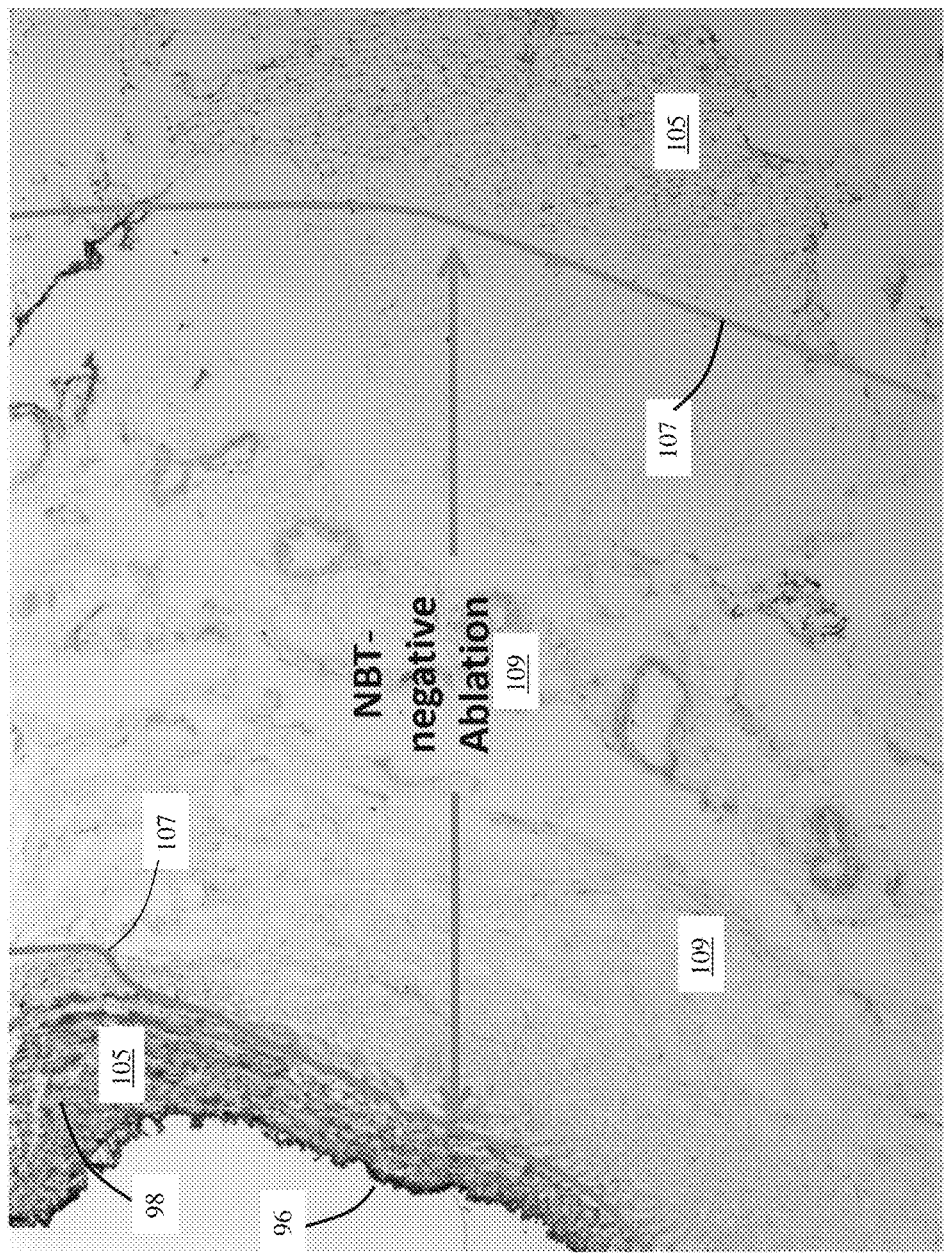

FIG. 44B depicts another region of tissue surrounding intima 96 and media 98 of a porcine renal artery as treated by the present invention. NBT Positive region 105 contains intima 96 and media 98, as can be observed on the left side of the slide. Boundary 107 has been drawn as before to separate the NBT positive (viable) tissue in both regions marked 105 from NBT negative (ablated) tissue in region 109. All tissue within region 109 is ablated.

Figure 44C:
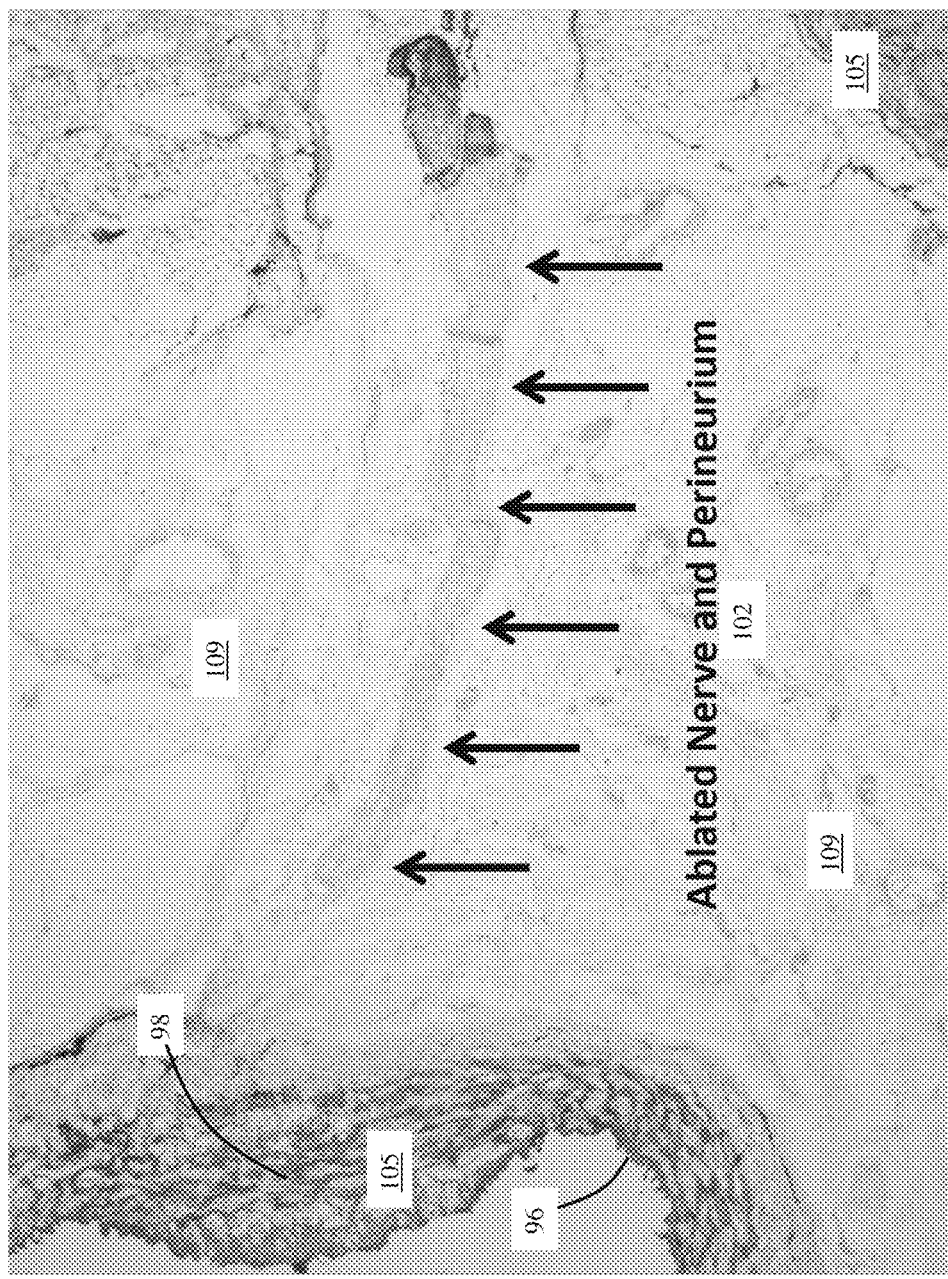

FIG. 44C depicts another region of tissue surrounding viable intima 96 and media 98 within NBT positive (viable) region 105. Adjacent to region 105 is NBT negative (ablated) region 109. Within region 109 is an example of an ablated nerve 102 and perineurium. More distant from the artery is NBT positive tissue that is again viable.

Figure 44D:
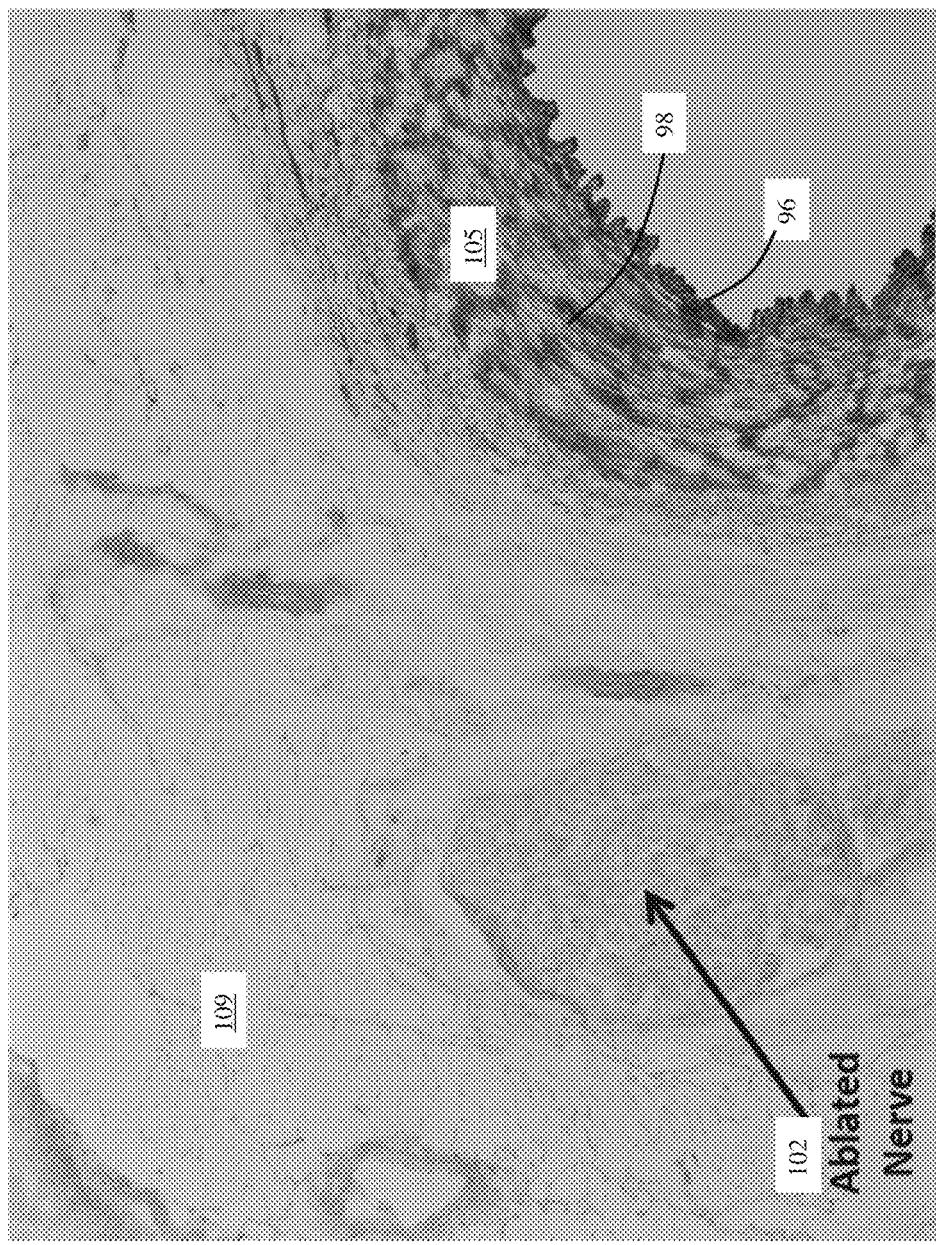

FIG. 44D depicts another region of tissue surrounding viable intima 96 and media 98 of a renal artery within NBT positive (viable) region 105. Adjacent to region 105 is NBT negative (ablated) region 109. Within NBT negative (ablated) region 109 is a renal nerve 102 that is also ablated.

Figure 44E:
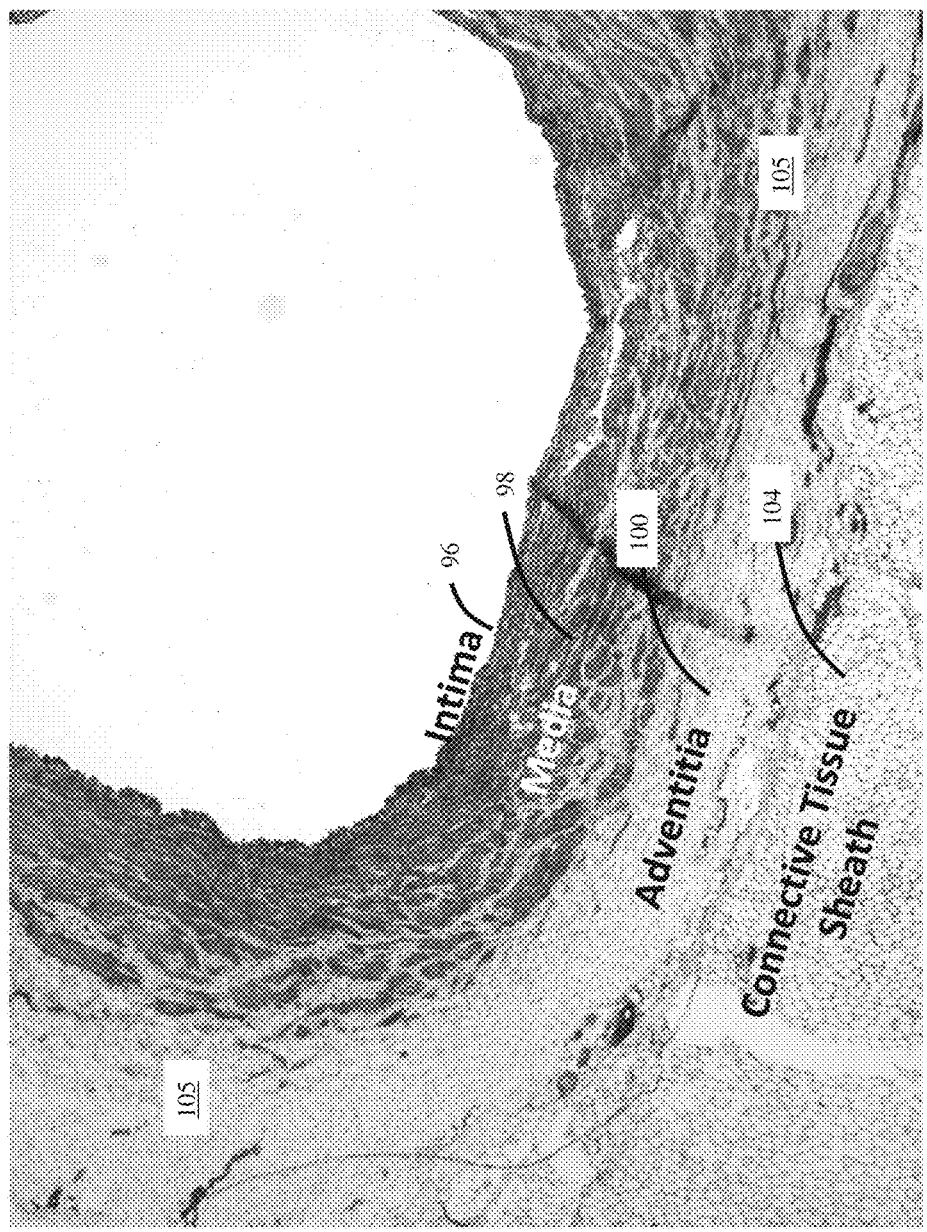
FIG. 44E is a histology slide depicting viable tissue throughout as evidenced by NBT positive staining.

FIG. 44E is a histology slide depicting viable tissue throughout as evidenced by NBT positive staining. NBT positive (viable) tissue exists throughout and the intima 96, media 98, adventitia 100, and surrounding connective tissue 104 are clearly visible as normal tissue. This slide is useful to compare to the ablated regions.

Figure 45A:
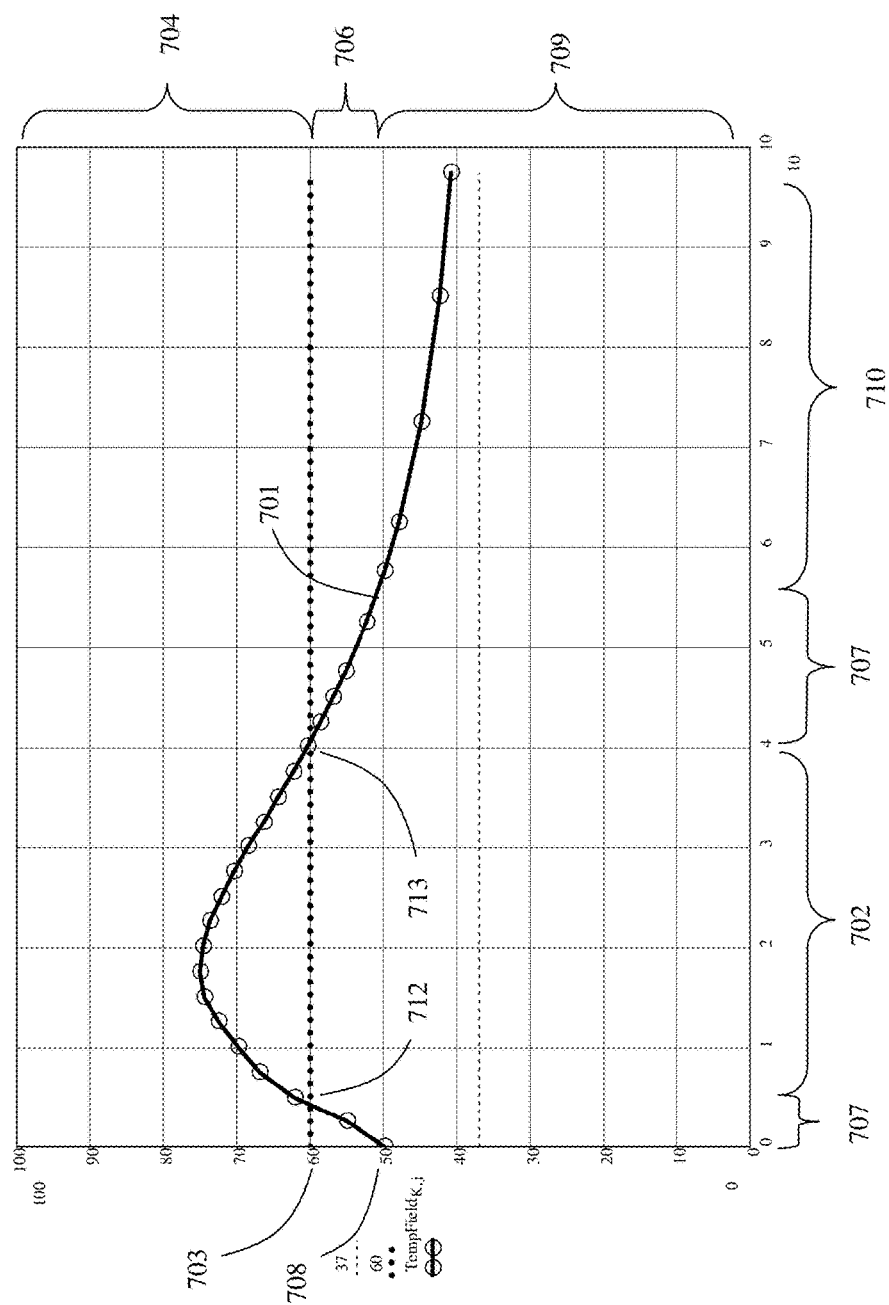
FIGS. 45A-45C are computer simulation graphs that illustrate the importance of cooling to protect intima and media tissues.
Figure 45B:
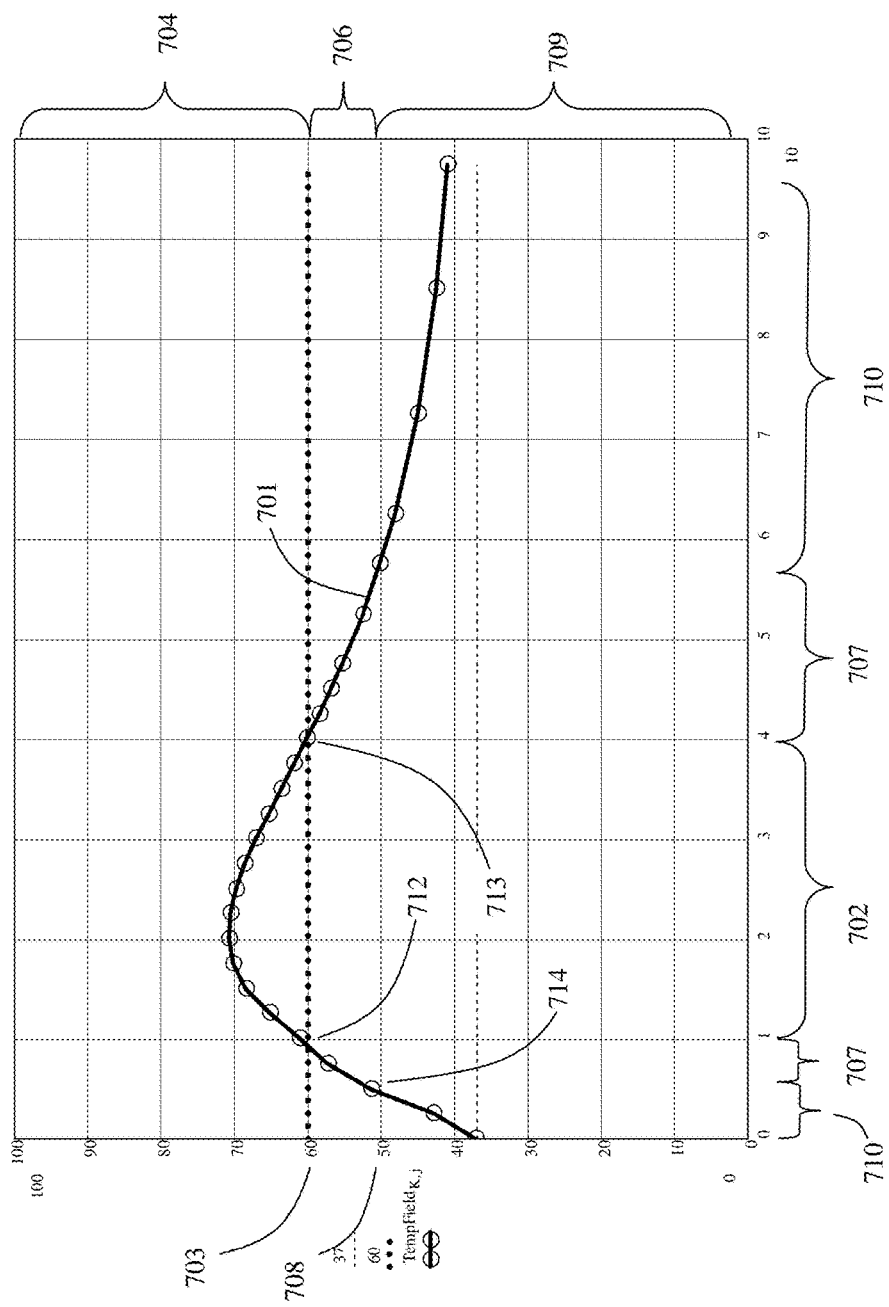
Figure 45C:
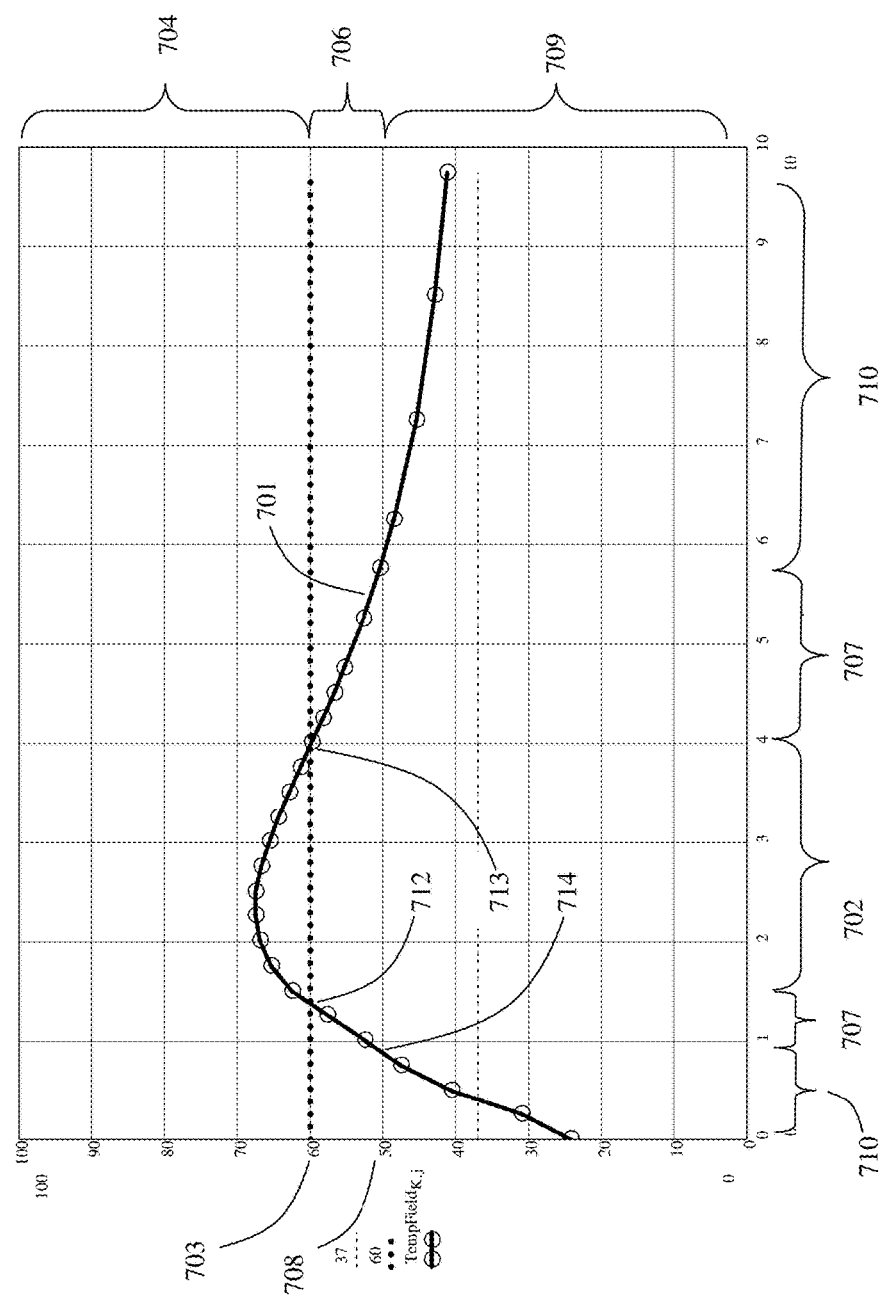

FIGS. 45A-45C are computer simulation graphs that illustrate the importance of cooling in accordance with embodiments of the present invention to protect intima and media tissues from thermal injury. For all these graphs, the x-axis is distance in mm with zero (the origin) being the inner surface of the intima (lumen). The y-axis is temperature in degrees C. The computed temperature for each discrete computational node (distance from intima) is identified by a circle, and lines 701 are drawn between nodes to interpolate the solution for any value of distance. A 6 mm diameter balloon has been simulated as this is an average renal artery diameter for humans.

Although the exact thermal ablation threshold temperature for a 60 second renal nerve ablation is not presently known and is the subject of future research, and temperature varies with time, for illustrative purposes a simplified threshold of 60 degrees C. will be used for ablation based upon anecdotal evidence. Similarly, the tolerance for the intima, media and adventitia of a renal artery for a 60 second exposure to temperature elevation is also not known. However, based upon anecdotal evidence it is expected to be around 50 degrees C. For the purpose of illustrating the present invention, the threshold value 708 for protection is established at 50 degrees C., and the threshold value 703 for ablation is established at 60 degrees C.

Given these thresholds, it is therefore desirable to achieve tissue temperature greater than 60° C. (above threshold 703) in the region 702 (distance from intima) of the renal nerves, while keeping the intima and media of the renal artery below 50° C. (below threshold 708). Accordingly, on all graphs the temperature range sufficient for ablation is marked 704, temperature for tissue preservation is marked 709, and temperature for which some level of thermal injury can be expected is marked 706. The ablation radial distance is marked 702. The range of distance for which safe temperature exposure is maintained is marked 710.

FIG. 45A depicts simulated temperature 701 achieved at the end of a 60 second ablation procedure with a coolant temperature of 36° C. and power set to 60 Watts. Note that the simulated temperature curve 701 crosses the 60° C. line 703 at about 0.5 mm (marked 712), and again at 4.0 mm (marked 713), corresponding to the inner and outer radius of the ablation zone. Notice also that the intima temperature is at 50° C., and rises very rapidly as distance is increased to 0.5 mm. Accordingly, the intima and media are exposed to a range of temperature (marked 706) in excess of 50C, (threshold 708) over a distance 707, and will likely be thermally injured. This temperature field would be expected to produce an ablation outer radius of 4 mm (marked 702) from the intima, but will undesirably heat the intima and media.

FIG. 45B depicts simulated temperature 701 achieved at the end of a 60 second ablation procedure with a coolant temperature of 21° C. and power set to 64 Watts. In this simulation, the temperature curve 701 crosses the 60° C. line at about 1.0 mm, (marked 712), and again at 4.0 mm (marked 713). The intima temperature is below 40° C. and the 50° C. threshold is crossed at about 0.5 mm (marked 714). Accordingly, this temperature field would be expected to produce an outer ablation radius 702 of 4 mm from the intima as before, but with about 0.5 mm of viable tissue surrounding the intima (marked 710).

FIG. 45C depicts simulated temperature achieved at the end of a 60 second ablation procedure with a coolant temperature of 6° C. and power set to 68 Watts. In this simulation, the temperature curve 701 crosses the 60° C. line (703) at about 1.4 mm (marked 712), and again at 4.0 mm (marked 713), as in the simulation of FIG. 45B described above. The intima temperature is maintained at approximately 25° C. and the 50° C. threshold (708) is not crossed until almost 1.0 mm (marked 714). Accordingly, this temperature field would be expected to produce an outer ablation radius 702 of 4 mm from the intima as in the previous simulation, but with at least about 1 mm of viable tissue (marked 710) surrounding the intima. This will effectively protect intima 96, media 98, and adventitia 100.

The preceding discussion assumed simplified threshold values for thermal injury to renal tissue for illustrative purposes. It is within the scope of the present invention to adjust treatment parameters to achieve specific thermal dosimetry as the specific thermal thresholds are determined, and to include the effects of time varying temperature in order to achieve the desired ablation outer radius and simultaneous protection of selected portions of artery tissue. Further, FIGS. 45A-45C clearly indicate the importance of cooling using coolant that is below body temperature to protect the artery and enable a short duration, high temperature ablation.

Pulmonary Denervation

According to another example of a concept associated with the present invention, a device and method are provided to create a thermal lesion in the immediate adjacent surrounding tissue of a bronchus containing nerve trunks which traverse along the outside of both the right and left primary bronchi, so that these nerve trunks are thermally damaged, while protecting the bronchus from injury. This disconnects airway smooth muscle and mucus producing glands from the vagus nerve and central nervous system, resulting in a relaxation of the airway smooth muscle and a reduction in mucus production. Accordingly, airway obstruction due to disease such as COPD and asthma is reduced. The present invention has the advantage of protecting the intervening bronchial tissue and not requiring the energy emitter to be electrically in contact with the tissue. An additional advantage is the potential for a shortened procedure time and easier procedure.

Figure 46A:
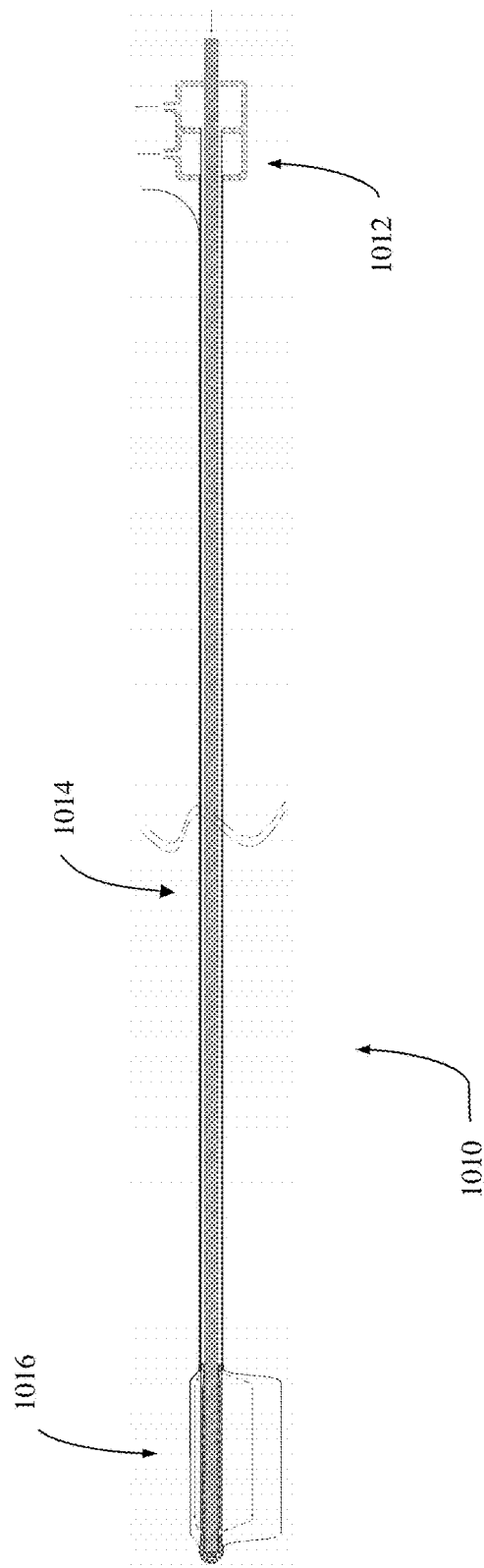
Figure 46B:
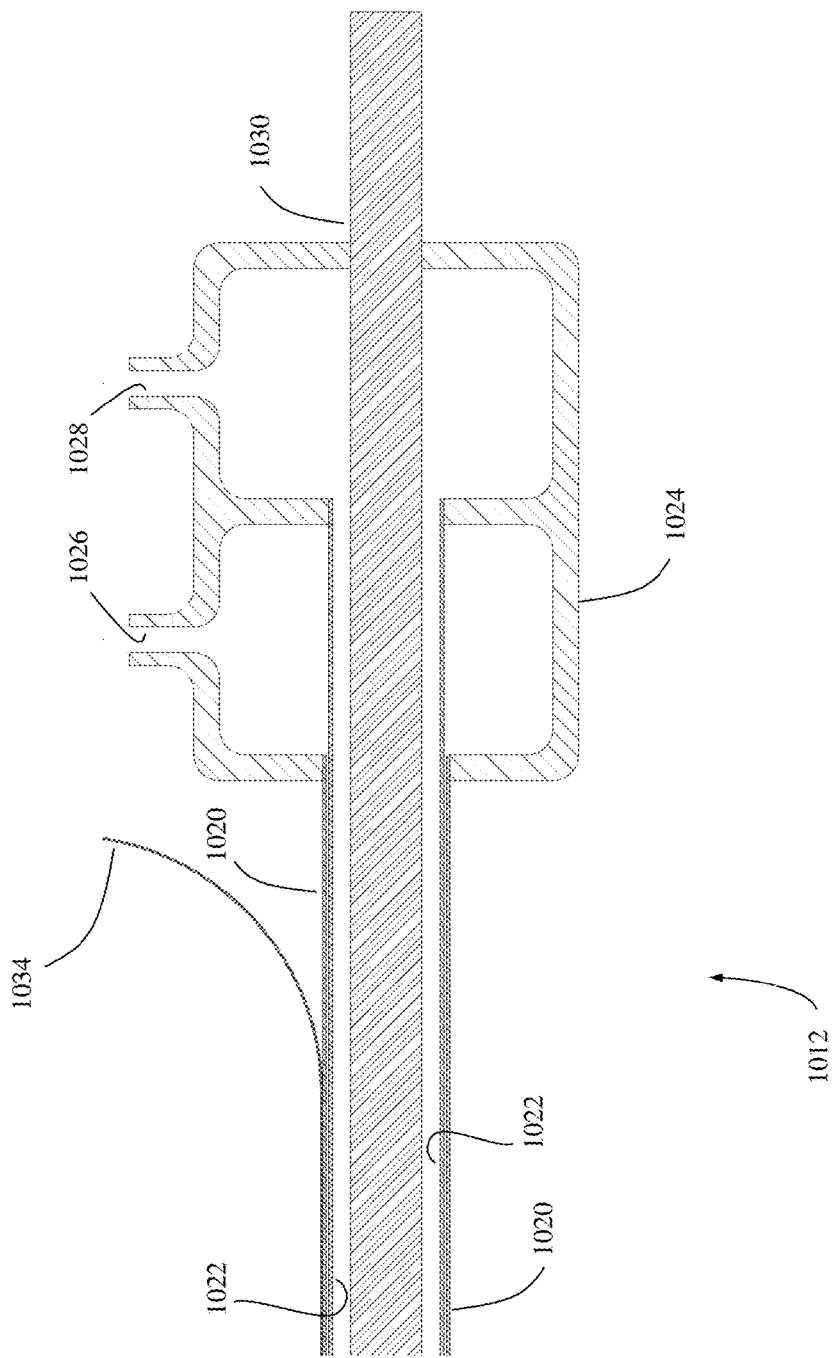

FIGS. 46A-46E are diagrams illustrating microwave antenna-carrying catheter 1010 according to an embodiment of the present invention. As shown in FIG. 46A, catheter 1010 includes proximal portion 1012, middle portion 1014, and distal portion 1016. FIG. 46B is an enlarged view of proximal portion 1012 of catheter 1010. Catheter 1010 includes outer body wall 1020 and inner body wall 1022, between which a space is defined for the flow of coolant. At proximal portion 1012 of catheter 1010, coolant intake/exhaust structure 1024 is provided, with walls configured to provide a coolant input port 1026 that communicates with the space between outer body wall 1020 and inner body wall 1022 of catheter 1010, and also to provide a coolant output port 1028 that communicates with an interior of catheter 1010 formed by coaxial cable 1030 and the inside inner body wall 1022. Coaxial cable 1030 is provided to the interior of catheter 1010 inside inner body wall 1022, is coupled to a microwave antenna 1046 (FIG. 46D) at distal portion 1016 (FIG. 46A) of catheter 1010, and is coupled to a microwave generator (not shown) to supply power to the microwave antenna via coaxial cable 1030. A balloon on the distal portion inflates asymmetrically to achieve targeting of the bronchus nerve trunk.

Figure 46C:
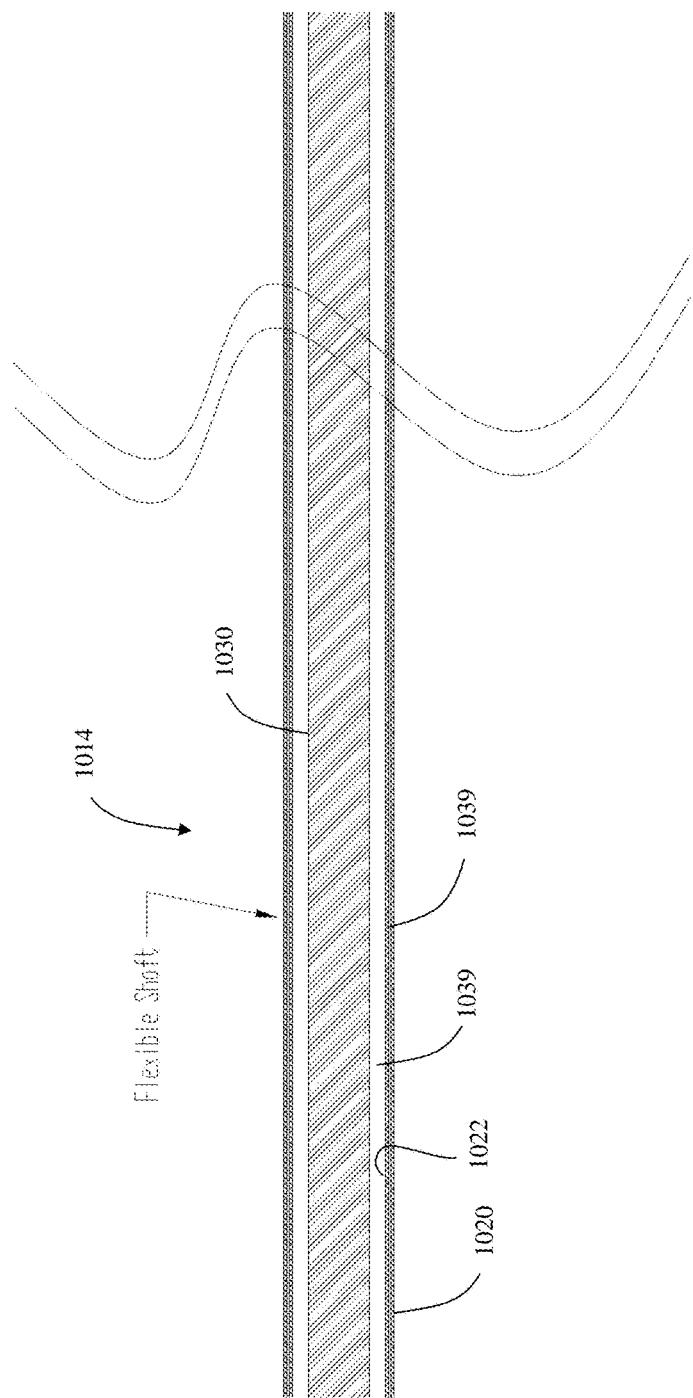

FIG. 46C is an enlarged view of middle portion 1014 of catheter 1010, showing outer body wall 1020, inner body wall 1022, coaxial cable 1030, and interior region for coolant to flow within catheter body walls 1039. These components make up the flexible shaft of catheter 1010 that is able to be guided into the bronchus of a patient via the trachea, for example. The length is suitable to conveniently be inserted into the mouth and reach the bronchus via the trachea or may be adjusted to accommodate other insertion locations. The catheter shaft 1014 includes a torquable attribute to enable alignment of the balloon with the target nerve trunk. This attribute may be an external braid, torquable coaxial cable, or a combination of these to ensure proper alignment to the target nerve trunk.

Figure 46D:
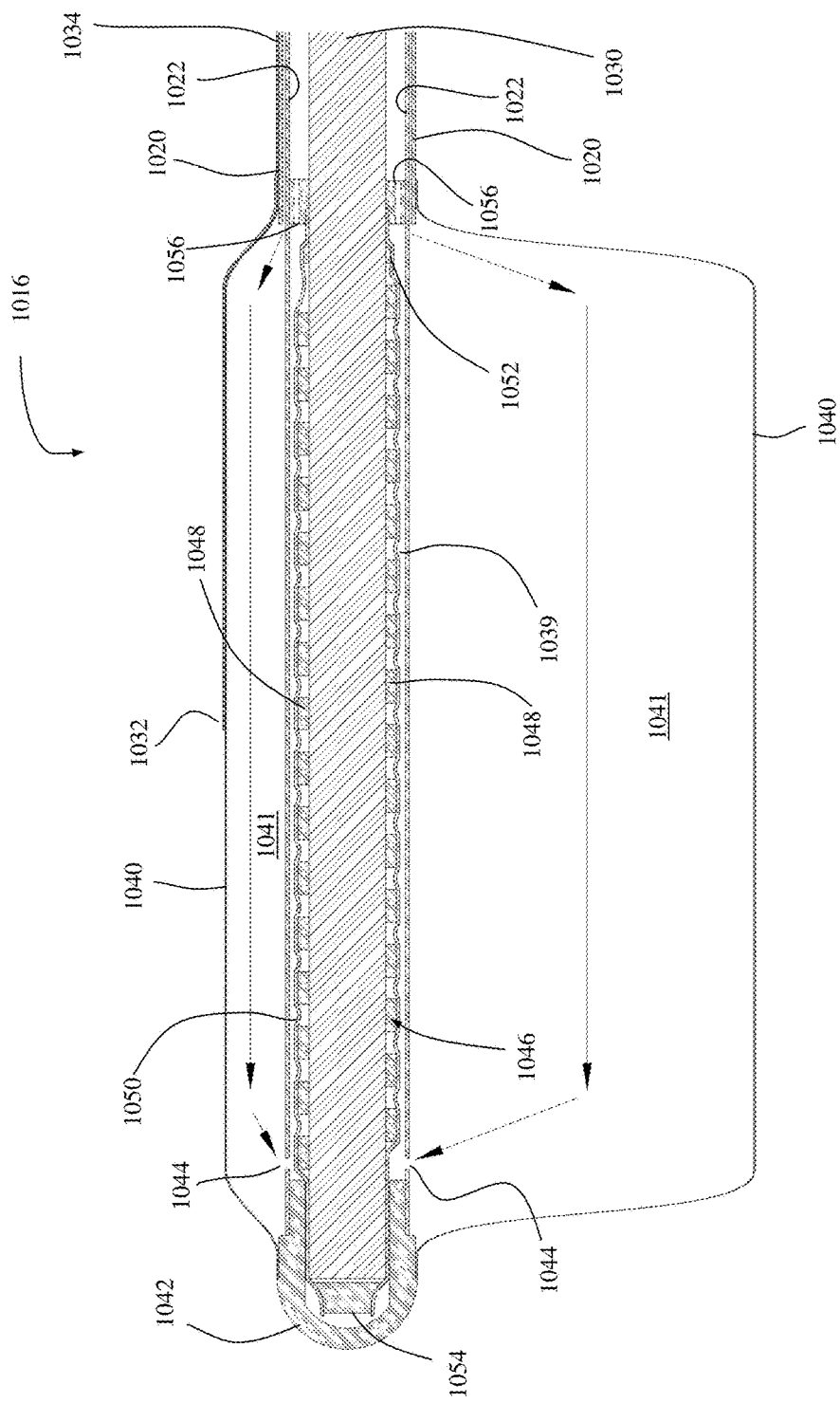

FIG. 46D is an enlarged view of distal portion 1016 of catheter 1010. As shown in FIG. 46D, balloon 1040 is attached to outer body wall 1020 of catheter 1010 to form interior region 1041 for cooling fluid to inflate balloon 1040 asymmetrically to achieve directionality to target the nerve trunk. Cooling fluid pressure is responsible for inflation of the balloon and may be controlled by an external pressure regulator (not shown) incorporated into the tubing or control unit connected to catheter 1010. Balloon 1040 is attached to tip 1042 at a distal end of distal portion 1016 of catheter 1010. Return ports 1044 are provided in inner body wall 1022 of catheter 1010 to allow cooling fluid to exit balloon 1040 and flow in a return path toward proximal portion 1012 (FIG. 46B) of catheter 1010, in the space between inner body wall 1022 and microwave antenna 1046. Additional ports are provided in coaxial cable spacer 1056 so that coolant may continue to flow in a return path toward the proximal portion 1012 (FIG. 46B) of catheter 1010 in the space formed between the inner body wall 1022 and coaxial cable 1030. Microwave antenna 1046 is coupled to coaxial cable 1030 at distal portion 1016 of catheter 1010, with windings 1048 configured to form a microwave radiator. Thin wall shrink tubing 1050 is placed around antenna 1046 to isolate it from coolant flowing within space 1039. Additional details on various antenna embodiments are depicted in FIGS. 28, 29, 32, 34 and 36 described above with respect to the renal denervation catheter example, as the same or similar considerations are involved in the configuration of the microwave antenna for renal denervation and pulmonary denervation (as well as for other denervation procedures). A temperature sensor 1032 is positioned on the surface of balloon 1040 to monitor the temperature of the intima 1096 during the treatment. The temperature reading may be used to control treatment parameters and/or to ensure safety.

FIG. 46E and FIG. 47 depict an embodiment of catheter 1010 without a temperature sensor 1032. For some treatment algorithms this sensor is not necessary and it simplifies 1010 and also eliminates the possibility of non-uniform heat transfer between mucosa at the intima 1096 of bronchus 1094 and coolant within balloon 1041.

Figure 46F:
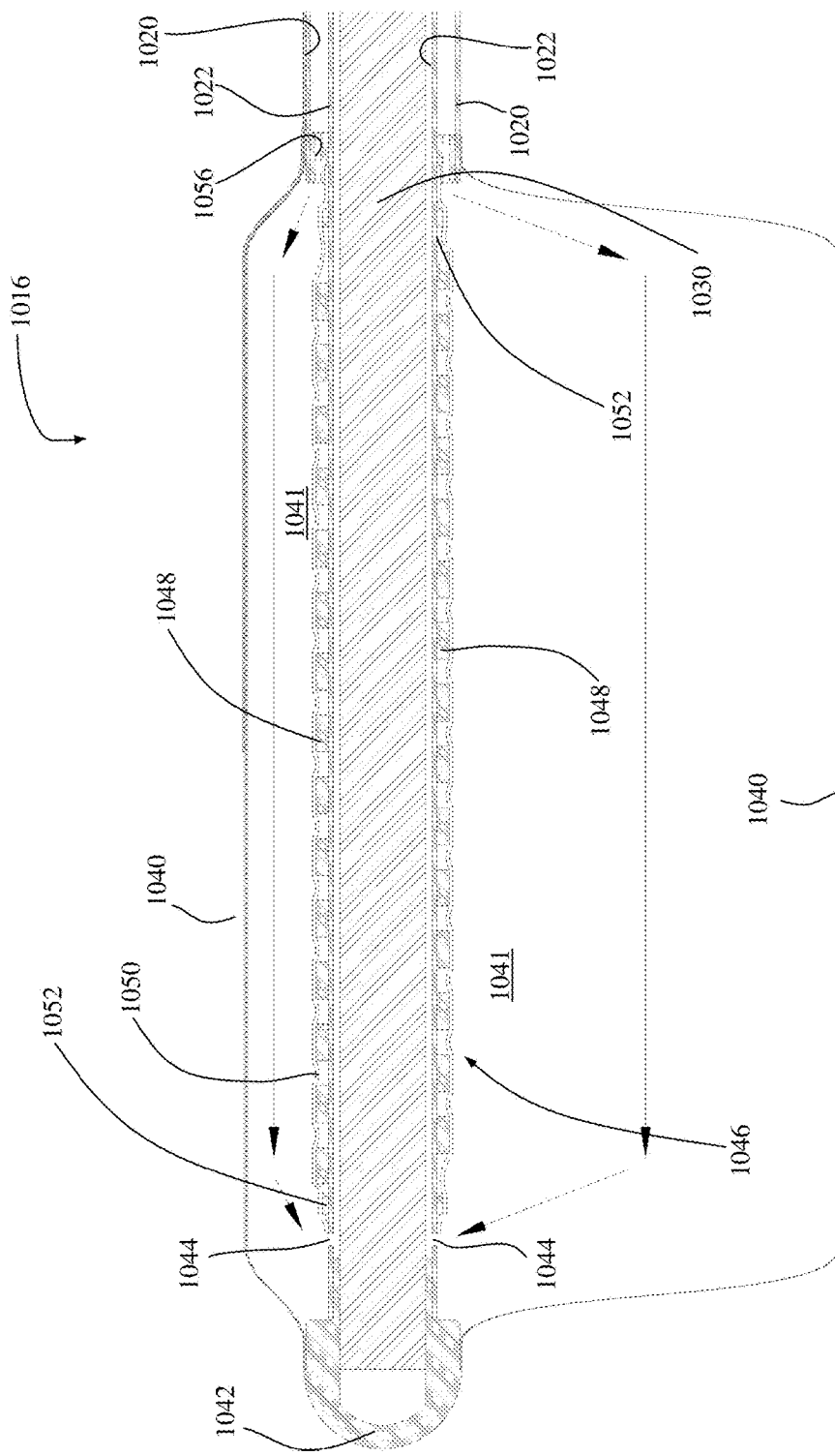

FIG. 46F depicts an embodiment of catheter 1010 that locates antenna coil 1048 within balloon 1040 rather than within the catheter body wall. Coolant flows between inner body wall 1022 and outer body wall 1020, through spacer 1056, and into interior region 1041 formed by balloon 1040 as before. However, antenna coil 1048 is placed within this region as well, separated only by shrink tubing 1050 from coolant within 1041. Coolant then flows through ports 1044 as before but in this embodiment coolant will flow between coaxial cable jacket 1030 and inner body wall 1022 within the antenna. Specific antenna adaptations to permit this flow of coolant and seal coolant from interior regions of coaxial cable 30 are diagramed in FIG. 36 as described above with respect to the renal denervation example.

FIG. 47 is a diagram of more details of distal portion 1016 of catheter 1010 including cross sectional views of the balloon 1040, of the coaxial cable spacer 1056, and of the shaft of catheter 1010. Cross section 1074 corresponds to section A-A and includes balloon 1040, the region 1041 for coolant to flow inside the balloon 1040, coaxial cable 1030, antenna coil 1048, antenna shrink tubing 1050, and a region 1039 within which coolant flows between the antenna and inner body wall 1022. The outer body wall 1020 does not extend into the balloon beyond spacer 1056. Cross section 1076 corresponds to section B-B and includes coaxial cable spacer 1056 containing ports 1044 for coolant to flow in the return path, inner body wall 1022, outer body wall 1020, an inner region 1039 for coolant to flow, and balloon 1040 as bonded to outer body wall 1020. Cross section 1078 corresponds to section C-C and includes coaxial cable 1030, inner body wall 1022, outer body wall 1020, and regions 1039 for coolant to flow within the catheter body walls 1020 and 1022.

Computer Simulation of Operation of Microwave Catheter for Pulmonary Denervation A computer simulation of operation of a microwave catheter for pulmonary denervation was performed to illustrate the temperature profile that could be expected to be achieved. The simulation was configured with the following parameters and assumptions:

Published and estimated thermal physical properties were used for smooth muscle, fat, blood and nerves Published and estimated complex dielectric properties (conductivity, permittivity) were used for smooth muscle, fat and other anatomical structure.

Microwave emitter geometry, specific absorption rate (SAR) field and heat transfer coefficient were modeled The simulation space begins at the catheter/mucosa wall interface, and is modeled as a two 1-dimensional models and extended to 2 dimensions by rotational interpolation between the preferentially hot side and the cool side.

The thermal simulation was performed based upon the Penne's Bioheat equation first published in 1948.

$$\rho_t c_t \frac{\partial T}{\partial t} = div(k \; gradT) - \omega \rho_b c_b (T - T_a) + Q + Q_m$$

This equation is an energy balance that simply states the sum of conductive heat flow minus convective heat due to blood flow plus heat generation from an external source (microwave) plus metabolic heating gives rise to temperature elevation. In practice, the metabolic component $Q_m \ll Q$ and can be neglected.

An iterative solution to this equation was implemented and run in the computer simulation. A microwave term was incorporated based upon measured SAR data for the antenna described in U.S. Pat. No. 5,300,099 but modified to account for the different dielectric constants of smooth muscle, fat, and cartilage.

Figure 48A:
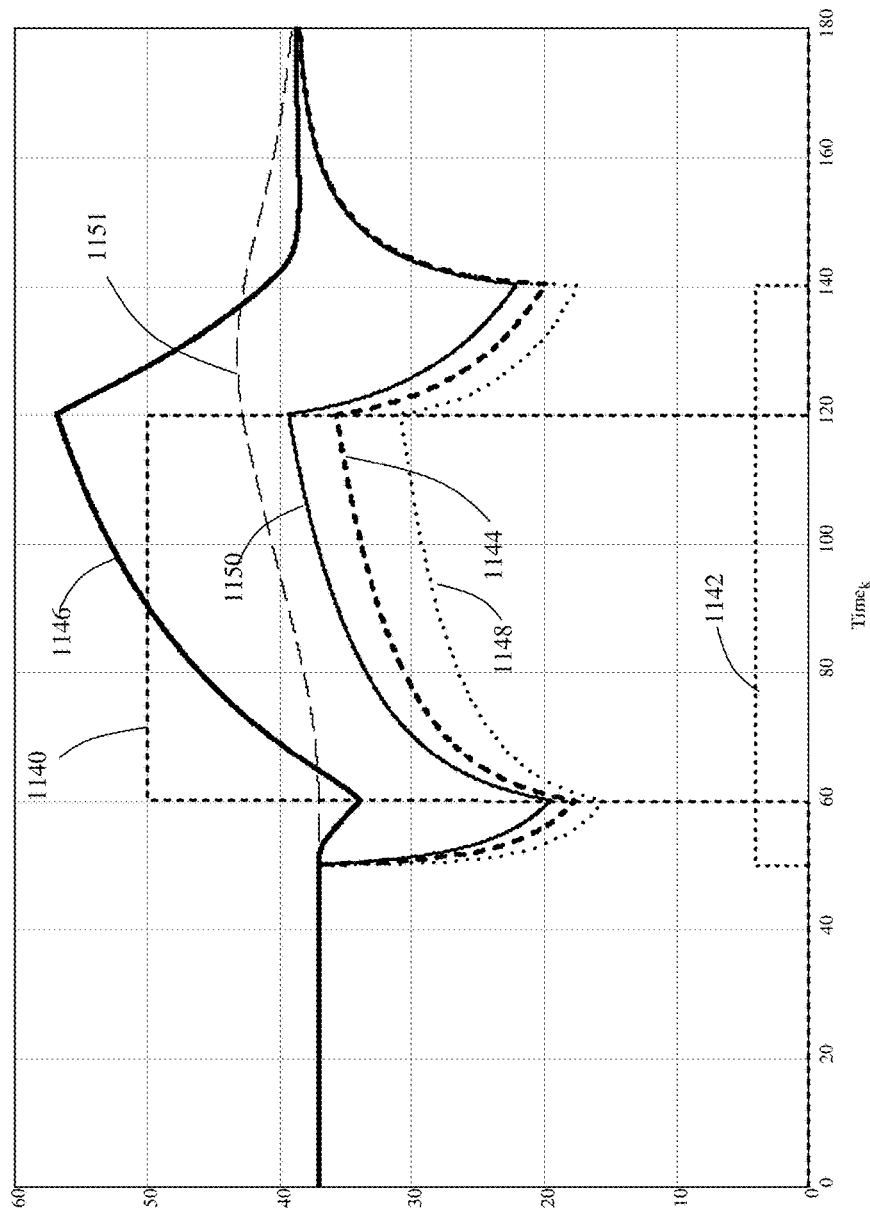
FIG. 48A-48D are graphs that illustrate a temperature profile achieved by a computer simulation of the operation of a microwave catheter for pulmonary denervation as a function of time (48A) and position (48B, 48C and 48D).

FIG. 48A is a graph of a representative simulation as described above as a function of time. In this simulation, coolant flow at a temperature of 4° C. (1142) is initiated 10 seconds prior to initiating microwave power (1140) at a constant 50 Watts for 60 seconds. Following the discontinuation of microwave power (1140), coolant flow 1142 is maintained at 6° C. for 20 seconds. Simulated temperatures corresponding to mucosa on the preferentially hot side 1144 and cool side 1148, target tissue temperature on the preferentially hot side 1146 and cool side 1150, and nearby fat tissue 1151 are shown. Thermal injury depends on the entire thermal history (time & temperature) and depends upon the specific tissue. However, it can be appreciated that this simulation depicts a greater than 20° C. temperature difference between the target tissue 1146 (nerves within the layer of tissue surrounding the cartilage) and the mucosa 1144.

Figure 48B:
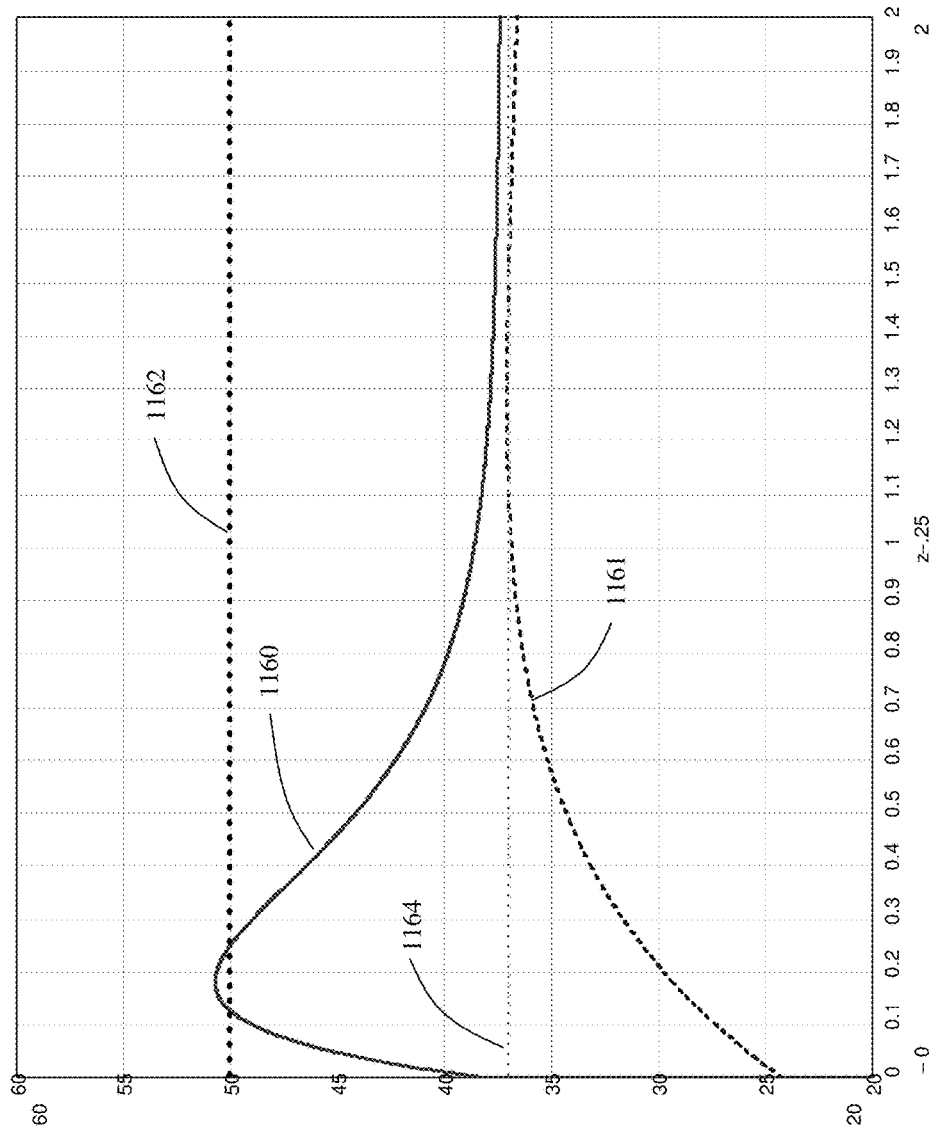

FIG. 48B is a graph illustrating the temperature profile achieved by the computer simulation described above and plotted as a function of time in FIG. 48A at a specific time so that the temperature distribution as a function of distance from the mucosa may be visualized. Tissue temperature on the preferentially hot side 1160 is plotted against position in units of mm so that it can be clearly seen that the maximum temperature (of about 53° C.) occurs at a distance of about 2.0 mm (e.g., 1.6 mm) from the intima, which is the location of the target nerves for pulmonary denervation, while the temperature within 0.5 mm of the smooth muscle layer is held below about 43° C. and temperature of the mucosa is held below 40° C. A representative thermal injury threshold for a sample treatment duration is depicted by line 1162 and basal body temperature is indicated by line 1164. For this simplified example, tissue located between about 1.5 mm and about 2.5 mm will be irreversibly thermally injured. It must be understood that thermal injury is the result of temperature AND time and a fixed threshold value of 50° C. is used here to illustrate the concept. It can be appreciated that the temperature field may be adjusted as necessary to achieve thermal injury to the specific target tissue (nerve trunk) once the specific tissue has been thermally characterized.

The targeted pulmonary nerve trunk is located where the highest temperature is achieved. The very steep temperature gradient between the mucosa and the maximum temperature region allows pulmonary nerves to be damaged sufficiently to effectively achieve pulmonary denervation therapy, while protecting the mucosa, smooth muscle, and cartilage of the bronchus from damage. Further, the decay in temperature beyond 2.5 mm is sufficient to ensure no damage to adjacent structures. The specific area in which maximum temperatures are achieved, and the temperature values achieved, can be adjusted by adjusting parameters such as power provided to the microwave antenna as a function of time, coolant temperature as a function of time, microwave duration, volume of coolant provided around the microwave antenna, and others.

Figure 48C:
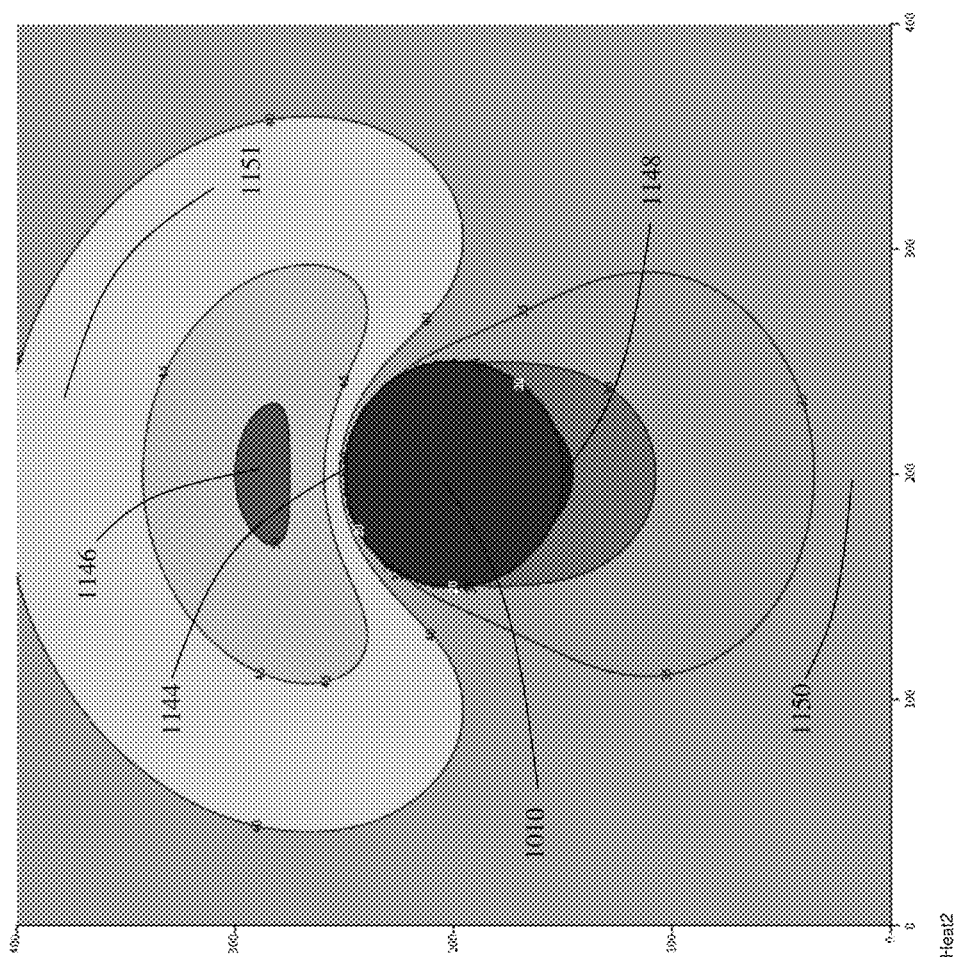

FIG. 48C depicts an extension of the 1-dimensional simulation to a 2-dimensional contour plot cross section within the treatment zone. In this plot the catheter 1010 is placed in the middle and the first contour line represents mucosa temperature (1144). The maximum temperature, 1146, is achieved directly above catheter 1010. This is the region of thermal injury. On the cool side of catheter 1010 is a maximum temperature 1150 no much above basal temperature and a mucosal temperature 1148 a bit lower than 1144. Adjacent tissue 1151 is below thermal damage.

FIG. 48C is a mesh blot of the temperature field in FIG. 48C for improved visualization. The highest temperature is the highest "elevation" on the plot and is marked 1146.

Figure 48D:
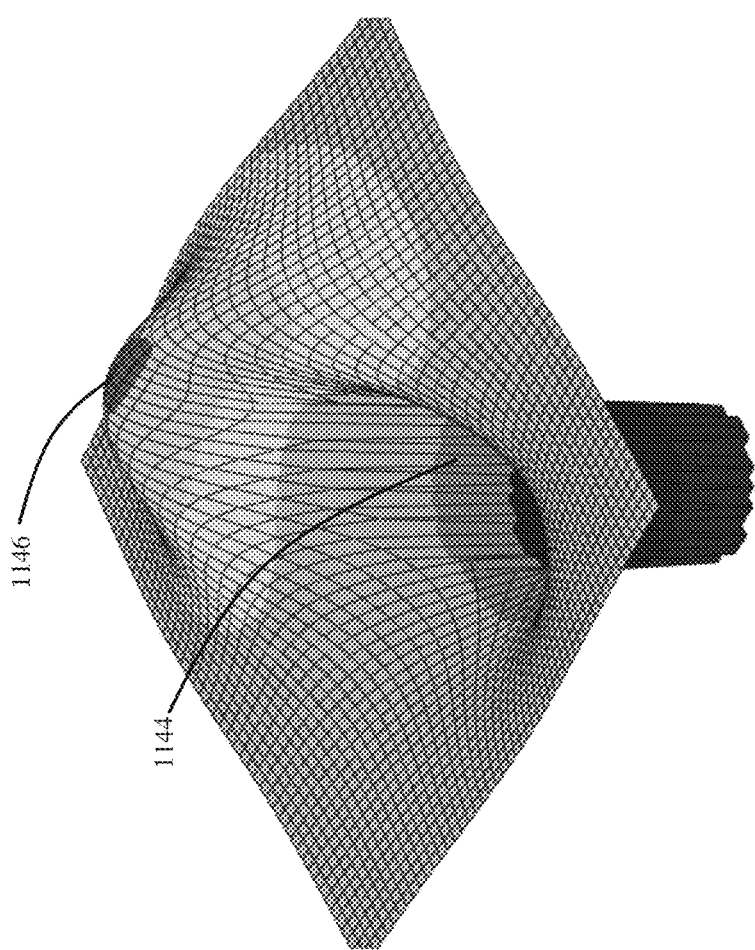

FIG. 48D depicts a surface plot of the 2-dimensional temperature field to provide another visualization. Maximum temperature is labeled 1146 and the cooled mucosa tissue temperature is labeled 1144.

Figures 49A, 49B:
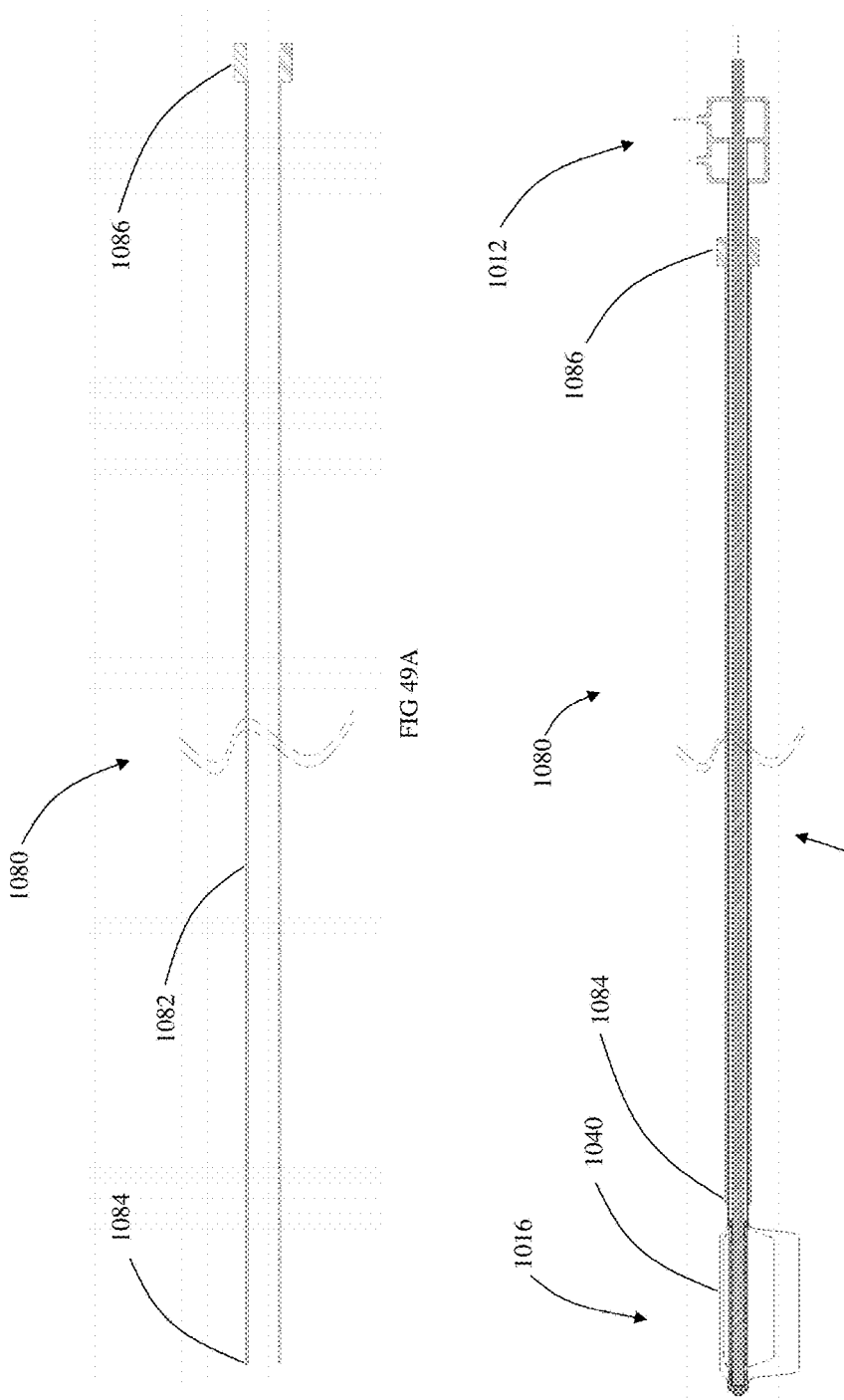
FIGS. 49A and 49B depict a guide catheter with and without a microwave carrying catheter placed within it.

FIG. 49A is a diagram of a guide catheter 1080. Guide catheter 1080 includes a tip 1084, a central shaft 1082, and a manifold 1086, and is sized to accommodate the pulmonary device.

FIG. 49B is a diagram of catheter 1010 placed within guide catheter 1080. Distal portion 1016 of catheter 1010 extends just beyond tip 1084 when the proximal end 1012 is conveniently close to manifold 1086.

Figure 49C:
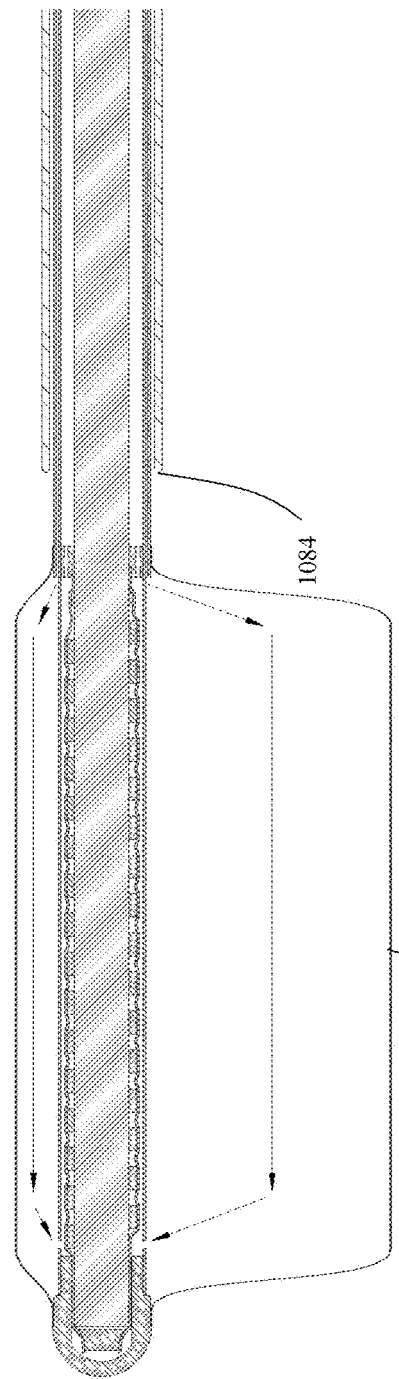
FIGS. 49C and 49D are more detailed diagrams of the distal and proximal regions of the guide catheter with a microwave antenna carrying catheter placed within it.

FIG. 49C is a diagram of the distal portion 1016 of catheter 1010 exiting guide catheter tip 1084. Balloon 1040 is shown inflated asymmetrically to provide the desired temperature field.

Figure 49D:
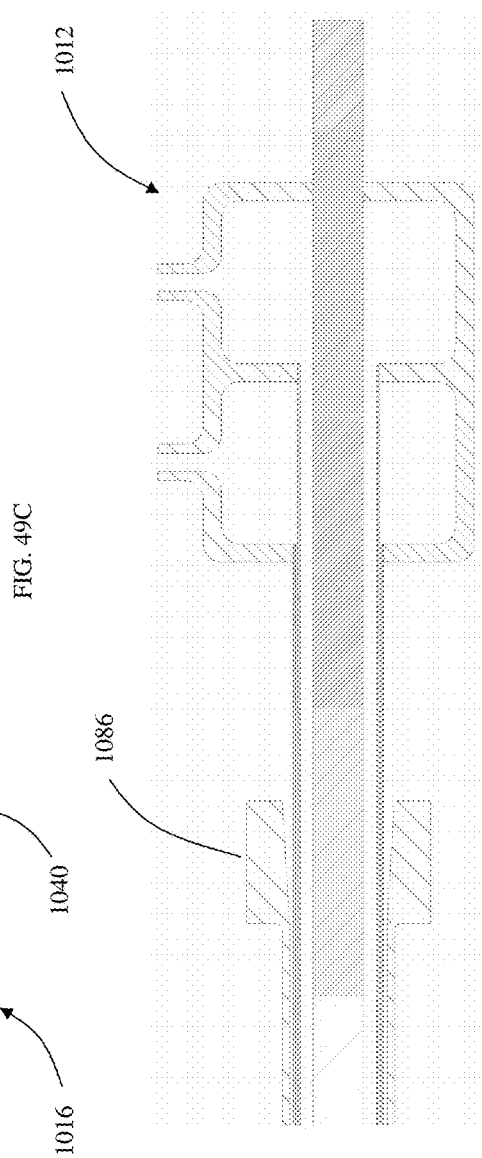

FIG. 49D is a diagram of the proximal portion 1012 of catheter 1010 entering manifold 1086 of guide catheter 1080.

FIG. 50 is a cross section of a bronchus just below the trachea. Four "tissue layers" are shown: The mucosa, 1096, the smooth muscle layer, 1098, the cartilage layer, 1100, and the surrounding tissue layer 1104 containing the targeted nerve trunk 1102. More distant tissue 1105 surrounds the bronchus. The airway lumen is 1095.

Figure 51A:
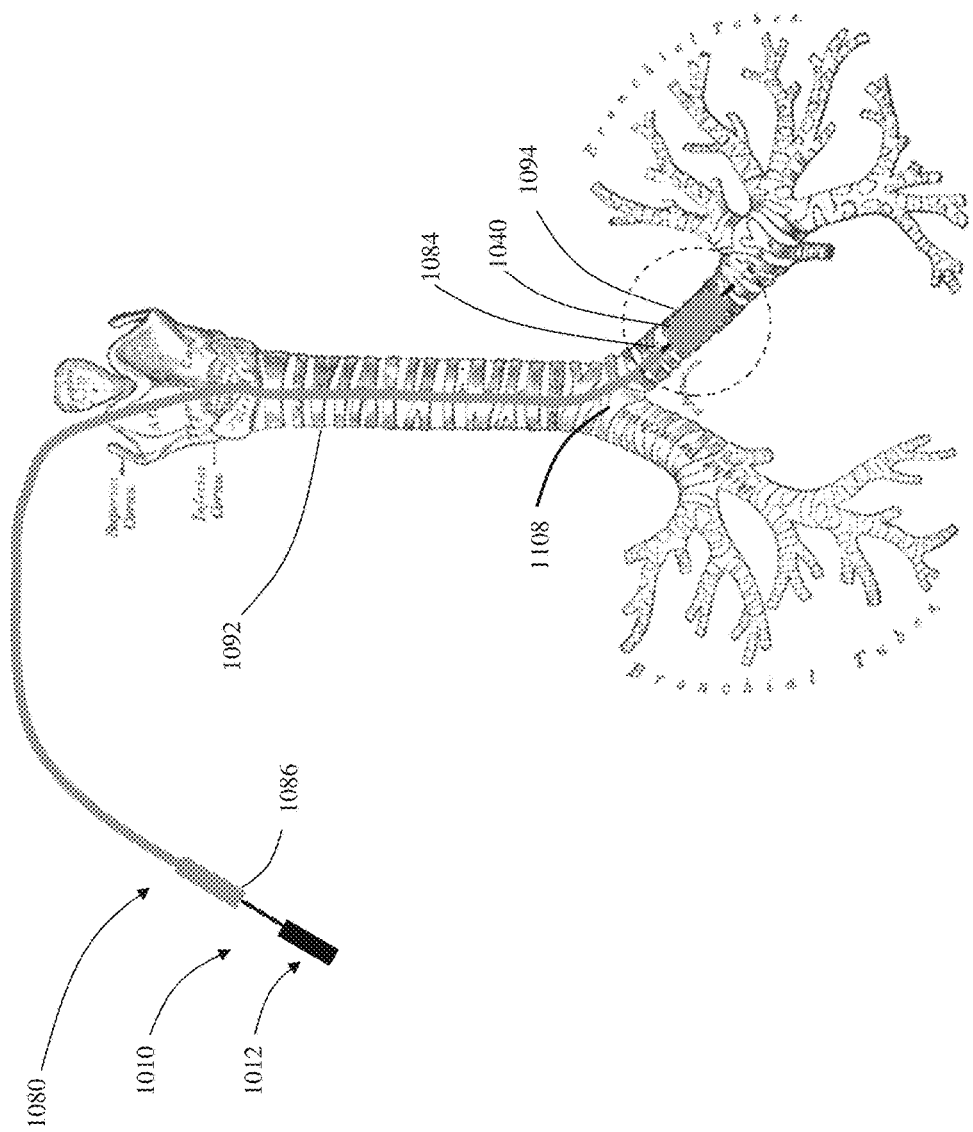
FIG. 51A is a detailed view of the microwave treatment catheter placed within the bronchial tree.

FIG. 51A is a diagram of the in-vivo placement of catheter 1010 using guide catheter 1080 within a human body. In order to perform pulmonary denervation therapy, guide catheter 1080 is introduced into the mouth of the patient and advanced into the desired bronchus 1094 via the trachea 1092 under guidance as known in the art. Microwave antenna carrying catheter 1010 is introduced into guide catheter 1080 by manifold 1086 and advanced until deflated balloon 1040 and microwave antenna 1046 are fully extended beyond tip 1084 of guide catheter 1080 and positioned within the desired bronchus 1094 in the region where the target nerve trunk runs along the bronchus. The position is confirmed by imagine prior to initiating the treatment algorithm.

FIG. 51B is an exploded diagram of the in-vivo placement of balloon 1040 and antenna 1046 within bronchus 1094. Balloon 1040 is inflated by circulating cooling fluid to contact mucosa 1096 of bronchus 1094. The smooth muscle layer is depicted by 1098, cartilage by 1100, and surrounding tissue containing the target nerve trunk by 1104. The nerve trunk, 1102, is not shown in this drawing.

Once properly located, cooling fluid generally below a normal basal body temperature of 37° C. is circulated through the space 1039 between outer body wall 1020 and inner body wall 1022 to interior region 1041 of balloon 1040, so that balloon 1040 is asymmetrically inflated to be in contact with the mucosa wall of the bronchus. Proper inflation of balloon 1040 may be confirmed by CT or other imaging. Simultaneous to the circulation of chilled cooling fluid, microwave power is then initiated according to the treatment algorithm and is supplied by a microwave generator to coaxial cable 1030, which feeds microwave antenna 1046 and causes microwave energy to be emitted preferentially at distal portion 1016 of catheter 1010 within bronchus 1094. The microwave energy emitted by microwave antenna 1046 causes tissue temperature to increase in the area surrounding microwave antenna 1046, while cooling fluid circulating through balloon 1040 cools the tissue immediately surrounding catheter 1010. The net result is that the tissue immediately surrounding distal portion 1016 of catheter 1010 (such as the mucosa, smooth muscle and cartilage of the bronchus) is maintained at a temperature where thermal damage will not occur, while tissue surrounding distal portion 1016 of catheter 1010 that is spaced some distance from inflated balloon 1040 (such as the surrounding tissue 1104 containing nerve trunk 1102) is heated to a temperature sufficient to cause thermal damage to the tissue. This allows pulmonary denervation to be performed without damaging the bronchus, in a single energization procedure that can cause the necessary thermal injury to the pulmonary nerve trunk in from 30 to 120 seconds. Shorter or longer duration energization may be desired in some embodiments.

Figures 52A, 52B:
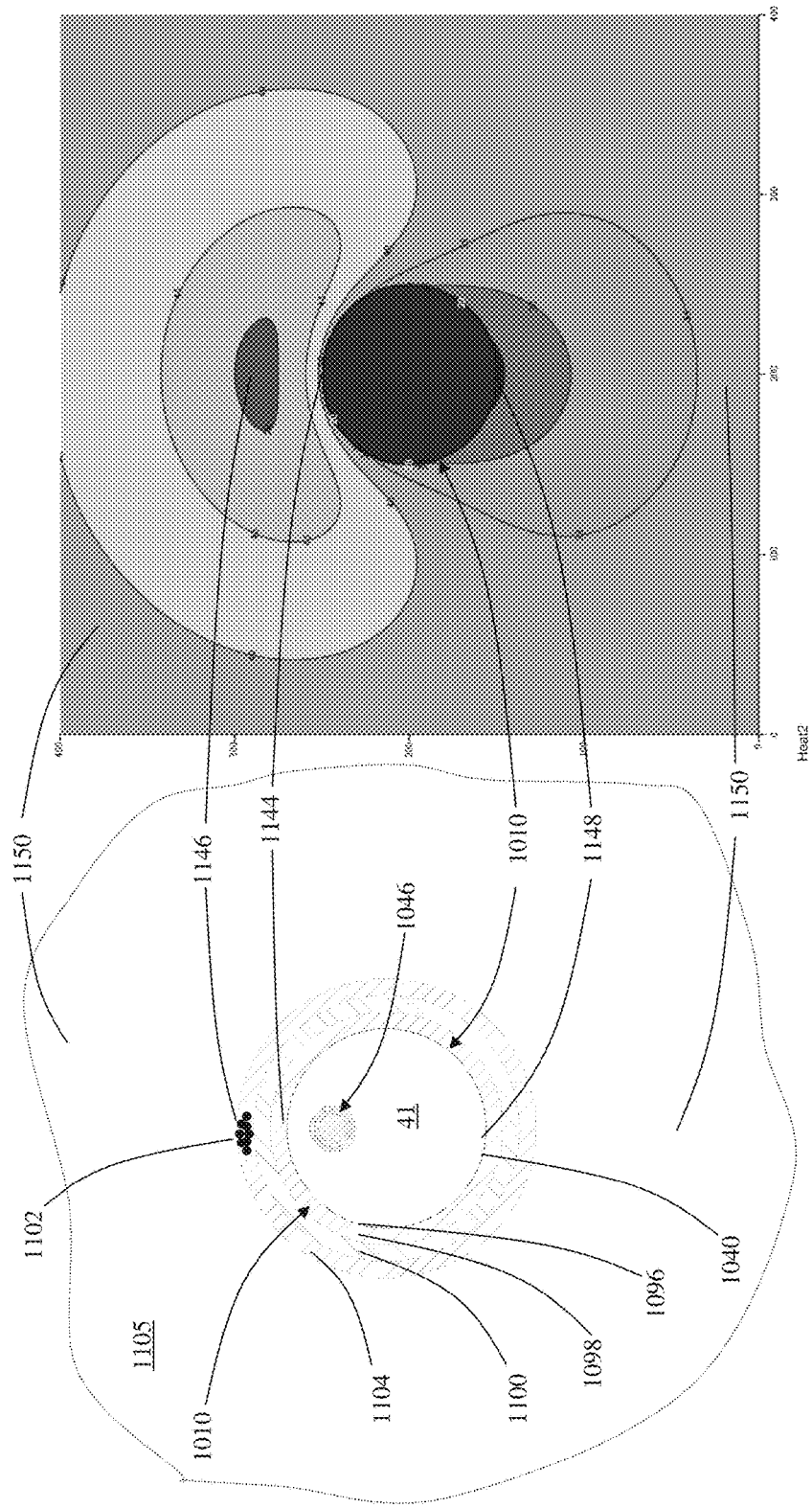
FIG. 52A is a cross sectional diagram of a bronchus with the microwave antenna carrying catheter placed within and the balloon inflated.
FIG. 52B is a cross sectional contour plot of temperature data from the microwave carrying catheter in which the maximum temperature is targeted at a nerve bundle depicted in FIG. 52A.

FIG. 52A is a diagram illustrating a cross section of catheter 1010 placed in the bronchus of a patient during pulmonary denervation. Microwave antenna 1046 is shown off set from the center of balloon 1040 placed within bronchus 1094. The mucosa 1096 is in contact with balloon 1040 such that heat transfer between mucosa 1096 and the cooling fluid in the interior 1041 of balloon may occur to keep mucosa 1096 cooled and protected from thermal injury—this concept can be referred to as "thermal contact" between the cooling fluid and mucosa 1096, through the wall of balloon 1040. Smooth muscle layer 1098 and cartilage layer 1100 surrounds mucosa 1096 and is cooled by heat transfer to mucosa 1096. Surrounding tissue layer 1104 containing target nerve trunk 1102 is exposed to the highest temperature 1146 at the location of nerve trunk 1102 and results in thermal ablation of nerve trunk 1102. More distant surrounding tissue 1104 does not receive sufficient heat to cause thermal damage, nor does other tissue maintained close to basal temperature 1150.

FIG. 52B is another simulation contour plot as described above for FIG. 48C but here it is scaled to match the size of the bronchus cross section so that the precise targeting of nerve trunk 1102 by temperature field maximum 1146 can be appreciated. The maximum temperature contour lines 1148 coincide with nerve trunk 1102. It can also be appreciated that the mucosa 1144 and 1148, smooth muscle 1098 and cartilage layer 1100 are located on cooler contour lines and therefore do not experience thermal damage. Temperature at distant tissue 1150 is maintained very near basal temperature and is undamaged.

Figure 53:
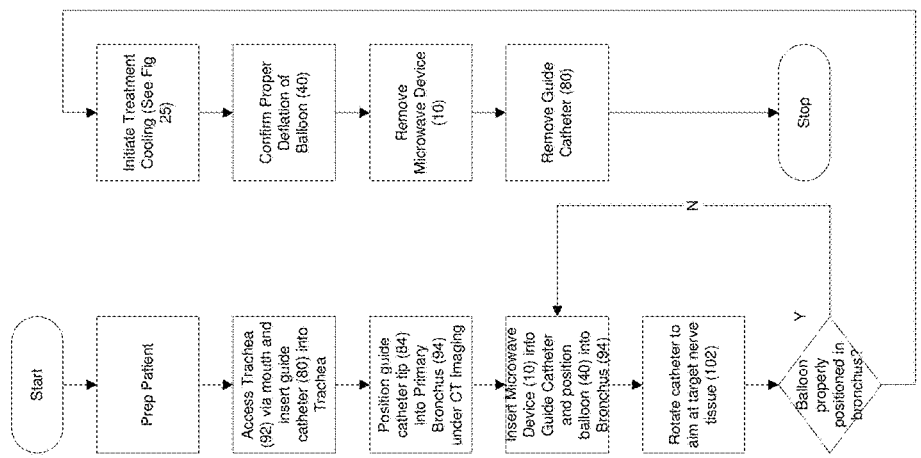
FIG. 53 is a flow chart illustrating the steps to perform pulmonary denervation according to an embodiment of the present invention.

FIG. 53 is a flowchart that depicts steps for the placement of the microwave carrying catheter 1010 within the bronchus 1094 to accomplish pulmonary denervation in accordance with the present invention. The patient is prepped as is well known in the art and the trachea is accessed via the mouth. A guide catheter is inserted according to FIG. 51A and advanced into the trachea 1092 and advanced until the distal tip 1084 of guide catheter 1080 is positioned within the desired bronchus 1094 using techniques known in the art. This is commonly accomplished with the use of CT guidance and the proper position of tip 1084 within bronchus 1094 may also be verified by CT guidance or other imaging. Microwave antenna containing catheter 1010 is advanced into guide catheter 1080 and positioned such that the entire balloon 1040 is contained within bronchus 1094 and the antenna coil windings 1048 are placed adjacent to the desired nerve trunk for pulmonary denervation. The catheter is rotated to angularly orient the preferentially heating to the target nerve trunk. Verification of the location and rotation of balloon 1040 is critical to successful pulmonary denervation so it is checked and repositioned as necessary. Once properly located, pulmonary denervation is initiated according to the procedure shown in FIG. 25 and described in detail above with respect to the renal denervation example. Proper inflation of balloon 1040 by cooling fluid within interior 1041 is also verified before initiating microwave power 1140. Once the pulmonary denervation treatment algorithm is completed, the balloon 40 will deflate when cooling flow is discontinued. The microwave carrying catheter 1010 may then be removed from guide catheter using techniques known in the art. The other bronchus is treated as described above if necessary, and then the catheter 1010 may be removed. The last steps are to remove guide catheter 1080 in accordance with known techniques. The patient is then monitored as is known in the art.

Catheter 1010 for pulmonary denervation via the bronchus is similar in a number of respects to the catheter embodiments described previously for performing renal denervation via the renal artery. As such, many of the characteristics, configurations and principles of the catheter embodiments described previously, such as with respect to FIGS. 37-45C for example, are applicable to catheter 1010 for performing pulmonary denervation, and may be incorporated in any combination thereof into the design and/or operation of catheter 1010 for pulmonary denervation.

While the directional aspect of pulmonary denervation with respect to catheter 1010 has been described above for the purpose of targeting a particular nerve trunk, there are other applications of directional capability of catheters utilizing at least some of the principles disclosed herein. For example, it is possible to use a catheter (such as a catheter configured similar to catheter 1010 described above in some embodiments) in a procedure that involves energizing the microwave antenna while circulating cooling fluid so as to target a first region of tissue on one side of the body lumen in which the catheter is inserted, rotating and optionally longitudinally shifting the catheter so that the angular orientation and optionally the position of the catheter is changed, and energizing the microwave antenna again while circulating cooling fluid so as to target a second region of tissue on a second side of the body lumen in which the catheter is inserted. This process could be repeated multiple times in some embodiments until an overall three-dimensional tissue region is ablated. The overall tissue region ablated by the series of energizations may be a circumferential (i.e., generally donut-shaped) lesion surrounding the body lumen, or may be a series of lesions that form a target pattern or that are spaced from one another to achieve a desired extent of ablation of tissue where targeted nerves are located.

Devices and methods are described herein for creating a lesion in tissue where targeted nerves are located, while preserving tissue adjacent to and forming the wall of the body lumen. A microwave antenna carrying catheter is employed to deliver the energy to create the lesion, and cooling fluid is circulated around the microwave antenna in thermal contact with the wall of the body lumen to preserve the tissue adjacent to and forming the wall of the body lumen. Specific examples for renal denervation and pulmonary denervation are disclosed. Denervation according to similar principles may be performed with a similar device and/or method in other body locations, including but not limited to the pulmonary artery and branches thereof, pulmonary veins including those near the right atrium, the entire pulmonary tree including the trachea, bronchus, and smaller branches deeper in the lung, the esophagus, the carotid artery, and others, which is expected to provide various beneficial effects to patients.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the disclosure and description provided herein.

The invention claimed is:

1. A catheter configured to create a lesion in adventitia tissue of a renal artery and/or tissue surrounding the adventitia tissue while protecting intima and media tissue of the renal artery from injury, the catheter comprising:
   a catheter body having at least one fluid passage therein;
   a balloon in communication with the at least one fluid passage to receive cooling fluid for inflating the balloon into a shape that surrounds the catheter body and contacts the intima tissue when the catheter body is positioned in the renal artery so that the catheter body is surrounded by the balloon when inflated at both a proximal end and a distal end of the balloon and the renal artery is occluded, the cooling fluid having a temperature that is less than basal body temperature; and
   a microwave antenna carried by the catheter, spaced from an outer wall of the balloon, the microwave antenna being connectable to a microwave generator to supply power to the microwave antenna to cause microwave energy to be emitted omnidirectionally from the microwave antenna, thereby heating the adventitia tissue and/or the tissue surrounding the adventitia tissue to a temperature sufficient to cause thermal damage while the intima and media tissue are maintained at a temperature above freezing where thermal damage does not occur by virtue of circulation of cooling fluid in the balloon around the microwave antenna,
   wherein the microwave antenna comprises at least one antenna coil wound around an outside of a coaxial cable, and the balloon surrounds an entire length of the at least one antenna coil; and wherein the at least one antenna coil is wound radially outward of an outer perimeter of the coaxial cable, in an interior of the balloon, with heat shrink material around the at least one antenna coil to separate the at least one antenna coil from the cooling fluid in the balloon.

2. The catheter of claim 1, wherein the lesion is a circumferential lesion in the adventitia tissue and/or the tissue surrounding the adventitia tissue.

3. The catheter of claim 1, wherein the lesion includes both the adventitia tissue of the renal artery and a region of tissue surrounding the adventitia tissue.

4. The catheter of claim 1, wherein the lesion is formed at a distance between 1.2 and 2.1 millimeters from the intima tissue.

5. The catheter of claim 1, wherein the lesion is formed at a distance that extends to 4.0 millimeters from the intima tissue.

6. The catheter of claim 1, wherein the microwave antenna is configured to produce a specific absorption rate (SAR) pattern having a single peak in a central region of the microwave antenna.

7. The catheter of claim 1, wherein the microwave antenna is configured to produce a specific absorption rate (SAR) pattern having two peaks spaced apart from one another.

8. The catheter of claim 1, further comprising at least one temperature sensor carried by the catheter to sense a temperature near the intima tissue.

9. The catheter of claim 1, wherein the balloon is inflatable to a diameter of about 6-7 mm.

10. The catheter of claim 1, wherein the at least one antenna coil comprises a first antenna coil connected to an inner conductor of the coaxial cable and a second antenna coil connected to an outer conductor of the coaxial cable.

11. The catheter of claim 10, wherein the first antenna coil and the second antenna coil have windings with non-uniform pitch.

12. The catheter of claim 1, wherein the heat shrink material around the at least one antenna coil comprises multiple layers of heat shrink material that are configured to create asymmetry in specific absorption rate (SAR) pattern peaks from the at least one antenna coil.

\* \* \* \* \*